(12) United States Patent
Liu et al.

(10) Patent No.: US 7,807,408 B2
(45) Date of Patent: Oct. 5, 2010

(54) DIRECTED EVOLUTION OF PROTEINS

(75) Inventors: David R. Liu, Lexington, MA (US); Joshua A. Bittker, Cambridge, MA (US); Jane M. Liu, Cambridge, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 712 days.

(21) Appl. No.: 11/107,335

(22) Filed: Apr. 15, 2005

(65) Prior Publication Data

US 2005/0260655 A1 Nov. 24, 2005

Related U.S. Application Data

(63) Continuation-in-part of application No. 10/101,461, filed on Mar. 19, 2002, now Pat. No. 7,678,554.

(60) Provisional application No. 60/277,015, filed on Mar. 19, 2001, provisional application No. 60/562,761, filed on Apr. 15, 2004.

(51) Int. Cl.
| C12P 21/06 | (2006.01) |
| C12P 19/34 | (2006.01) |
| C12Q 1/68 | (2006.01) |
| C12N 1/20 | (2006.01) |
| C12N 15/00 | (2006.01) |

(52) U.S. Cl. ............. 435/69.1; 435/6; 435/91.1; 435/252.3; 435/320.1

(58) Field of Classification Search .......... 435/6, 435/91.1, 91.2, 183, 69.1, 252.3, 320.1; 436/94, 436/501; 536/23.1, 24.3, 24.33, 25.3; 530/300, 530/350

See application file for complete search history.

(56) References Cited

U.S. PATENT DOCUMENTS

| 5,723,323 | A |   | 3/1998  | Kauffman et al. |
| 5,753,434 | A | * | 5/1998  | Ryner et al. ............... 435/6 |
| 5,756,291 | A |   | 5/1998  | Griffin et al. |
| 5,811,238 | A |   | 9/1998  | Stemmer et al. |
| 5,830,721 | A |   | 11/1998 | Stemmer et al. |
| 5,856,144 | A |   | 1/1999  | Mierendorf et al. |
| 5,962,219 | A |   | 10/1999 | Gold et al. |
| 6,110,900 | A |   | 8/2000  | Gold et al. |
| 6,114,120 | A |   | 9/2000  | Jensen et al. |
| 6,319,713 | B1 |  | 11/2001 | Patten et al. |
| 6,319,714 | B1 |  | 11/2001 | Crameri et al. |
| 6,352,842 | B1 |  | 3/2002  | Short et al. |
| 6,569,435 | B1 | * | 5/2003  | Punnonen et al. ........ 424/202.1 |
| 6,828,098 | B2 |  | 12/2004 | Langmore et al. |

(Continued)

OTHER PUBLICATIONS

Stemmer, Rapid evolution of a protein in vitro by DNA shuffling. Nature, 370, 389-391, 1994.*

(Continued)

*Primary Examiner*—Frank W Lu
(74) *Attorney, Agent, or Firm*—Thomas J. Engellenner; Nutter McClennen & Fish LLP

(57) ABSTRACT

Disclosed is a method of altering a nucleic acid such as RNA or DNA. The method comprises fragmenting a parent nucleic acid strand to generate nucleic acid fragments. At least a subset of the fragments are ligated to generate shuffled nucleic acid strands. A selected strand is identified from the shuffled nucleic acid strands for a criterion. The methods of the invention can also be used to diversify proteins.

19 Claims, 15 Drawing Sheets

U.S. PATENT DOCUMENTS

| | | | |
|---|---|---|---|
| 6,919,443 B1 | 7/2005 | Takahashi et al. | |
| 7,135,310 B2* | 11/2006 | Bradbury et al. | 435/91.1 |
| 2001/0039014 A1* | 11/2001 | Bass et al. | 435/6 |
| 2003/0027180 A1 | 2/2003 | Liu et al. | |

OTHER PUBLICATIONS

Bittker et al., "Directed Evolution of Protein Enzymes Using Nonhomologous Random Recombination", *PNAS*, v. 101, pp. 7011-7016, 2004.

Bittker et al., "Nucleic Acid Evolution and Minimization by Nonhomologous Random Recombination", *Nature Biotechnology*, v. 20, pp. 1024-1029, 2002.

Kawarasaki et al., "Enhanced Crossover SCRATCHY: Construction and High-Throughput Screening of a Combinatorial Library Containing Multiple Non-Homologous Crossovers", *Nucleic Acids Research*, v. 31, pp. 1-8, 2003.

Lutz et al., "Creating Multiple-Crossover DNA Libraries Independent of Sequence Identity", *PNAS*, v.98, pp. 11248-11253, 2001.

Lutz et al., "Novel Methods for Directed Evolution of Enzymes: Quality, Not Quantity", *Current Opinion in Biotechnology*, v. 15, pp. 291-297, 2004.

O'Maille et al., Structure-Based Combinatorial Protein Engineering (SCOPE), *J. Mol. Biol.*, v. 321, pp. 677-691, 2002.

Archemix website, printed 2002.

Diekmann, et al., "Mutant ATP-binding RNA Aptamers Reveal the Structural Basis for Ligand Binding", *J. Mol. Biol.* 273:467-478 (1997).

Ellington and Szostak, "In Vitro Selection of RNA Molecules That Bind Specific Ligands", *Nature* 346:818-822 (1990).

Ellington and Szostak, "Selection in vitro of single-stranded DNA molecules that fold into specific ligand-binding structures", *Nature* 355:850-852, 1992.

Famulok and Jenne, "Oligonucleotide Libraries—*Variatio Delectat*", *Curr Opin Chem Biol*, 2:320-327 (1998).

Hermann and Patel, "Adaptive Recognition by Nucleic Acid Aptamers", *Science* 287:820-825 (2000).

Huizenga and Szostak, "A DNA Aptamer That Binds Adenosine and ATP", *Biochemistry* 34:656-665 (1995).

Jaschke et al., "In Vitro Selected Oligonucleotides as Tools in Organic Chemistry", Synlett 6:825-833 (1999).

Jhaveri et al., "In Vitro Selection of Signaling Aptamers", *Nature Biotechnology* 18:1293-1297 (2000).

Kolkman and Stemmer, "Directed Evolution of Proteins by Exon Shuffling", *Nature Biotechnology* 19:423-428 (2001).

Liu et al., "Engineering a tRNA and aminoacyl-tRNA synthetase for the site-specific incorporation of unnatural amino acids into proteins in vivo," *Proc. Natl. Acad. Sci. USA*, 94:10092-10097 (1997).

Lorsch and Szostak, "In Vitro Selection of RNA Aptamers Specific for Cyanocobalamin", *Biochemistry* 33:973-982 (1994).

Lutz et al., "Creating Multiple-Crossover DNA Libraries Independent of Sequence Identity", *PNAS* 98:11248-11253 (2001).

Lugmani et al., "Subtraction hybridization cloning of RNA amplified from different cell populations microdissected from cryostat tissue section," *Analytical Biochemistry*, 222, 102-109 (1994).

Scott, "RNA catalysis," *Curr. Opin. Struct. Biol.*, 8:720-726 (1998).

Sen et al., "DNA enzymes," *Curr. Opin. Chem. Biol.*, 2:680-687 (1987).

Sieber et al, "Libraries of hybrid proteins from distantly related sequences," *Nature Biotechnology*, 19:456-460 (2001).

Stemmer, "Rapid evolution of a protein in vitro by DNA shuffling," *Nature*, 370:389-391 (1994).

Tsuji et al., "Random multi-recombinant PCR for the construction of combinatorial protein libraries," *Nucleic Acids Research*, vol. 29, No. 20, 97:1-10 (2001).

Wells, "A beginning, of sorts, for antisense," *Chemistry & Biology*, 6:R49-R50 (1999).

Wilson et al., "Functional Requirements for Specific Ligand Recognition by a Biotin-Binding RNA Pseudoknot," *Biochemistry*, 37:14410-14419 (1998).

* cited by examiner

A

B

C

A

B

| | Sample[a] | Activation Activity[b] | RNA Levels[c] |
|---|---|---|---|
| Group 1 | A40 | 6.6 | ++ |
| | A43 | 3.3 | + |
| | A45 | 11.6 | +++ |
| | DsrA | 3.9 | +++ |
| Group 2 | A35ab | 4.7 | + |
| | A35ac | 1.4 | + |
| Group 3 | A40 | 6.6 | ++ |
| | A40a | 1.6 | ++ |
| | A40b | 4.3 | ++ |
| | A40c | 7.6 | ++ |

[a]Sequences include additonal 3'Ts, see text and Figure 3C
[b]LacZ activity relative to pRNA, see Figure 3C
[c]Intracellular abundance determined by qRT-PCR, see Figure 4C

SEQUENCE LISTING

<160> NUMBER OF SEQ ID NOS: 58

<210> SEQ ID NO 1
<211> LENGTH: 62
<212> TYPE: DNA
<213> ORGANISM: Artificial
<220> FEATURE:
<223> OTHER INFORMATION: SYNTHETIC CONSTRUCT

<400> SEQUENCE: 1
gggaattcta gaagcttccc gggggggcccg cgcgggcccc ccgggaagct tctagaattc          60
cc                                                                         62

<210> SEQ ID NO 2
<211> LENGTH: 62
<212> TYPE: DNA
<213> ORGANISM: Artificial
<220> FEATURE:
<223> OTHER INFORMATION: SYNTHETIC CONSTRUCT

<400> SEQUENCE: 2
gggtccggat acgaattccc cgggggcccg cgcgggcccc cggggaattc gtatccggac          60
cc                                                                         62

<210> SEQ ID NO 3

```
<211> LENGTH: 62
<212> TYPE: DNA
<213> ORGANISM: Artificial
<220> FEATURE:
<223> OTHER INFORMATION: SYNTHETIC CONSTRUCT

<400> SEQUENCE: 3
ctgtccggat acaagcttca gctgggcccg cgcgggccca gctgaagctt gtatccggac      60
ag                                                                    62

<210> SEQ ID NO 4
<211> LENGTH: 21
<212> TYPE: DNA
<213> ORGANISM: Artificial
<220> FEATURE:
<223> OTHER INFORMATION: SYNTHETIC CONSTRUCT

<400> SEQUENCE: 4
ctgaagcttg tatccggaca g                                               21

<210> SEQ ID NO 5
<211> LENGTH: 64
<212> TYPE: DNA
<213> ORGANISM: Artificial
<220> FEATURE:
<223> OTHER INFORMATION: SYNTHETIC CONSTRUCT

<400> SEQUENCE: 5
cctccgcggc atccgaattc aggcctccgg gcgcccggag gcctgaattc ggatgccgcg      60
gagg                                                                  64

<210> SEQ ID NO 6
<211> LENGTH: 23
<212> TYPE: DNA
<213> ORGANISM: Artificial
<220> FEATURE:
<223> OTHER INFORMATION: SYNTHETIC CONSTRUCT

<400> SEQUENCE: 6
cctgaattcg gatgccgcgg agg                                             23

<210> SEQ ID NO 7
<211> LENGTH: 44
<212> TYPE: DNA
<213> ORGANISM: Artificial
<220> FEATURE:
<223> OTHER INFORMATION: SYNTHETIC CONSTRUCT
<220> FEATURE:
<221> NAME/KEY: misc_feature
<222> LOCATION: (22)..(22)
<223> OTHER INFORMATION: n is a, c, g, or t

<400> SEQUENCE: 7
gccccgcgga tgggacgtcc cncgcccgcg gcatccgacg tccc                      44

<210> SEQ ID NO 8
<211> LENGTH: 22
<212> TYPE: DNA
<213> ORGANISM: Artificial
<220> FEATURE:
<223> OTHER INFORMATION: SYNTHETIC CONSTRUCT

<400> SEQUENCE: 8
gggacgtcgg atgccgcggg cg                                              22
```

```
<210> SEQ ID NO 9
<211> LENGTH: 200
<212> TYPE: DNA
<213> ORGANISM: Artificial
<220> FEATURE:
<223> OTHER INFORMATION: SYNTHETIC CONSTRUCT

<400> SEQUENCE: 9
cgggggtgcc cgctgctcgt ccaaatgacg gctcagcttc ggtgggcctt taacagtaat        60
caatcatatg agcagttttc aacgatcacc tacccacacc gctcgaatgt ttgcataaac       120
ctgggtagac tcacgcataa ttgggttatt gagtctcttt gatggactaa cccggttcta       180
tctcggaggt attttaggtc                                                   200

<210> SEQ ID NO 10
<211> LENGTH: 274
<212> TYPE: DNA
<213> ORGANISM: Artificial
<220> FEATURE:
<223> OTHER INFORMATION: SYNTHETIC CONSTRUCT

<400> SEQUENCE: 10
tgacacaaag acagacaggc tatccaagaa ccctcttact ctgtgagacg acgcaccggt        60
cgcaggtttt gtctcacaga cgctaaaaat acagacatgc accaatgaac aatgagttcg       120
accgtgttct tgagttttat ggccgatgtg gtaagtactt ctactgtatc ttcgcgtacc       180
ttaggtttaa cgttctcttt ttcggaatgt gctcgcccgc ggcatccgac gtccctttgg       240
ggggtaggtg caacgggaat cttgagggat catt                                   274

<210> SEQ ID NO 11
<211> LENGTH: 223
<212> TYPE: DNA
<213> ORGANISM: Artificial
<220> FEATURE:
<223> OTHER INFORMATION: SYNTHETIC CONSTRUCT

<400> SEQUENCE: 11
gaaaactgct catatgattg attagcccgc tgctcgtcca atgacggct cagctctgta         60 tttttagcgt ctgtgagaca gaacctgcga ccggtgcgtc gtctcacagt ctactgtatc       120
ttcgcgtacc ttaggtttac ccgctgctcg tccaaatgac ggctctctgt gagacaaaac       180
ctgcgaccgg tgcgtcgtct cacagtaaga gggttcttgg ata                         223

<210> SEQ ID NO 12
<211> LENGTH: 150
<212> TYPE: DNA
<213> ORGANISM: Artificial
<220> FEATURE:
<223> OTHER INFORMATION: SYNTHETIC CONSTRUCT

<400> SEQUENCE: 12
caagaacacg gtcgaactca ttgttcattg gtgcactgtg agacaaaacc tgcgaccggt        60
gcgtcgtctc acaggagata gaaccgggtt agtccatcaa agagactctg tgagacaaaa       120
cctgcgaccg gtgcgtcgtc tcacagagta                                        150

<210> SEQ ID NO 13
<211> LENGTH: 40
<212> TYPE: DNA
<213> ORGANISM: Artificial
<220> FEATURE:
<223> OTHER INFORMATION: SYNTHETIC CONSTRUCT
```

```
<400> SEQUENCE: 13
tctgtgagac gacgcaccgg tcgcaggttt tgtctcacag                              40

<210> SEQ ID NO 14
<211> LENGTH: 66
<212> TYPE: DNA
<213> ORGANISM: Artificial
<220> FEATURE:
<223> OTHER INFORMATION: SYNTHETIC CONSTRUCT

<400> SEQUENCE: 14
catacacgtc atccgaattc aggcctccgg gcgcgcccgg aggcctgaat tcggatgacg        60
tgtatg                                                                   66

<210> SEQ ID NO 15
<211> LENGTH: 68
<212> TYPE: DNA
<213> ORGANISM: Artificial
<220> FEATURE:
<223> OTHER INFORMATION: SYNTHETIC CONSTRUCT

<400> SEQUENCE: 15
catggtgacc catccgaatt caggcctgcc ggcgcgccgg caggcctgaa ttcggatggg        60
tcaccatg                                                                 68

<210> SEQ ID NO 16
<211> LENGTH: 23
<212> TYPE: DNA
<213> ORGANISM: Artificial
<220> FEATURE:
<223> OTHER INFORMATION: SYNTHETIC CONSTRUCT

<400> SEQUENCE: 16
cctgaattcg gatgacgtgt atg                                                23

<210> SEQ ID NO 17
<211> LENGTH: 24
<212> TYPE: DNA
<213> ORGANISM: Artificial
<220> FEATURE:
<223> OTHER INFORMATION: SYNTHETIC CONSTRUCT

<400> SEQUENCE: 17
cctgaattcg gatgggtcac catg                                               24

<210> SEQ ID NO 18
<211> LENGTH: 31
<212> TYPE: DNA
<213> ORGANISM: Artificial
<220> FEATURE:
<223> OTHER INFORMATION: SYNTHETIC CONSTRUCT

<400> SEQUENCE: 18
tttttgtttt tgttctgggt ttcttccag g                                        31

<210> SEQ ID NO 19
<211> LENGTH: 26
<212> TYPE: DNA
<213> ORGANISM: Artificial
<220> FEATURE:
<223> OTHER INFORMATION: SYNTHETIC CONSTRUCT

<400> SEQUENCE: 19
atgatcgaaa aactggcaga aatccg                                             26
```

-continued

```
<210> SEQ ID NO 20
<211> LENGTH: 30
<212> TYPE: DNA
<213> ORGANISM: Artificial
<220> FEATURE:
<223> OTHER INFORMATION: SYNTHETIC CONSTRUCT

<400> SEQUENCE: 20
atgaatacag tacgcagcga aaaagattcg                                   30

<210> SEQ ID NO 21
<211> LENGTH: 25
<212> TYPE: DNA
<213> ORGANISM: Artificial
<220> FEATURE:
<223> OTHER INFORMATION: SYNTHETIC CONSTRUCT

<400> SEQUENCE: 21
acgcccggct ttcatactgc cgacc                                        25

<210> SEQ ID NO 22
<211> LENGTH: 67
<212> TYPE: DNA
<213> ORGANISM: Artificial
<220> FEATURE:
<223> OTHER INFORMATION: SYNTHETIC CONSTRUCT

<400> SEQUENCE: 22
catacacgtc atccgaattc aggcctccgg gcgcgcccgg aggcctgaat tccggatgac   60
gtgtatg                                                            67

<210> SEQ ID NO 23
<211> LENGTH: 66
<212> TYPE: DNA
<213> ORGANISM: Artificial
<220> FEATURE:
<223> OTHER INFORMATION: SYNTHETIC CONSTRUCT

<400> SEQUENCE: 23
catggtcacc catccgaatt cagctggcgg cggccgccgc cagctgaatt cggatgggtg   60
accatg                                                             66

<210> SEQ ID NO 24
<211> LENGTH: 23
<212> TYPE: DNA
<213> ORGANISM: Artificial
<220> FEATURE:
<223> OTHER INFORMATION: SYNTHETIC CONSTRUCT

<400> SEQUENCE: 24
cctgaattcg gatgacgtgt atg                                          23

<210> SEQ ID NO 25
<211> LENGTH: 23
<212> TYPE: DNA
<213> ORGANISM: Artificial
<220> FEATURE:
<223> OTHER INFORMATION: SYNTHETIC CONSTRUCT

<400> SEQUENCE: 25
ctgaattcgg atgggtgacc atg                                          23

<210> SEQ ID NO 26
```

```
<211> LENGTH: 40
<212> TYPE: DNA
<213> ORGANISM: Artificial
<220> FEATURE:
<223> OTHER INFORMATION: SYNTHETIC CONSTRUCT
<220> FEATURE:
<221> NAME/KEY: misc_feature
<222> LOCATION: (17)..(17)
<223> OTHER INFORMATION: n is a, c, g, or t

<400> SEQUENCE: 26
ggcggcggcg gtgaccncta gccatgacac acgtggcggc                              40

<210> SEQ ID NO 27
<211> LENGTH: 24
<212> TYPE: DNA
<213> ORGANISM: Artificial
<220> FEATURE:
<223> OTHER INFORMATION: SYNTHETIC CONSTRUCT

<400> SEQUENCE: 27
gccgccacgt gtgtcatgga ctag                                              24

<210> SEQ ID NO 28
<211> LENGTH: 18
<212> TYPE: DNA
<213> ORGANISM: Artificial
<220> FEATURE:
<223> OTHER INFORMATION: SYNTHETIC CONSTRUCT

<400> SEQUENCE: 28
gaaacggagc ggcacctc                                                     18

<210> SEQ ID NO 29
<211> LENGTH: 19
<212> TYPE: DNA
<213> ORGANISM: Artificial
<220> FEATURE:
<223> OTHER INFORMATION: SYNTHETIC CONSTRUCT

<400> SEQUENCE: 29
gcggatcctg gagatccgc                                                    19

<210> SEQ ID NO 30
<211> LENGTH: 40
<212> TYPE: DNA
<213> ORGANISM: Artificial
<220> FEATURE:
<223> OTHER INFORMATION: SYNTHETIC CONSTRUCT

<400> SEQUENCE: 30
aacacatcag atttcctggt gtaacgaatt ttttaagtgc                              40

<210> SEQ ID NO 31
<211> LENGTH: 34
<212> TYPE: DNA
<213> ORGANISM: Artificial
<220> FEATURE:
<223> OTHER INFORMATION: SYNTHETIC CONSTRUCT

<400> SEQUENCE: 31
aatcccgacc ctgaggggt cgggatgaac ttgc                                    34

<210> SEQ ID NO 32
<211> LENGTH: 11
<212> TYPE: DNA
<213> ORGANISM: Artificial
```

-continued

<220> FEATURE:
<223> OTHER INFORMATION: SYNTHETIC CONSTRUCT

<400> SEQUENCE: 32 tttttttgc c                                                         11

<210> SEQ ID NO 33
<211> LENGTH: 30
<212> TYPE: DNA
<213> ORGANISM: Artificial
<220> FEATURE:
<223> OTHER INFORMATION: SYNTHETIC CONSTRUCT

<400> SEQUENCE: 33
ggcaaaaaaa agcggatcct ggagatccgc                                    30

<210> SEQ ID NO 34
<211> LENGTH: 60
<212> TYPE: DNA
<213> ORGANISM: Artificial
<220> FEATURE:
<223> OTHER INFORMATION: SYNTHETIC CONSTRUCTS

<400> SEQUENCE: 34 ctttttttg ccacacgtga attcggcccg cgggccgaat tcacgtgtgg caaaaaaag     60

<210> SEQ ID NO 35
<211> LENGTH: 26
<212> TYPE: DNA
<213> ORGANISM: Artificial
<220> FEATURE:
<223> OTHER INFORMATION: SYNTHETIC CONSTRUCT

<400> SEQUENCE: 35
gcgaattcac gtgtggcaaa aaaaag                                        26

<210> SEQ ID NO 36
<211> LENGTH: 21
<212> TYPE: DNA
<213> ORGANISM: Artificial
<220> FEATURE:
<223> OTHER INFORMATION: SYNTHETIC CONSTRUCT

<400> SEQUENCE: 36
caagaagcac ttaaaaaatt c                                             21

<210> SEQ ID NO 37
<211> LENGTH: 18
<212> TYPE: DNA
<213> ORGANISM: Artificial
<220> FEATURE:
<223> OTHER INFORMATION: SYNTHETIC CONSTRUCT

<400> SEQUENCE: 37
gatccgcaaa agttcacg                                                 18

<210> SEQ ID NO 38
<211> LENGTH: 18
<212> TYPE: DNA
<213> ORGANISM: Artificial
<220> FEATURE:
<223> OTHER INFORMATION: SYNTHETIC CONSTRUCT

<400> SEQUENCE: 38
aacgcgctag cggtgacc                                                 18

<210> SEQ ID NO 39
<211> LENGTH: 9
<212> TYPE: DNA
<213> ORGANISM: Artificial
<220> FEATURE:
<223> OTHER INFORMATION: SYNTHETIC CONSTRUCT

<400> SEQUENCE: 39 ttttattgt                                                                  9

<210> SEQ ID NO 40
<211> LENGTH: 9
<212> TYPE: DNA
<213> ORGANISM: Artificial
<220> FEATURE:
<223> OTHER INFORMATION: SYNTHETIC CONSTRUCT

<400> SEQUENCE: 40 ttttattgt                                                                  9

<210> SEQ ID NO 41
<211> LENGTH: 5
<212> TYPE: RNA
<213> ORGANISM: Artificial
<220> FEATURE:
<223> OTHER INFORMATION: SYNTHETIC CONSTRUCT

<400> SEQUENCE: 41 aacau                                                                      5

<210> SEQ ID NO 42
<211> LENGTH: 6
<212> TYPE: RNA
<213> ORGANISM: Artificial
<220> FEATURE:
<223> OTHER INFORMATION: SYNTHETIC CONSTRUCT

<400> SEQUENCE: 42 aacgaa                                                                     6

<210> SEQ ID NO 43
<211> LENGTH: 7
<212> TYPE: RNA
<213> ORGANISM: Artificial
<220> FEATURE:
<223> OTHER INFORMATION: SYNTHETIC CONSTRUCT

<400> SEQUENCE: 43 uaacgaa                                                                    7

<210> SEQ ID NO 44
<211> LENGTH: 11
<212> TYPE: DNA
<213> ORGANISM: Artificial
<220> FEATURE:
<223> OTHER INFORMATION: SYNTHETIC CONSTRUCT

<400> SEQUENCE: 44 tttttttgc c                                                               11

<210> SEQ ID NO 45
<211> LENGTH: 368
<212> TYPE: DNA
<213> ORGANISM: Escherichia coli

<400> SEQUENCE: 45

```
agcaccggaa ccagttcaac acgcttgcat tttgaaattc gttacaaggg gaaatccgta      60
aacccgctgc gttatttgcc gcagcgataa atcggcggaa ccaggctttt gcttgaatgt     120
tccgtcaagg gatcacgggt aggagccacc ttatgcagaa tacgctgaaa gttcatgatt     180
taaatgaaga tgcggaattt gatgagaacg gagttgaggt ttttgacgaa aaggccttag     240
tagaacagga acccagtgat aacgatttgc gggaagagga actgttatgc cagggagcca     300
cacagcgtgt gttggacgcg actcagcttt accttggtga gattggttat tcaccactgt     360
taacggcc                                                              368
```

<210> SEQ ID NO 46
<211> LENGTH: 41
<212> TYPE: RNA
<213> ORGANISM: Escherichia coli

<400> SEQUENCE: 46

```
uugcauuuug aaauucguua caaggggaaa uccguaaacc c                          41
```

<210> SEQ ID NO 47
<211> LENGTH: 41
<212> TYPE: RNA
<213> ORGANISM: Escherichia coli

<400> SEQUENCE: 47

```
aacacaucag auuuccuggu guaacgaauu uuuuaagugc u                          41
```

<210> SEQ ID NO 48
<211> LENGTH: 87
<212> TYPE: RNA
<213> ORGANISM: Escherichia coli

<400> SEQUENCE: 48

```
aacacaucag auuuccuggu guaacgaauu uuuuaagugc uucuugcuua agcaaguuuc      60
aucccgaccc ccucaggguc gggauuu                                          87
```

<210> SEQ ID NO 49
<211> LENGTH: 109
<212> TYPE: RNA
<213> ORGANISM: Escherichia coli

<400> SEQUENCE: 49

```
gaaacggagc ggcaccucuu uuaacccuug aagucacugc ccguuucgag aguuucucaa      60
cucgaauaac uaaagccaac gugaaguuuu gcggaucucc aggauccgc                 109
```

<210> SEQ ID NO 50
<211> LENGTH: 87
<212> TYPE: DNA
<213> ORGANISM: Escherichia coli

<400> SEQUENCE: 50

```
aacacatcag atttcctggt gtaacgaatt ttttaagtgc ttcttgctta agcaagtttc      60
atcccgaccc cctcagggtc gggattt                                          87
```

<210> SEQ ID NO 51
<211> LENGTH: 61
<212> TYPE: RNA
<213> ORGANISM: Artificial Sequence
<220> FEATURE:
<223> OTHER INFORMATION: Synthetic Construct

```
<400> SEQUENCE: 51
aacacaucag auuccuggu guaacgaauu uuuuaagugc uucaaauccc gacccugagg    60
g                                                                  61

<210> SEQ ID NO 52
<211> LENGTH: 11
<212> TYPE: RNA
<213> ORGANISM: Artificial Sequence
<220> FEATURE:
<223> OTHER INFORMATION: Synthetic Construct

<400> SEQUENCE: 52
aacauaacga a                                                       11

<210> SEQ ID NO 53
<211> LENGTH: 18
<212> TYPE: RNA
<213> ORGANISM: Escherichia coli

<400> SEQUENCE: 53
gguguaacga auuuuuua                                                18

<210> SEQ ID NO 54
<211> LENGTH: 30
<212> TYPE: DNA
<213> ORGANISM: Escherichia coli

<400> SEQUENCE: 54
gaaacggagc ggcacctctt ttaacccttg                                   30

<210> SEQ ID NO 55
<211> LENGTH: 16
<212> TYPE: RNA
<213> ORGANISM: Escherichia coli

<400> SEQUENCE: 55
uuaaaugaag augcgg                                                  16

<210> SEQ ID NO 56
<211> LENGTH: 15
<212> TYPE: RNA
<213> ORGANISM: Escherichia coli

<400> SEQUENCE: 56
cggcaccucu uuuaa                                                   15

<210> SEQ ID NO 57
<211> LENGTH: 13
<212> TYPE: RNA
<213> ORGANISM: Escherichia coli

<400> SEQUENCE: 57
ggaaauccgu aaa                                                     13

<210> SEQ ID NO 58
<211> LENGTH: 13
<212> TYPE: RNA
<213> ORGANISM: Escherichia coli

<400> SEQUENCE: 58
uuugcggauc ucc                                                     13
```

DIRECTED EVOLUTION OF PROTEINS

PRIORITY INFORMATION

This application is a continuation in part application of U.S. application Ser. No. 10/101,461, filed on Mar. 19, 2002, now U.S. Pat. No. 7,678,554 B2, which claims priority to U.S. Provisional Patent Application Ser. No. 60/277,015, filed on Mar. 19, 2001, and claims priority to U.S. Provisional Patent Application Ser. No. 60/562,761, filed on Apr. 15, 2004, which are expressly incorporated by reference.

BACKGROUND

Proteins and nucleic acids employ only a small fraction of the available functionality. In vitro molecular evolution efforts include diversification of a starting molecule into related variants from which desired molecules are chosen. Methods used to generate diversity in nucleic acid and protein libraries include whole genome mutagenesis (Hart et al., *Amer. Chem. Soc.* (1999), 121: 9887-9888), random cassette mutagenesis (Reidhaar-Olson et al,. *Meth. Enzymol.* (1991), 208: 564-86), error-prone PCR (Caldwell, et al. (1992), *PCR Methods Applic.* (1992), 2: 28-33), and DNA shuffling using homologous recombination (Stemmer (1994) *Nature* (1994), 370: 389-391). After diversification, molecules with novel or enhanced properties can be selected.

Methods that enable recombination to take place at defined sites without sequence homology have been recently described. For example, it is possible to recombine unrelated protein-encoding genes by using synthetic oligonucleotides to encode each desired crossover (O'Maille (2002) *J. Mol. Biol.* 321: 677-91; and Tsuji (2001) *Nuc. Acids Res.* 29:E97). Although this strategy can result in a high likelihood of preserving function after diversification, many fewer sites of recombination, and therefore, fewer novel structures are accessible than if crossover sites are randomly generated. Alternatively, methods allowing a single nonhomologous crossover of two protein-encoding genes have been developed (Sieber (2001) *Nat. Biotechnol.* 19: 456-60; and Ostermeier (1999) *Nat. Biotechnol* 17: 1205-9), and additional nonhomologous recombination events can be obtained by fragmenting and homologously recombining the resulting genes (Lutz (2001) *Proc. Natl. Acad. Sci. USA* 98: 11248-5317). Despite efforts to enhance the number of crossovers obtained, existing methods for diversifying proteins by non-homologous recombination have thus far yielded only modest numbers of recombination events (three or fewer per 500 base pair (bp) in protein-encoding sequences, with even fewer crossovers (one to two per 500 bp) among sequences encoding active proteins (Kawarasaki (2003) *Nuc. Acids Res.* 31: e12618).

Accordingly a need exists for a simple, effective method of diversifying nucleic acids proteins.

SUMMARY

The invention is based, in part, on the discovery that the random shuffling of fragments of a nucleic acid can provide a diverse pool of novel nucleic acids (e.g. DNA, RNA) that include nucleic acids with new and/or enhanced properties. Likewise, the present invention provides simple methods for diversifying proteins and protein domains. In particular, the methods and compositions of the invention can be used to create entirely new protein folds, which are more likely to require the recombination of nonhomologous genes.

Accordingly, in one aspect, the invention pertains to a method for producing an evolved protein comprising randomly fragmenting parent nucleic acid strands to generate three or more nucleic acid fragments from each parent nucleic acid strand, wherein at least one of the parent nucleic acid strands is capable of encoding a protein and atleast one of the resulting nucleic acid fragment is capable of encoding a protein fragment. At least a subset of the nucleic acid fragments can be ligated to generate shuffled nucleic acid strands, wherein at least one of the shuffled nucleic acid strands comprises nucleic acid fragments from at least two of the parent nucleic acid strands. The shuffled nucleic acid strands can be transformed into a host cell; and the evolved protein encoded by the shuffled nucleic acid strand can be expressed.

In another aspect, the invention pertains to a method for producing an evolved protein comprising fragmenting parent nucleic acid strands encoding a protein with at least one structural feature to generate three or more nucleic acid fragments from each parent nucleic acid strand, in which at least one nucleic acid fragment encodes a protein fragment. At least a subset of the nucleic acid fragments are ligated at random to generate shuffled nucleic acid strands, in which at least one of the shuffled nucleic acid strands comprises nucleic acid fragments from at least two of the parent nucleic acid strands and encodes an evolved protein having a structural feature from each parent. The shuffled nucleic acid strands can be transformed into a host cell; and the evolved protein encoded by the shuffled nucleic acid strand can be expressed.

The parent nucleic acid strands are non-homologous and non-complementary, and the parent nucleic acid strands can be fragmented by a non-site specific agent, such as the non-specific endonuclease Dnase I. The nucleic acid fragments preferably have a terminus that can be ligated to at least one non-adjacent fragment.

The method further comprises ligating a hairpin oligonucleotide to at least a subset of the fragmented nucleic acid strands and these hairpin oligonucleotides can then be digested. The nucleic acid fragments can have at least one nucleic acid fragment that is inserted, deleted, or rearranged to produce shuffled nucleic acid fragments that encode evolved protein fragments. The average size of the shuffled nucleic acid fragments encoding an evolved protein is less than 2000 nucleotides, less than 1000 nucleotides, less than 500 nucleotides, less than 400 nucleotides, less than 300 nucleotides, less than 200 nucleotides, less than 100 nucleotides, and less than 50 nucleotides.

In one embodiment, the method can be used to produce a library of evolved proteins comprising fragmenting parent nucleic acid strands encoding a protein with at least one structural feature to generate three or more nucleic acid fragments from each parent nucleic acid strand, wherein at least one nucleic acid fragment encodes a protein fragment; ligating at least a subset of the nucleic acid fragments at random to generate plurality of shuffled nucleic acid strands, where at least one of the shuffled nucleic acid strands comprises nucleic acid fragments from at least two of the parent nucleic acid strands and encodes an evolved protein having a protein structural feature from each parent; transforming the plurality of shuffled nucleic acid strands into a host cell; and expressing a plurality of evolved polypeptides encoded by the plurality of shuffled nucleic acid strands.

In another aspect, the invention pertains to a method for producing an evolved chimeric protein comprising fragmenting a first nucleic acid strand encoding a first protein with at least one structural feature to generate three or more nucleic acid fragments, where at least one nucleic acid fragment encodes a first protein fragment; fragmenting a second nucleic acid strand encoding a second protein with at least one structural feature to generate three or more nucleic acid fragments, where at least one nucleic acid fragment encodes a second protein fragment. At least a subset of the nucleic acid fragments that encode the first protein fragment can be ligated with at least a subset of the nucleic acid fragments that encode the second protein fragment at random to generate shuffled chimeric nucleic acid strands, where at least one of the shuffled chimeric nucleic acid strands comprises a nucleic acid fragment that encodes a first protein fragment and a nucleic acid fragment that encodes a second protein fragment. The shuffled chimeric nucleic acid strands can be transformed into a host cell; and the evolved chimeric protein encoded by the shuffled chimeric nucleic acid strand can be expressed.

The first nucleic acid strand encoding the first protein and the second nucleic acid strand encoding the second protein are preferably non-homologous and non-complementary.

The nucleic acid fragment encoding the first protein fragment can have a terminus that can be ligated to at least one non-adjacent fragment. The nucleic acid fragment encoding the second protein fragment can also have a terminus that can be ligated to at least one non-adjacent fragment. The first and second nucleic acid strands can be fragmented by a non-site specific agent, such as DNase I.

The method further comprises ligating a hairpin oligonucleotide to at least a subset of the fragmented first and second nucleic acid strands and digesting the hairpin oligonucleotides. In some embodiments, at least two species of hairpin oligonucleotides can be added to the reaction during the ligation step, wherein each species of hairpin oligonucleotides comprises a different nonpalindromic restriction endonuclease cleavage site.

A preselection of active proteins can be accomplished using an expressing vector that fuses the evolved protein to CAT (chloramphenicol acetyl-transferase). Most protein products that contain internal stop codons when introduced into this vector are unable to propagate in *E. coli* cells in the presence of chloramphenicol. This preselection step can be done to eliminate evolved proteins that are unable to be expressed or that are insoluable.

The nucleic acid fragments can have at least one nucleic acid fragment that is inserted, deleted, or rearranged to produce shuffled chimeric nucleic acid fragments that encode evolved chimeric protein fragments. The average size of the shuffled nucleic acid fragments encoding an evolved protein is less than 2000 nucleotides, less than 1000 nucleotides, less than 500 nucleotides, less than 400 nucleotides, less than 300 nucleotides, less than 200 nucleotides, less than 100 nucleotides, and less than 50 nucleotides.

In one embodiment, the method can be used to produce a library of evolved chimeric proteins comprising fragmenting a first nucleic acid strand encoding a first protein with at least one structural feature to generate three or more nucleic acid fragments, where at least one nucleic acid fragment encodes a first protein fragment; and fragmenting a second nucleic acid strand encoding a second protein with at least one structural feature to generate three or more nucleic acid fragments, where at least one nucleic acid fragment encodes a second protein fragment. At least a subset of the nucleic acid fragments that encode the first protein fragment can be ligated with at least a subset of the nucleic acid fragments that encode the second protein fragment at random to generate a plurality of shuffled chimeric nucleic acid strands, where at least one of the shuffled chimeric nucleic acid strands from the plurality comprises a nucleic acid fragment that encodes a first protein fragment and a nucleic acid fragment that encodes a second protein fragment. The plurality of shuffled chimeric nucleic acid strands can be transformed into a host cell, and a plurality of evolved chimeric proteins encoded by the plurality shuffled chimeric nucleic acid strands can be expressed.

In yet another aspect, the invention pertains to an evolved protein comprising a first at least one protein fragment from a first parent protein and a second at least one protein fragment from a second parent protein, wherein the evolved protein is produced using the method of this invention. In some embodiments, the invention pertains to an evolved protein comprising a protein fragment with at least one structural feature from a first region of the protein and at least one structural feature from a second region of the protein, where the protein fragment is created using the method of the invention.

The structural feature from the first region of the protein can be a structural feature such as a helical structure, a sheet structure, a loop structure or a combination thereof. In one embodiment, the structural feature from the first region of the protein is an α-helix. The structural feature from the second region of the protein can also be a structural feature such as a helical structure, a sheet structure, a loop structure or a combination thereof. In one embodiment, the structural feature from the second region of the protein is an α-helix.

In yet another aspect, the invention pertains to an evolved is a chorismate mutase enzyme comprising a protein fragment with at least one structural feature from a first region of the chorismate mutase enzyme and at least one structural feature from a second region of the chorismate mutase enzyme, where the chorismate mutase enzyme is created using the method of the invention. The structural feature from the first region of the chorismate mutase enzyme can be an α-helix and the structural feature from the second region of the chorismate mutase enzyme can also be an α-helix.

In yet another aspect, the invention pertains to an evolved chimeric protein comprising a protein fragment from a first protein with at least one structural feature and a protein fragment of a second protein with at least one structural feature, where the chimeric protein is created using the method of the invention. The structural feature from the first protein can be a helical structure, a sheet structure, a loop structure or a combination thereof. The structural feature from the second protein can also be a helical structure, a sheet structure, a loop structure or a combination thereof.

In yet another aspect, the invention pertains to an evolved chimeric chorismate mutase-fumarase protein comprising a protein fragment from a chorismate mutase enzyme and a second protein fragment from a furmarase protein, wherein the chimeric chorismate mutase-fumarase protein is using the method of the invention. In some embodiments, the evolved chimeric chorismate mutase-fumarase protein comprises a protein fragment with at least one structural feature from a chorismate mutase enzyme and at least one structural feature from a furmarase protein, wherein the chimeric chorismate mutase-fumarase protein is created using the method of the invention. In one embodiment, the structural feature from the chorismate mutase enzyme is an α-helix. In another embodiment, the structural feature from the furmarase is an α-helix.

The non-homologous random recombination method of the invention can also be used to evolve RNA molecules such as small non-coding RNAs (sRNA). Therefore, in another aspect, the invention pertains to a method for producing evolved ribonucleic acids comprising fragmenting parent ribonucleic acid strands to generate three or more ribonucleic acid fragments from each parent ribonucleic acid strand. At least a subset of the ribonucleic acid fragments can be ligated at random to generate shuffled ribonucleic acid strands, where at least one of the shuffled ribonucleic acid strands comprises ribonucleic acid fragments from at least two of the parent ribonucleic acid strands. The shuffled ribonucleic acid strands can be transformed into a host cell, and evolved ribonucleic acid strands with a desired functional activity can be selected.

The parent ribonucleic acid strands can be non-homologous and non-complementary, and can be fragmented by a non-site specific agent such as DNase. The ribonucleic acid fragment can have a terminus that can be ligated to at least one non-adjacent fragment.

The method further comprising ligating a hairpin oligonucleotide to at least a subset of the fragmented ribonucleic acid strands and digesting the hairpin oligonucleotide. The ribonucleic acid fragments have at least one ribonucleic acid fragment that is inserted, deleted, or rearranged to produce shuffled ribonucleic acid fragments.

In one embodiment, the evolved ribonucleic acid can be an mRNA, tRNA, rRNA, sRNA, and the like. In a preferred embodiment, the RNA is a small ribonucleic acid. The small ribonucleic acid can have structural elements such as SL1, SL2, SL3, SL1-SL2 linker, SL2-SL3 linker, or fragments and combinations thereof. The evolved ribonucleic acid may interact with an RNA chaperone such as Hfq, MS2, U1A, UP1, and the like.

The desired functional activity used to select the evolved RNA can be any activity involving an RNA, such as initiation of mRNA transcription, repression of mRNA transcription and termination of mRNA transcription.

The average size of the shuffled ribonucleic acid fragments can be less than 500 nucleotides, less than 500 nucleotides, less than 400 nucleotides, less than 300 nucleotides, less than 200 nucleotides, or less than 100 nucleotides.

In one embodiment, the method further comprising producing a library of evolved ribonucleic acids comprising fragmenting parent ribonucleic acid strands to generate three or more ribonucleic acids fragments from each parent nucleic acid strand. At least a subset of the ribonucleic acid fragments can be ligated at random to generate plurality of shuffled ribonucleic acid strands, where at least one of the shuffled ribonucleic acid strands comprises ribonucleic acid fragments from at least two of the parent ribonucleic acid strands. The plurality of shuffled ribonucleic acid strands can be transformed into a host cell, and the evolved ribonucleic acid strands with a desired functional activity can be selected.

In another aspect, the invention pertains to an evolved ribonucleic acid fragment with at least one structural element from a first region of a parent ribonucleic acid strand and at least one structural element from a second region the parent ribonucleic acid, wherein the evolved ribonucleic acid fragment is produced by the method of the invention. The structural element from the first region of the parent ribonucleic acid strand can be structural elements such as SL1, SL2, SL3, SL1-SL2 linker, SL2-SL3 linker, or fragments and combinations thereof. The structural element from the second region of the parent ribonucleic acid strand can also be structural elements such as SL1, SL2, SL3, SL1-SL2 linker, SL2-SL3 linker, or fragments and combinations thereof. The evolved ribonucleic acid may interact with an RNA chaperone such as Hfq, UP1, and the like. The evolved ribonucleic acid may also have a desired functional activity such as initiation of mRNA transcription, repression of mRNA transcription and termination of mRNA transcription.

DETAILED DESCRIPTION

Figure 1:
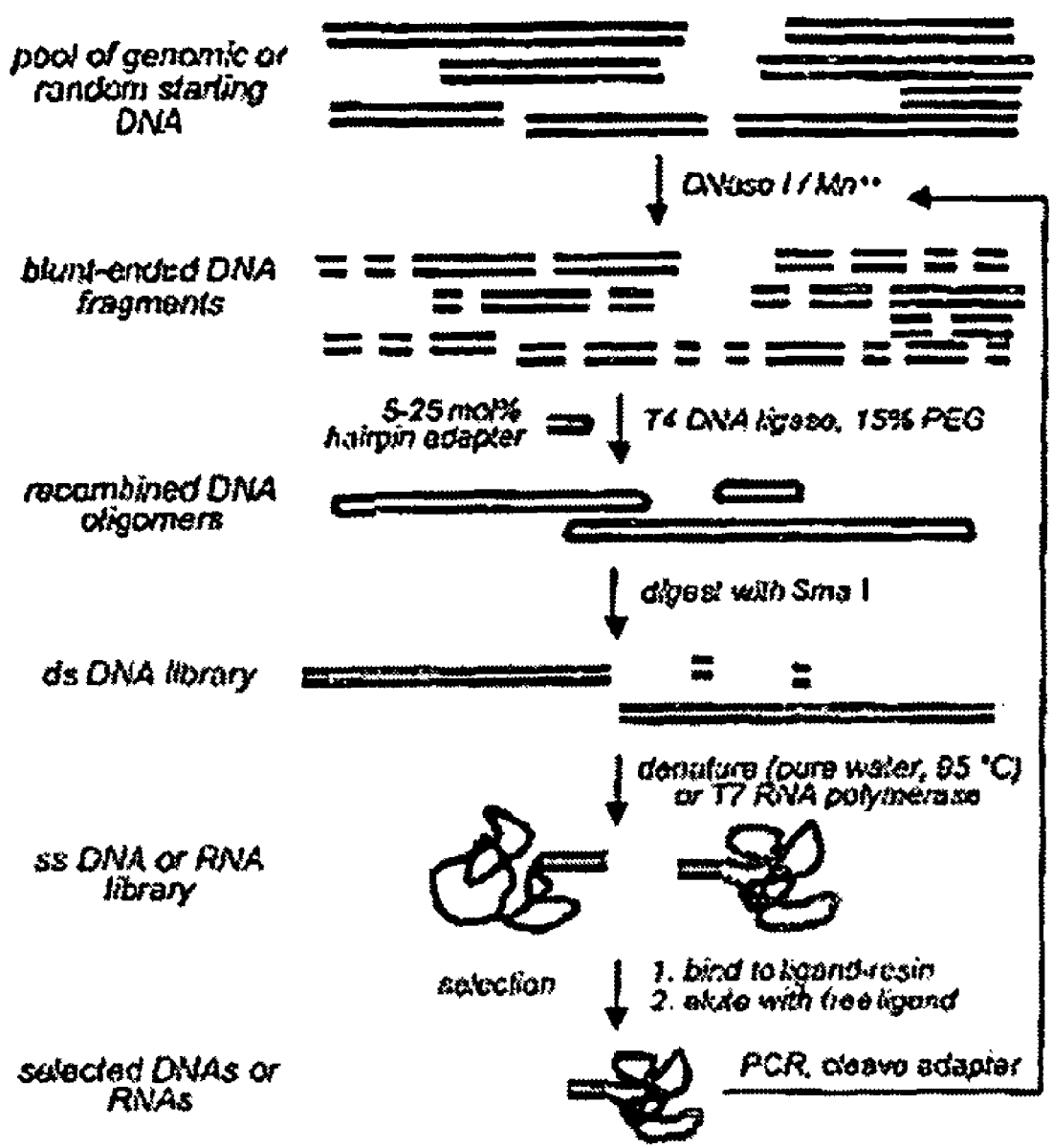
FIG. 1 is a schematic of an example of the nucleic acid shuffling method.

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

The invention provides shuffled nucleic acid sequence by ligation of nucleic acid fragments obtained from parent strands, such as non-homologous parent strands. The method is referred to as the nucleic acid shuffling method (and also as "Non-homologous Random Recombination" or "NRR"). The method does not require homology between the parental strands for recombination. However, at least in some cases, such homology may be present.

So that the invention is more clearly understood, the following terms are defined:

The term "evolved" refers to a process of change that results in the production of new nucleic acids and polypeptides that retain at least some of the structural features or elements and/or functional activity of the parent nucleic acids or polypeptides from which they have developed. In some instances, the evolved nucleic acids or polypeptides have increased or enhanced activity compared with the parent. In some instances, the evolved nucleic acids or polypeptides have decreased or reduced activity compared with the parent.

The term "non-homologous" refers to two nucleic acid sequences having sufficient number of differences that the two sequences are unable to recombine with each other in a standard host cell, particularly in an *E. coli* cell. The term "in vitro non-homologous" refers to two nucleic acid sequences having sufficient number of differences that the two sequences are unable to recombine using an in vitro recombination method such as the recombination method generally described in Stemmer. *Nature* (1994), 370: 389-391.

The term "shuffled" refers to a molecule having at least one fragment rearranged, reoriented, inserted, or deleted with respect to an appropriate reference polymer, e.g., a parent molecule.

The term "random" refers to condition wherein events are determined by a probability distribution. The distribution may include a bias, e.g., dependent on the relative concentrations of starting material. For example, in one embodiment, the parental nucleic acid strands may include a biased amount of one species relative to another. The ligation of a mixture of fragments generated from such a pool of starting material can nevertheless be random.

The term "oligonucleotide," as used herein refers to a nucleic acid polymer of about 5 to 140 nucleotides in length.

The term "protein," as used herein refers to a sequence of amino acids that have a function and/or activity. Examples of activities of proteins include, but are not limited to, enzymatic activity, kinase activity, and binding activity, which can be shown through a variety of spectroscopic, radioactive, or direct binding assays which are known in the art. For example, see Sigma Aldrich for a collection of test kits and assays for biological activity.

The term "structural feature" as used herein refers to a sequence of amino acids. In some embodiments, the sequence of amino acids can confer a secondary structure, such as a helical structure, a sheet structure, a loop structure, a turn structure or a combination thereof The term nucleic acid "aptamer," as used herein, refers to a nucleic acid molecule which has a conformation that includes an internal non-duplex nucleic acid structure of at least 5 nucleotides. For example, an aptamer can be a single-stranded nucleic acid molecule which has regions of self-complementarity. For another example, an aptamer can be nucleic acid molecule which binds a ligand other than a nucleic acid.

A "hairpin nucleic acid," "hairpin oligonucleotide," or "hairpin" refers to a nucleic acid that includes a first, second, and third region such that the first region is complementary, (e.g., 95%, 99%, or 100%) to the third region, and the second region is complementary to neither the first nor the third region.

The term "binds," and "binding" refer to a physical interaction for which the apparent dissociation constant of two molecules is at least 0.1 mM. Binding affinities can be less than about 10 µM, 1 µM, 100 nM, 10 nM, 1 nM, 100 pM, 10 pM, and so forth.

The term "ligand" refers to a compound which can be specifically and stably bound by a molecule of interest.

The term "non-coding property" refers to a property of a nucleic acid molecule that is not a mere function of a protein that it may (or may not) encode. Examples of non-coding properties include specific binding and catalysis.

I. Evolved Nucleic Acids

In one aspect, the methods of the invention can be used to create evolved nucleic acids, e.g., RNA, sRNA, single-stranded DNA, or double stranded DNA. The method involves randomly fragmenting parent nucleic acid strands to generate three or more nucleic acid fragments from each parent nucleic acid strand. At least a subset of the nucleic acid fragments can be ligated to generate shuffled nucleic acid strands, and then evolved nucleic acids having a desired property, activity or criterion, can be selected from the shuffled nucleic acid strands. Typically, the fragmenting and ligating are performed in vitro. The method can be used for altering nucleic acid sequences, e.g., for non-homologous shuffling of two or more different parent nucleic acid strands.

In one embodiment, the parent nucleic acid strands are non-homologous and/or non-complementary. In another embodiment, the parent nucleic acid strands are less than about 90%, 80%, 70%, 60%, 50%, 40%, 30%, or 20% identical, on average. Some strands may be at least partially homologous. In still another embodiment, the parent nucleic acid strands do not substantially anneal to one another at temperature below 55, 50, 45, 40, 35, or 30° C. under physiological conditions.

At least one of the shuffled nucleic acid strands, or at least 25, 50, or 75% of the strands include nucleic acid fragments from at least two of the parent nucleic acid strands. The nucleic acid fragments can have at least one terminus that can be ligated to at least one non-adjacent fragment. For example, the nucleic acid fragments can be double-stranded and can have at least one terminus that is a blunt end. Both termini can be blunt ends. The fragments can be less than about 2000, 1000, 700, 600, 500, 400, 300, 200, 100, or 50 nucleotides in length, and/or greater than about 10, 20, 40, 60, 80, 100, 200, or 500 nucleotides in length.

The median size of the shuffled nucleic acids can be less than about 2000, 1000, 700, 600, 500, 400, 300, 200, 100, or 50 nucleotides in length, and/or greater than about 10, 20, 40, 60, 80, 100, 200, or 500 nucleotides in length. In one embodiment, the method further includes isolating shuffled nucleic acid strands that are within a predetermined size range (e.g., the median size ranges above). The identifying includes identifying a selected strand from the isolated shuffled nucleic acid strands.

The number of different shuffled nucleic acids that are produced can be between $10^2$-$10^{16}$, e.g., $10^4$-$10^{16}$, $10^6$-$10^{15}$, or $10^9$-$10^{15}$.

The method can optionally include selecting some of the nucleic acid fragments by size to remove the fragments less than 20, 30, 40, 50, 60, 70, 80, 90, or 100 nucleotides in length, or greater than 100, 200, 300, 400, 500, 1000, or 2000 nucleotides in length, thereby obtaining a pool of shuffled nucleic acid strands having a average length between 10-100, 20-200, 30-300, 40-400, 50-500, 50-800, or 50-2000 nucleotides in length. The separation step can be a precipitation, electrophoretic separation, or chromatographic separation.

The ligation can be performed under conditions in which each fragment can be ligated to at least a non-adjacent fragment. The ligation can be performed such that the sequence and composition of the shuffled nucleic acid strands is random. The ligation can include a compound that increases the percentage of intermolecular ligation events, such as a molecular crowding agent or an agent that increases the viscosity of the solution, e.g., polyethylene glycol is an example of a compound with both properties.

The parent nucleic acid strands can be randomly fragmented in the same container or in different containers and then combined. The parent nucleic acid strands can be randomly fragmented, for example, with a non-site specific agent such as a nonspecific endonuclease (e.g., DNaseI), a restriction enzyme (e.g., a Type II enzyme, four-base cutter, a Type IIS enzyme), a chemical reagent (e.g., a hydroxyl radical generator such as Fe(II)-EDTA-hydrogen peroxide), or a physical method (such as sonication or shearing).

The method can further include ligating a hairpin oligonucleotide to at least a subset of the shuffled nucleic acid strands; cleaving the shuffled nucleic acid strands with a endonuclease (e.g., a Type II restriction enzyme, or a Type IIS restriction enzyme) which cleaves in the hairpin oligonucleotide, and amplifying the shuffled nucleic acid strands with a primer, e.g., a primer which anneals to a sequence in the hairpin oligonucleotide. The hairpin oligonucleotide can include a sequence that is a promoter of RNA transcription, e.g., a T7 polymerase promoter, or a transcription terminator.

The method can further include ligating a synthetic oligonucleotide to at least one fragment. The synthetic oligonucleotide can include, for example, a random sequence; a aptamer features such as a tetraloop, a bulge, or a hairpin; or a sequence encoding a patterned peptide. The synthetic oligonucleotide can be added into the ligation at a variety of molar ratios, e.g., between 0.001 and 0.2 or 0.01 and 0.05.

The criterion for selecting evolved, diversified nucleic acids can be a physical criterion (e.g., size, conformation, or structural stability) or a functional criterion (e.g., ability to bind a ligand, ability to catalyze an reaction, or ability to modulate a process). The selection step can include contacting the shuffled nucleic acid strands to a ligand, e.g., a ligand attached to a solid support, and selecting one or more strands that bind the ligand. The selection step can include a wash, e.g., multiple washes of increasing stringency, or a wash with a competing compound, e.g., a compound known to bind the ligand. The ligand can be a polypeptide or a small molecule ligand, or generally any molecule that can be immobilized or differentiated.

The method can also further include amplifying the shuffled nucleic acid strands, e.g., using a primer that anneals to the hairpin oligonucleotide to produce amplified shuffled nucleic acid strands; denaturing the amplified shuffled nucleic acid strands to form a first and a second nucleic acid strand; and cooling the first and second nucleic acid strand such that the first strand does not form a nucleic acid duplex with the second strand and such that the termini of the first strand anneal one another to form an intramolecular duplex.

In another aspect, the invention features a method of altering a nucleic acid. The method includes randomly fragmenting a parent nucleic acid strand to generate three or more nucleic acid fragments, each nucleic acid fragment having a terminus that can be ligated to at least one non-adjacent fragment, and ligating a hairpin nucleic acid and at least a subset of the nucleic acid fragments to generate shuffled nucleic acid strands, each shuffled nucleic acid strand including at least one inserted, deleted, or rearranged nucleic acid fragment relative to the parent nucleic acid strand; amplifying the shuffled nucleic acid strands using a primer that anneals to the hairpin nucleic acid; selecting a strand from the amplified shuffled nucleic acid strands for a criterion.

In still another aspect, the invention features a method of altering a polypeptide. The method includes: providing a parent nucleic acid strand encoding a parent polypeptide; fragmenting the parent nucleic acid strand to generate three or more nucleic acid fragments, each nucleic acid fragment having a terminus that can be ligated to at least one non-adjacent fragment; ligating at least a subset of the nucleic acid fragments to generate a shuffled nucleic acid strand, wherein the shuffled nucleic acid strand has at least one nucleic acid fragment inserted, deleted, or rearranged; and expressing a shuffled polypeptide encoded by the shuffled nucleic acid strand.

The fragmenting can be such that the parent nucleic acid strand is fragmented by a non-site specific agent (e.g., a non-specific endonuclease), and/or the average size of the fragments is less than 2000 nucleotides.

Referring to the example in FIG. 1, a pool of genomic DNA or random starting DNA is randomly digested with DNaseI in the presence of manganese. The DNase I digestion of these parent nucleic acid strands generates 5'-phosphorylated DNA fragments of approximately 10-100 bp in length. The average length of the fragments used for shuffling is monitored and controlled by regulating the DNase I digestion conditions, e.g., temperature, enzyme concentration, substrate concentration and divalent cation concentration. The fragmenting reaction is terminated and the fragments separated from the inactivated DNaseI. These fragments are enzymatically transformed into blunt-ended double strands of DNA by reaction with T4 DNA polymerase, which catalyzes both the extension of 5' overhangs and the exonucleolytic cleavage of 3' overhangs to leave 5' phosphates (Campbell et al. *J. Biol. Chem.* 1980, 255, 3726-3725.). Klenow DNA polymerase can also be used, e.g., if the fragmenting method does not generate 3' overhangs. The polymerase reaction is terminated, and the blunted fragments are purified from the reaction mixture. The blunted fragments are then randomly ligated together using T4 DNA ligase, which catalyzes the efficient ligation of blunt-ended DNA independent of sequence. The ligation reaction includes 15% polyethylene glycol (PEG), e.g., of average molecular weight about 4000 to 8000 Daltons. PEG was observed to increase the frequency of intermolecular ligation events as described below.

DNA hairpins can also be included in the ligation reaction to control the average length of the ligated shuffled nucleic acid strand library and to ensure that all library members are flanked by defined sequences suitable for PCR or subcloning. One or more DNA hairpins of defined sequence are added to these intermolecular ligation reactions, e.g., prior to or after addition of DNA ligase. The terminus of DNA molecule capped by ligation to a hairpin can no longer ligate to other molecules. The DNA hairpins can be included at any concentration, for example, at a molar concentration of 0.0001% to 100%, 0.1% to 90%, 1% to 50%, or 2% to 25% of the molar concentration of the nucleic acid fragments. Higher concentrations of a DNA hairpin tends to lowers the average molecular weight of the shuffled nucleic acids, whereas a reduced concentrations of a DNA hairpin tends to yield shuffled nucleic acids with longer average lengths. The user can, therefore, regulate the length of the produced shuffled nucleic acid strand. Control of this parameter, for example, allows the evolution of nucleic acids that are minimized relative to parental nucleic acids or that are expanded relative to parental nucleic acids.

The process can include digesting the ligation reaction with a restriction enzyme that cleaves the ends of each hairpin, and subjecting the resulting double-stranded material to the polymerase chain reaction (PCR) using a primer complementary in sequence to a sequence in the hairpin. The PCR conditions, e.g., error-prone PCR conditions, can be chosen to reduce polymerase fidelity to introduce additional mutations, particularly substitutions. The primer binding site can be in the self-complementary region of the hairpin.

In one embodiment, two different hairpin nucleic acids are added. In another embodiment, a single hairpin nucleic acid is added, e.g., to one or both termini.

A shuffled nucleic acid can be amplified by a variety of methods in addition to PCR (U.S. Pat. Nos. 4,683,196 and 4,683,202). Such other methods include rolling circle amplification ("RCA," U.S. Pat. No. 5,714,320), isothermal RNA amplification or NASBA, and strand displacement amplification (U.S. Pat. No. 5,455,166).

Aptamer Formation

The formation of nucleic acid aptamers from double stranded DNA is facilitated by the use of a single hairpin nucleic acid. Because one end of each individual PCR product is complementary to its other end in this embodiment, denaturation of the products can results in the formation of a monomeric single-stranded DNAs that is stabilized by a duplex region formed by the annealed ends. For example, the amplified double stranded DNA can be purified and resuspended in pure water, denatured at 95° C. and cooled rapidly in order to favor aptamer formation over duplex formation.

Additional methods are available for efficient aptamer formation. For example, the amplification primer (e.g., primer annealing to the ligated hairpin) can include a moiety for attachment to a solid support. Amplification products can be bound, e.g., by oxidation of a thiol or a non-covalent linkage such as biotin-avidin, to a solid support, e.g., a planar surface, a matrix, or a bead, at a concentration that only one strand of the amplification product can be stably attached. Denaturation of bound amplification products (e.g., separates the strands of each duplex amplification product from unbound strand which can be removed by a wash). Renaturation of bound strands produces in monomeric nucleic acid aptamers.

In another example, RNA copies of the shuffled nucleic acid strand are produced, e.g., using a T7 polymerase promoter that can be attached to the shuffled nucleic acid, e.g., by ligation. The RNA copies can be used as aptamers themselves, or can be reverse transcribed to produce DNA aptamers and then the RNA templates removed using a ribonuclease.

Structural features of nucleic acid aptamers formed from shuffled nucleic acid can include variously positioned regions of self-complementarity. These features can stabilize the folded conformation of an aptamer. Since the random ligation can result in the inclusion of two copies of a fragment of a parent strand, one copy in each orientation, an aptamer formed from a single strand of the shuffled nucleic acid can include the nucleic acid fragment and its complement. This internal complementarity can promote the formation of secondary structures. These secondary structures are known to be critical to the binding and catalytic abilities of nucleic acids, e.g., by offsetting some of the entropic cost of intramolecular folding (Hermann and Patel. *Science* 2000, 287, 820-5; Scott. *Curr Opin Struct Biol* 1998, 8, 720-6; Sen and Geyer. *Curr Opin Chem Biol* 1998, 2, 680-7.). Libraries of nonhomologously recombined, single-stranded DNAs formed in this fashion are ready for in vitro selection.

In another implementation, the ligation step of the method is further enriched by the inclusion of synthetic double-stranded nucleic acids that include sequence features useful for aptamer functionality. Such sequences include sequences which as single-stranded nucleic acids would form tetraloops, bulges, or hairpins. By including such sequences during the ligation phase, these features are interspersed with fragments from the parental nucleic acids.

Screening Aptamers

Aptamers are easily screened as untagged molecules in vitro since a selected aptamer can be recovered by standard nucleic acid amplification procedures. The method can be enhanced, e.g., in later rounds of selection, by splitting selected aptamers into pools and modifying each aptamer in the pool with a detectable label such as a fluorophore. Pools having aptamers that functionally alter the properties of the label can be identified. Such pools can be repeatedly split and reanalyzed to identify the individual aptamers with the desired properties (see, e.g., Jhaveri et al. *Nature Biotechnol.* 18: 1293).

In addition, aptamers can be screened for activity in vivo. For example, shuffled nucleic acids can be cloned into an expression vector that is introduced into cells. RNA aptamers resulting from the expressed shuffled nucleic acids can be screened for a biological activity. Cells having the activity can be isolated and the expression vector for the selected RNA aptamer recovered.

Non-Specific Nucleic Acid Cleavage

A variety of methods can be used to fragment parent nucleic acid strands for the nucleic acid shuffling method described here. The parent strands can be digested at random location by an enzyme or a chemical reagent. For example, the chemical reagent can be o-phenanthroline-copper or a hydroxyl radical generator such as Fe(II)-EDTA-hydrogen peroxide. The enzyme can be an endonuclease, such as DNaseI, or an exonuclease. In some implementations, the parent nucleic acid coiled around nucleosomes or another structure to facilitate the digestion (e.g., by DNaseI) of the parent nucleic acid into fragments of regular size, e.g., a length of about 70 to 120 nucleotides.

In another implementation, the parent strands are digested at frequent non-random locations, e.g., using one or more site-specific restriction enzymes such as a 4-base pair cutter, a 6-base cutters, or a pool of such enzymes.

The parent nucleic acid strand can be random synthetic nucleic acid, genomic nucleic acid, a gene or sequence of interest, or a pool of such sequences. For example, a pool of sequence can be a collection of sequence obtained from a previous round of shuffling and selection.

Non-Coding Ribonucleic Acid

In one aspect, the invention pertains to using non-homologous random recombination (NRR) to create a diverse population of non-coding ribonucleic acid molecules, also known as small non-translated RNAs (sRNAs) regulate a variety of biological processes and are abundant in nature (Lagos-Quintana, et al. (2001) Science 294: 853-858; Lau, et al. (2001) Science 294: 858-862; Huttenhofer, et al. (2001) Embo J 20: 2943-2953; Argaman, et al. (2001) Curr Biol 11: 941-950; Hershberg, et al. (2003) Nuc. Acids Res 31: 1813-1820; McCutcheon, et al. (2003) Nuc. Acids Res 31: 4119-4128; Zhang, et al. (2003) Microbiol 50: 1111-1124; and Wassarman, (2002) Cell 109: 141-144). Thus, the present invention provides a simple, and effective diversification method that effects the rapid deletion, repetition, and reordering of subsequences, for the directed evolution of nucleic acids, such as DNA aptamers, sRNAs, and proteins such as protein enzymes with new functional or structural properties.

Small RNA or non-translated RNA, most of which are found in bacterial intergenic regions and eukaryotic introns, regulate a variety of biological process. Regulation by small RNA (sRNA, ~100-200 nucleotides long) are now being mechanistically studied to understand how these RNAs function. In prokaryotes, sRNAs regulate such processes as the transition from growth to stationary phase, quorum sensing and virulence. In some cases, the target of the sRNA is known. A major class of sRNAs act by binding to the RNA chaperone Hfq, followed by pairing to specific target mRNA. This pairing results in the stimulation or inhibition of translation and in mRNA.

Hfq mediates interactions between small, regulatory RNAs and specific messenger RNA (mRNA) targets. These interactions typically alter the stability of the target transcripts. The Hfq protein has multiple functions in cellular physiology. Most data on Hfq-RNA interactions stem from studies on small E. coli RNAs. Hfq binds to OxyS, DsrA, RprA, RyhB, and Spot42 RNAs, as well as to other sRNAs. Some sRNAs are involved in translational regulation, and Hfq has been suggested to facilitate their interaction with target mRNAs. Hfq stimulates both the interaction of spot42 RNA with galK mRNA and that of OxyS with fhlA mRNA (Zhang, et al. (2002) Mol Cell 9: 11-22). RyhB RNA, which is negatively controlled by Fur, seems to down-regulate iron storage as well as iron-containing proteins, and thereby has an important function in establishing priorities in iron usage. DsrA stimulates and represses translation of the E. coli rpoS and hns mRNAs (Lease, et al. (1998) Proc Natl Acad Sci USA 95: 12456-12461), respectively, and Hfq has been shown to be necessary for DsrA-mediated regulation of both rpoS and hns.

About 50 of the sRNAs have been identified in E. coli, however, only a small subset of these have been well characterized (Wassarman, (2002) Cell 109: 141-144; Eddy (2001) Nature Reviews Genetics 2: 919-929; Gottesman, (2002) Genes & Development 16: 2829-2842; and Storz, (2004) Curr Opin Microbiol 7: 140-144). The sequence and structural diversity of sRNAs together with the relatively small number of well-understood examples can make their study difficult, creating the need for additional methods to dissect sRNA structure and function.

The central regulator of the general stress response in E. coli is the protein sigma factor RpoS. During normal growth conditions, RpoS protein levels remain low until stationary phase even though rpoS mRNA levels remain constant and abundant (Brown, et al. (1997) J Bacteriol 179: 656-662; and Hengge-Aronis, (2002) Microbiol. Molec. Biol. Rev. 66: 373-395). The rpoS mRNA contains a 567 nucleotide 5' untranslated region (UTR) proposed to fold into a structure in which the translation initiation region is base-paired, repressing translation in cis. Expression of RpoS is dependent on the RNA chaperone protein, Hfq, and translation of the rpoS message is regulated by many different factors, including several sRNAs (Brown (1997) Supra and Hengge-Aronis (2002) Supra).

DsrA and OxyS are two E. coli sRNAs that activate and repress, respectively, the translation of rpoS, which encodes a protein sigma factor. Due to their structural complexity, the functional dissection of sRNAs solely by designing and assaying mutants can be challenging. the methods of the invention describe a complementary approach to the study of sRNAs in which highly diversified sRNA libraries are generated using nonhomologous random recombination (NRR) and processed efficiently by in vivo selections that link sRNA activities to cell survival. When applied to DsrA and OxyS, this approach rapidly identified essential regions of both sRNAs not previously implicated in their function. Resulting hypotheses about DsrA and OxyS function were tested and further refined experimentally. The findings demonstrate a NRR- and selection-based approach to the study of natural functional nucleic acids.

DsrA, an 85 nucleotide sRNA induced at low temperatures, activates translation by interacting with the rpoS 5' UTR through a proposed anti-antisense mechanism (Sledjeski, et al. (1995) Proc Natl Acad Sci USA 92: 2003-2007; Sledjeski, et al. (1996) Embo J 15: 3993-4000; Majdalani, et al. (1998) Proc Natl Acad Sci USA 95: 12462-12467; Lease, et al. (2000) Proc Natl Acad Sci USA 97: 9919-9924; and Lease, et al. (1998) Proc Natl Acad Sci USA 95: 12456-12461). DsrAis thought to fold into three stem-loops (SL1, SL2 and SL3) with an AU-rich SL1-SL2 linker (Lease et al. (2000) Supra). Based on previous studies, it has been proposed that SL1 and the SL1-SL2 linker form an intermolecular duplex with the rpoS mRNA, freeing the translation initiation region for binding by the ribosome. SL3 has been proposed to be a rho-independent transcriptional terminator (Lease, et al. (2000) Supra; Lease, et al. (1998) Supra).

OxyS, a 109 nucleotide sRNA transcribed in response to oxidative stress, represses rpoS translation through an unknown mechanism (Altuvia, et al. (1997) Cell 90: 43-53; Zhang, et al. (1998) Embo J 17: 6061-6068; and Altuvia, et al. (1998) Embo J 17: 6069-6075). Although unrelated in sequence to DsrA, OxyS is also predicted to fold into three stem-loops (Zuker, et al. (2003) Nucl. Acids Res 31: 3406-3415). The linker between SL2 and SL3 has been shown to be important for OxyS activity (Zhang, et al. (1998) Supra), and SL3 of OxyS also appears to act as a transcriptional terminator (Altuvia, et al. (1998) Supra). Regulation of rpoS by DsrA and OxyS is dependent upon the Hfq; the RNA-binding protein most likely mediates initial interactions between sRNA and mRNA (Sledjeski, et al. (2001) Bacteriol 183: 1997-2005; Zhang, et al. (2002) Mol Cell 9: 11-22; and Moller, et al. (2002) Mol Cell 9: 23-30).

The existence of two sRNAs that target the same message but induce opposite outcomes highlights the complexity and functional potential of these systems. To further the understanding of sRNA translational regulators, the sequence requirements for sRNA regulation of rpoS expression was investigated. It was reasoned that selecting libraries of highly diversified DsrA or OxyS variants for rpoS activation or repression would efficiently identify essential and nonessential regions of both sRNAs in a manner that is independent of current assumptions.

The invention relates to the use of NRR to functionally dissect a natural nucleic acid. NRR was use with selections in *E. coli* cells to isolate highly diversified yet functional sRNA activators or repressors of rpoS translation starting from dsrA or oxyS. This approach rapidly identified essential regions of both sRNAs not previously implicated in their function. In addition, a region of DsrA previously thought to be important for translational activation was found to be unnecessary for this activity, although possibly involved in increasing the stability of DsrA. These findings provide new insights into the mechanisms of translational regulation of rpoS and suggest that the use of NRR coupled with in vivo selection or high-throughput screening may prove valuable to the study of other functional RNAs.

Sequence Minimization

The nucleic acid shuffling method can be used to minimize a biological sequence, e.g., for characterization to identify essential features. The essential features can be adapted for use in engineered sequences. For example, the method can be used to minimize a nucleic acid aptamer or a polypeptide by minimizing the coding nucleic acid.

One additional example is the minimization of transcriptional regulatory regions. Regulatory genomic DNA is fragmented and relegated using the shuffling method described here. The shuffled nucleic acid strands are cloned upstream of a promoter in a eukaryotic expression vector having a reporter gene such as green fluorescent protein operably linked to the promoter and upstream regulatory sequences. These reporter vectors bearing the cloned shuffled nucleic acid are transformed into host cells. Individual transformants are analyzed for activation or repression of the reporter gene under the desired condition, e.g., exposure to a therapeutic drug, a hormone, a cytokine, and so forth. Transformants with desired properties are isolated, and the shuffled nucleic acid is sequenced and characterized. The shuffled nucleic acid can be used to generate expression vectors that are triggered by the desired conditions. Such constructs are particularly useful for the design of novel genetic circuits (see, e.g., Gardner et al. (2000) *Nature* 402: 339; and Becskel & Serrano et al. (2000) *Nature* 405: 590).

Sequence Enrichment

The nucleic acid shuffling method described here can be used to enhance a biological sequence, e.g., to provide additional features which confer additional or new properties, e.g., increased stability, regulation by an allosteric effector, increased affinity or enzymatic properties. For example, the method can be used breed a hybrid nucleic acid aptamer from two parent nucleic acid aptamers with different properties. Hybrid nucleic acid aptamers can be identified, for example which catalyze a reaction similar to one parent, but are also allosterically regulated by a ligand bound by another parent.

Sequence Analysis

The methods described herein can be coupled with sequence analysis. For example, if multiple evolved clones are selected, they can be compared to identify a segment that recurs among the clones. Such segments may represent functional or structural motifs useful for the selected property. Similarly, if a single sequence is minimized, the reoccurrence of a segment can also be indicative of its functional or structural importance. The methods can include inferring from a plurality of clones selected for a criterion, one or more valued segments. Rational design can be used to produce small nucleic acids that include the valued segments. In another embodiment, the valued segments are inserted into another shuffling reaction, e.g., to evolve a multi-functional nucleic acid sequence.

The program MACAW (Multiple Alignment Construction and Analysis Workbench), available from the National Center for Biotechnology Information (Bethesda Md., USA) can be used to compare selected clones and identify a recurring segment.

Without further elaboration, it is believed that the above description has adequately enabled the present invention. The following examples are, therefore to be construed as merely illustrative, and not limitative of the remainder of the disclosure in any way whatsoever. All publications cited herein are hereby incorporated by reference in their entirety.

II. Evolved Proteins and Polypeptides

In still another aspect, the invention features a method of generating a library of altered polypeptides. The method includes: providing a parent nucleic acid strand encoding a parent polypeptide; fragmenting the parent nucleic acid strand to generate at least two, preferably three or more, nucleic acid fragments, each nucleic acid fragment having a terminus that can be ligated to at least one non-adjacent fragment; ligating at least a subset of the nucleic acid fragments to generate a plurality of shuffled nucleic acid strands, wherein the shuffled nucleic acid strands have at least one nucleic acid fragment inserted, deleted, or rearranged; and expressing a shuffled polypeptide encoded by the shuffled nucleic acid strand. The fragmenting can be such that the parent nucleic acid strand is fragmented by a non-site specific agent (e.g., a non-specific endonuclease), and/or the average size of the fragments is less than 2000 nucleotides. The shuffled nucleic acids is used to create a library of plasmids for protein expression and selection. In another embodiment, the methods of the invention can be used to create a chimeric polypeptide, or a library of chimeric polypeptides.

The method described here can be used to shuffle polypeptide sequences. A nucleic acid strand encoding a polypeptide is used as the parent sequence. The coding strand is fragmented as described, and the fragments are relegated to form shuffled nucleic acid coding sequences. Although a significant fraction of such sequences may contain in-frame stop codons, within a large library a reasonable proportion of sequence still include a substantial polypeptide coding region. For each ligation of two segments, only one of six products is expected to contain an in-frame ligation of the two segments. A library of $10^{10}$ shuffled sequence that include five fragments still includes about $10^6$ in-frame shuffled coding sequences. Such a population is a substantial pool from which to identify diversified sequences. Moreover, the size of the fragments used for constructing shuffled polypeptide coding nucleic acids can be at least approximately 200, 300, 400, 500, 600, 700, 800, 1000, 1200 or 1400 nucleotides.

The shuffling of coding nucleic acid sequences can also be enriched by the inclusion of synthetic sequences such as randomized amino acid sequences, patterned amino acid sequence, computer-designed amino acid sequences, and combinations of the above. Particularly useful are synthetic sequences that encode peptides with functional properties or with particular structural propensities. For example, β-strands can be encoded by a degenerate oligonucleotide in which codons for hydrophobic residues, e.g., codons [GAC]-[T]-[N], are alternated with codons for hydrophilic residue, e.g., codons [GTC]-[A]-[N], from a degenerate can encode artificial amino acid sequences. Similarly amphipathic α-helices can be patterned based on the helical pitch of the canonical α-helix. Cho et aL. (2000) *J Mol Biol* 297:309-19, for example, describes methods for preparing libraries of randomized and patterned amino acid sequences. Other functional sequence which can be included are sequences which encode cysteine, serine, and/or histidines; and sequences found in a database of motifs, e.g., ProSite.

In one particular embodiment of polypeptide shuffling, the parental coding nucleic acids are not fragmented randomly. Rather, individual structural domains are amplified from the parental coding nucleic acids, e.g., amplifying multiple signal transduction modules from eukaryotic cDNA using a large number of specific primers. The primers are designed such that all the domains are in the same frame. The amplified fragments are then ligated together randomly to generate shuffled coding nucleic acids. The library of shuffled nucleic acid can be screened (see below), e.g., in cells for novel signal transduction circuits.

The method can, for example, be used to screen for polypeptide variants with higher thermal stability. Such variants can be generated in a number of ways. One possibility is the duplication and/or rearrangement of a structural feature induces domain-swapping and oligomerization of the polypeptide. Such evolutionary events may also have occurred under natural conditions (Bennett et al. *Protein Sci.* 1995:2455-68).

To determine the "percent identity" of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes) using the Needleman and Wunsch ((1970) *J. Mol. Biol.* 48:444-453) algorithm which has been incorporated into the GAP program in the GCG software package, using a Blossum 62 scoring matrix, a gap penalty of 12, a gap extend penalty of 4, and a frameshift gap penalty of 5. The percentage of identical nucleotides is determined from the optimal alignment.

The shuffled nucleic acid coding regions can be used to express evolved polypeptides that are displayed as RNA fusions (Roberts and Szostak *Proc Natl Acad Sci USA*. 1997 94:12297-302; PCT WO 98/31700), on chips (PCT WO 99/51773), on bacteria (Ladner, U.S. Pat. No. 5,223,409), on spores (Ladner U.S. Pat. No. 5,223,409), on plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.). The displayed polypeptide can be selected for functional properties, e.g., for binding to a ligand such as a target molecule or a transition state analog.

The shuffled nucleic acid coding regions can also be used to express evolved polypeptides in cells. The cells can have an altered genetic composition, e.g., in order to provide a selective environment suitable for identifying expressed evolved polypeptides having a particular activity (Joo et al. (1999) *Nature* 399: 670-673).

The shuffled nucleic acid coding regions can be inserted into a two-hybrid vector, e.g., so that the expressed evolved polypeptide is fused to a nucleic acid binding domain or to a transcriptional activation domain (see, e.g., U.S. Pat. No. 5,283,317). The vector with the cloned shuffled coding region can be inserted into a cell have a corresponding two-hybrid vector expressing a target polypeptide. Evolved polypeptides which bind the target polypeptide activate transcription and can be readily identified for characterization and additional rounds of selection.

Protein Structural Elements

The protein structural elements in the evolved polypeptides include, but are not limited to, alpha helix, beta sheet, alpha-beta structure, alpha-loop structure, beta-loop structures, and various combinations thereof. These structural elements may be present in various configurations and patterns, such as helical bundles, up-and-down beta barrels, alpha/beta barrels, and alpha/beta sheet structures.

(a) Alpha-Helix

The alpha-helix is the most common form of secondary structure with approximately 31% of all residues in proteins participating in alpha-helices. The helix has 3.6 residues per turn and is stabilised by hydrogen bonding between the backbone carbonyl oxygen of one residue and the backbone NH of the fourth residue along the helix. Amino acids in ideal alpha-helices have phi & psi angles of approximately −60° and −50°. Although both right-hand and left-hand alpha-helice are found in proteins, the vast majority are right-handed as they have more favourable steric interactions between amino acid side chains.

Most proteins exist in an aqueous environment (with the exception of membrane proteins) and it is a general rule of protein structure that proteins have hydrophobic cores. In proteins, alpha-helices interact in such a way that the hydrophobic areas form hydrophobic interactions with each other, and the hydrophilic areas are exposed to the solvent. Certain amino acids have a distinct preference for alpha-helices. Alanine, glutamic acid, leucine and methionine are good helix formers, whereas proline, glycine, tyrosine and serine are helix-breaking residues.

(b) Beta-Sheets

The second most common element of secondary structure in proteins is the beta-sheet. A beta-sheet is formed from several individual beta-strands which are distant from each other along the primary protein sequence. Beta-strands are usually 5-10 residues long and are in a fully extended conformation. Phi & psi angles occupy a wide range of values in the fully allowed region of the Ramachandran plot. The individual strands are aligned next to each other in such a way that the peptide bond carobonyl oxygens hydrogen bond with neighbouring NH groups. In this way a concerted hydrogen bonding network is built up.

Two types of connection topology are seen in beta sheets. The most stable is the antiparallel beta sheet. In antiparallel sheets, the beta-strans are connected sequentially. Parallel beta-sheets are less stable due to the hydrogen bonds not being optimally aligned. Parallel sheets are formed from segments of peptide backbond distantly connected by other types of secondary structure. In a beta-sheet, the amino acid side-chains of successive residues project alternately from either side of the beta-sheet. It is common to find one side of the sheet predominantly hydrophobic and one side hydrophillic. In proteins such hydrophilic faces frequently make contact via hydrophobic bonds.

(c) Loops

Elements of secondary structure such as alpha-helices and beta-strands or sheets are connected to each other by segments of polypeptide forming loops. In generic terms, the helices and sheets form the stable hydrophobic core of the protein. The connecting loops are to be found on the surface of the structure. As they are solvent exposed, they are rich in polar and charged amino acids which hydrogen bond to solvent water molecules as opposed to participating in concerted hydrogen-bonding patterns.

(d) Random Coil

Random coil is the term used for segments of polypeptide chain that do not form regular secondary structures. Such conformations are not really random: they are the result of a balance of interactions between amino acid side chains and solvent and interactions between side-chains. The predominant hydrogen bonding pattern in random coils is between polypeptide and water, concerted hydrogen bonding networks are absent.

EXAMPLES

Example 1

Shuffled Library Construction

The steps of the method for non-homologous recombination were successfully executed and analyzed. Two shuffled nucleic acid libraries were produced.

Library A. This library is a library of shuffled human genomic sequences. Human genomic DNA was digest with DNase I in the presence of divalent magnesium. Human genomic DNA was selected, in part, for its increased secondary structure content relative to purely random DNA. Size selection of the fragments was achieved by modulating the duration of the digestion followed by gel purification. Conditions were selected such that the average fragment size ranged from 10 to 100 base pair (pb) as required. The fragments were then treated with T4 DNA polymerase, which generates blunt ends by filling in 5' overhangs and degrading 3' overhangs.

Library B. This library is a library of shuffled random synthetic sequences. Random 40-mer oligonucleotides were synthesized and enzymatically 5'-phosphorylated with T4 polynucleotidyl kinase. The oligonucleotides were treated with T4 DNA polymerase which extended annealed and partially annealed oligonucleotides into double stranded DNA.

Both libraries were prepared as follows. Treatment of the blunt-ended fragment pool with T4 DNA ligase to effect nonhomologous recombination resulted in an increase in the average molecular weight of approximately a factor of two. This extent of ligation may result from intramolecular ligation events that are prematurely terminating such as end joining and circular dead-end products of approximately 100-200 bp.

More extensive nucleic acid shuffling was achieved by modification of the ligation conditions. Polyethylene glycol (PEG) was added to the fragment ligation reactions in order to increase the frequency of intermolecular ligations. At a final concentration of 15% PEG, the nearly exclusive intermolecular ligation of the blunt ended DNA fragments was observed, unexpectedly generating products more than 10,000 bp in length.

DNA hairpins were designed to terminate the ligation process and install defined sequences on the ends of the library members. Two versions of this hairpin are formed by the exemplary sequences listed as follows:

(SEQ ID NO: 1)
5'-GGGAATTCTAGAAGCTTCCCGGGGGGCCCGCGCGGGCCCCCGGGAA
GCTTCTAGAATTCCC-3'

The above hairpin includes sites for EcoRI, HindIII, XbaI, and SmaI.

(SEQ ID NO: 2)
5'-GGGTCCGGATACGAATTCCCCGGGGGCCCGCGCGGGCCCCCGGGGAA
TTCGTATCCGGACCC-3'

The above hairpin includes sites for BspE1, BciVI, EcoRI, and SmaI.

The second version of the hairpin (SEQ ID NO:2) can be removed in a "scarless" manner from the library by digestion with the Type IIS restriction enzyme, BciVI, digestion, followed by treatment with T4 DNA polymerase. The Type IIS recognition site is located such that cleavage precisely removes the hairpin precisely from the shuffled nucleic acid strands. The other version of the hairpin (SEQ ID NO:1) does not include a Type IIS restriction site.

Both hairpin sequences included a variety of Type II restriction sites in their self-complementary regions. For example, the exemplary hairpins above included several restriction endonuclease sites flanked on the closed end by a SmaI cleavage site and on the open end by half of a SmaI site. Hairpin dimers formed during the ligation process are conveniently destroyed by digestion with SmaI. Such digestion avoids forming undesired products during subsequent PCR steps. Other restriction enzymes were used for cloning and mapping.

Addition of 2-25 mol % of these adapter hairpins to the PEG-promoted intermolecular ligation reactions terminated the ligation events. The average length of the ligation products was inversely dependent on the concentration of adapters, consistent with their proposed role in terminating end joining. This feature enables the selection application of evolutionary pressure for minimizing or extending the length of a functional nucleic acid. Digestion of this material with SmaI removed the closed ends of each library member facilitating denaturation during PCR and also destroyed undesired hairpin dimers, i.e., hairpin oligonucleotides that ligate to each other without including any shuffled nucleic acids.

PCR of the resulting recombined, double-stranded DNA using a single 21-base primer matching one arm of the adapter hairpin (the "adapter primer") produced a product pool. The average size of the pool related to the ratio of hairpin DNA included in the ligation (e.g., in one case~200 bp). The shuffled nucleic acid with ligated hairpins at both ends could also be successfully amplified using error prone PCR.

The amplified double-stranded shuffled nucleic acids were then denatured to form individual DNA aptamers, each aptamer formed from a single nucleic acid strand. A variety of conditions using low salt concentrations, metal chelators, and hydroxide were tested for their ability to efficiently melt the double stranded products into single strands. It was found that simple heating at 94° C. in very pure water followed by rapid cooling and addition of desired buffer afforded the most reproducible and high yielding DNA aptamer formation. These conditions favored the folding of aptamers over the renaturation of double-stranded DNA. Aptamers were distinguished from canonical double-stranded DNA by their decreased molecular weight as assayed by agarose gel electrophoresis.

Aptamer generation under these conditions to the PCR amplified shuffled nucleic acid libraries was favored relative to denaturation of an arbitrary 400-mer. This observation is consistent with the formation of secondary structure resulting from the intramolecular annealing of the perfectly complementary 21 bases at the end of each library member. These single-stranded, nonhomologously recombined DNA libraries were then available for in vitro selections.

Example 2

Evolution of New DNA Receptor for cAMP

Several rounds of diversification using the shuffling method described here are used to evolve DNA receptors capable of binding cyclic AMP (cAMP). Initial diversity was obtained by using the two libraries, library A and B above. Each library (100 µg for round 1 and 10 µg for subsequent rounds) of ~$10^{15}$ shuffled DNAs was dissolved in buffers containing 50 mM Tris pH 8.0, 150 mM NaCi, and varying concentrations of divalent magnesium, manganese, and zinc cations (initially 10 mM, 1 mM, and 10 µM, respectively). The library was loaded onto a column of resin-bound cAMP and washed extensively with buffer. Bound DNAs were eluted with buffer containing 1 mM free cAMP. Stringency between rounds was increased by lowering the concentration of divalent cations and increasing the speed of loading and eluting the resin (thus applying selective pressure for superior on-rate kinetics). Recovered library members were amplified by PCR with the adapter primer, digested with BciVi or EcoRI to remove the adapter, and then either cloned into pBR322 for DNA sequencing or passed on to the next round of diversification. Evolutionary pressure to specifically bind cAMP can be introduced by washing the resin-bound library members with cGMP, cIMP, AMP, and other nucleoside analogs. After two rounds of selection, a pool of enriched sequences was obtained for further analysis and selection.

Example 3

Evolution of a DNA Receptor for Avidin

The method is used to evolve a DNA aptamer that can bind to avidin with high affinity and be released by biotin, thereby providing a DNA analog that can function in place of biotin.

For this example, a side-by-side comparison the results of using error-prone PCR versus NRR to evolve DNA aptamers that bind streptavidin. Starting with two parental sequences of modest avidin affinity, evolution by NRR resulted in avidin aptamers with 5- to 8-fold higher affinity ($K_d$=~14 nM) than those evolved by error-prone PCR. In addition to evolving more potent function than error-prone PCR, NRR also greatly facilitates the identification of critical regions within evolved sequences. Inspection of a small number of NRR-evolved clones rapidly identified a 40-base DNA sequence that possesses streptavidin binding activity. Non-homologous random recombination (NRR) enhances the effectiveness of nucleic acid evolution and facilitates the identification of structure-activity relationships among evolved sequences.

A DNA-based streptavidin binding aptamer was successfully minimized as determined, both by inspection of NRR-evolved sequences and, independently, by controlling the size of the recombined molecules during the NRR process.

The approach of this example includes the following features. First, the approach favors intermolecular ligation. In contrast, the simple addition of DNA ligase enzymes to double-stranded, blunt-ended fragments tends to result in intramolecular circularization rather than intermolecular ligation. Second, the approach constructs defined sequences at the ends of the fragments. These defined sequences serve as primer binding sites for PCR amplification following selection. Third, the size of recombined products is controlled since sequences that are too large can be difficult to analyze or amplify, and those that are too small may not be able to fold into secondary structures with optimal desired properties.

(1) Experimental Procedure (a) Preparation of NRR Variants

Primer oligonucleotides were synthesized by standard automated phosphoramidite coupling methods and purified by reverse-phase HPLC. Hairpin oligonucleotides and random oligonucleotides for the initial pool were purchased from Sigma Genosys (Houston, Tex.). Agarose gels were stained with ethidium bromide and visualized with UV light. DNA quantitation was performed by UV spectrophotometry and by gel electrophoresis, staining, and densitometry. Quantitation of radioactivity for binding assays was performed by phosphorimager (Molecular Dynamics), and binding curves were fit using Microsoft Excel. Restriction endonucleases, T4 DNA ligase, Vent DNA polymerase, T4 polynucleotide kinase, and T4 DNA polymerase were obtained from New England Biolabs (Beverly, Mass.). Polymerase chain reactions were performed using Taq PCR Mastermix from Promega (Milwaukee, Wis.), on a PTC-200 thermal cycler (MJ Research, Waltham, Mass.). Individual sequences were cloned using the TOPO TA cloning kit from Invitrogen (Carlsbad, Calif.).

Hairpin and Primer Sequence

Hairpin/primer sets were changed occasionally to avoid contamination and had no significant impact on the average streptavidin affinity of evolving pools. Contamination was monitored during each PCR reaction with a negative control reaction lacking added template DNA.

hairpin 1:

(SEQ ID NO:3)
5'-phosphate-CTGTCCGGATACAAGCTTCAGCTGGGCCCGCGCGGGC
CCAGCTGAAGCTTGTATCCGGACAG-3'

(SEQ ID NO: 4)
primer 1: 5'-CTGAAGCTTGTATCCGGACAG-3', hairpin 2:

(SEQ ID NO: 5)
5'-phosphate-CCTCCGCGGCATCCGAATTCAGGCCTCCGGGCGCCCG
GAGGCCTGAATTCGGATGCCGCGGAGG-3'

(SEQ ID NO: 6)
primer 2: 5'-CCTGAATTCGGATGCCGCGGAGG-3'

Double stranded $N_{40}$ construction: 5 nmol template (5'-GCCCCGCGGATGGGACGTCCC-$N_{40}$-CGCCCGCG-GCATCCGACGTCCC-3' (SEQ ID NO: 7) and 5 nmol of primer (5'-GGGACGT CGGATGCCGCGGGCG-3' (SEQ ID NO: 8) were annealed and extended with Vent DNA polymerase (94° C. for 2 min 30 s, 65° C. for 30 s, add polymerase, 75° C. for 1 h). The 83 bp product was digested with Fok I to remove the ends and the resulting 40 bp product was purified by gel electrophoresis on a 3% agarose gel. The purified material was treated with T4 DNA polymerase to create blunt ends and purified by gel filtration (Centrisep columns, Princeton Separations). The 40 bp blunt-ended product was quantitated by densitometry on a 3% agarose gel.

Initial Pool 57 pmol double stranded $N_{40}$ was ligated to 57 pmol hairpin 1 under intermolecular blunt ligation conditions (15% PEG 6000, 50 µM ATP in NEB T4 DNA ligase buffer (-ATP) using 120 Weiss units of T4 DNA ligase, 25° C., 1 h.) This ratio The PCR products were extracted with 1:1 phenol:chloroform and ethanol precipitated to yield a library of approximately $5 \times 10^{14}$ molecules with an average size of 250 bp was empirically determined to give products averaging 250 bp. The products were digested with Pvu II to remove the hairpin ends. The resulting fragments were amplified under error-prone PCR conditions in 9.6 mL (94° C. for 2 min 30 s, then cycled 40 times at 94° C. for 30 s, 60° C. for 30 s, 72° C. for 1 min 10 s).

Fragmentation of Sequences for Nonhomologous Random Recombination

PCR amplified products were digested with the appropriate type IIS restriction endonuclease (BciV I for primer 1 or Fok I for primer 2) to remove the primer ends. Alternatively, if the sequence of an individual clone was known, primers were synthesized to PCR amplify the sequence without the hairpin ends. The resulting fragments were digested with DNase I (Sigma), in 10 M $MgCl_2$, 20 mM Tris-Cl pH 8.0 for 1 to 5 minutes at room temperature using approximately 2 μL of a 1:1000 dilution of DNase I. The digestions were monitored by agarose gel electrophoresis. When the size of fragments reached the desired average, the reaction was extracted with phenol-chloroform and exchanged into T4 DNA polymerase buffer by gel filtration. The fragments were blunted with T4 DNA polymerase, phenol-chloroform extracted, and purified by gel filtration. Fragments of the desired size range were purified on a 3% agarose gel and exchanged into T4 ligase buffer (see below) by gel filtration. The resulting pieces were quantitated by densitometry on a 3% agarose gel.

Ligation with Hairpin

Blunt-ended pieces were ligated with hairpin 1 or hairpin 2 at a ratio empirically determined to generate the desired product length (typically this was similar to the theoretically calculated stoichiometry). For fragments of 50 bp average length, the ratio of 2:1 fragments:hairpin generated an average ligated product of 200 bp. Ligations were performed under intermolecular blunt ligation conditions (15% PEG 6000, 50 μM ATP in NEB T4 DNA ligase (-ATP) buffer with T4 DNA ligase, 25° C., 1 h) The ligations were extracted with phenol-chloroform and ethanol precipitated then digested with the appropriate restriction enzyme to remove the hairpin ends (Pvu II for hairpin 1 or Stu I for hairpin 2).

PCR Amplification

Digested ligation products were amplified by PCR using Promega Mastermix and the appropriate primer (primer 1 for hairpin 1 or primer 2 for hairpin 2) at 1 μM. PCRs were initially denatured at 94° C. for 2 min 30 s, then cycled 40 times. Hairpin 1 PCRs were cycled as follows: 94° C. for 30 s, 60° C. for 30 s, 72° C. for 30 s. Hairpin 2 PCRs were cycled as follows: 94° C. for 30 s, 72° C. for 1 min 30 s. All PCRs were completed with a final 10 min extension at 72° C.

(b) In vitro Selections

For the three rounds of in vitro selection of the random library to generate clones including S3-13 and S3-16, the initial pool was denatured by heating to 95° C. in deionized water (Millipore) for 5 min and chilling suddenly on ice. Buffer was added to a final composition of 150 mM NaCl, 50 mM Tris-Cl pH 8.0, 10 mM $MgCl_2$ ("binding buffer") Streptavidin-agarose (0.5 mL of a 50% suspension, Sigma) was prepared by pre-washing with binding buffer in an HR5-5 column (Amersham-Pharmacia Biotech). The library was passed through the column followed by 56 mL of binding buffer. Desired sequences were eluted by washing the column with 0.25 mg free streptavidin (Sigma) in 0.5 mL binding buffer, followed by another 1.5 mL of binding buffer. The elution was extracted with phenol-chloroform and ethanol co-precipitated with 5 μg glycogen, and the resulting selected DNA molecules were amplified by PCR as above. For the in vitro selection of sequences starting with parents S3-13 and S3-16 (using libraries diversified by error-prone PCR or NRR), the library and streptavidin-agarose were shaken for one hour in 1 M NaCl, 50 mM Tris-Cl pH 8.0, 5 mM $MgCl_2$ ("stringent buffer") at a final concentration of 1 nM for both DNA ahd streptavidin. The mixture was loaded into an HR5-5 column and washed with 50 mL stringent buffer. Desired DNA molecules were eluted by shaking the washed beads with 0.125 mg free streptavidin in 0.9 mL stringent buffer at 25° C., 30 min. The elution was extracted with phenol-chloroform and ethanol precipitated with glycogen, and the resulting DNA was amplified by PCR as above.

(c) Binding Affinity Assays

Affinities for streptavidin were measured using a radioactive filter binding assay. Pools or individual clones were amplified by PCR. One pmol was radiolabeled with 15 units T4 PNK and 10 μCi $\gamma$-$^{32}P$ ATP (NEN) in T4 PNK buffer at 37° C., 1 h. Labeled DNA was extracted twice with phenol-chloroform and purified twice by gel filtration to remove ATP. The DNA was then denatured in water at 95° C. for 5 min together with 2 μg human genomic DNA (to block nonspecific DNA binding) per 5 fmol labeled DNA, and chilled in ice water for 5 mins. 5 fmol of labeled DNA plus 2 μg unlabeled human genomic DNA was added to varying amounts of streptavidin (0 to 1024 nM) in 50 μL of 100 mM NaCl, 50 mM Tris-Cl pH 8.0, 5 mM $MgCl_2$ ("assay buffer"), giving a final concentration of labeled DNA of 0.1 mM. The DNA and streptavidin were incubated at room temperature for 30 minutes. A multiscreen-HA 96 well nitrocellulose filter plate (Millipore), which retains protein-DNA complexes much better than free DNA, was pre-washed with 125 μL assay buffer then loaded with each assay sample. The samples were rapidly filtered on a vacuum manifold and the membranes washed twice with 250 μL of assay buffer. The membrane for each well was punched out from the plate using a stylus and the bound radioactive label quantitated by phosphorimager together with 1 fmol of unreacted probe.

(2) Results and Discussion

A starting pool of DNA (for example, random, genomic, or defined sequences) is digested with DNase I. The average size of the resulting fragments is controlled by varying the concentration of DNase I and the duration of the digestion. Fragments of the desired length are purified by preparative gel electrophoresis and treated with T4 DNA polymerase (which can both fill in 5' overhangs and degrade 3' overhangs) to generate blunt-ended, 5'-phosphorylated double-stranded fragments. These blunted-ended fragments are treated with T4 DNA ligase in the presence of 15% poly(ethylene glycol) (PEG). Under these conditions, intermolecular ligation is strongly favored over intramolecular circularization. Since T4 DNA ligase catalyzes the efficient ligation of blunt-ended DNA independent of sequence, fragments recombine randomly and non-homologously. In order to both control the average length of recombined molecules and to install defined sequences at the ends of the diversified DNA library, a synthetic 5'-phosphorylated hairpin is added in a defined stoichiometry to the ligation reaction. Because a DNA molecule capped by ligation to the hairpin can no longer ligate with other molecules, increasing the concentration of hairpin decreases the average length of the recombined library. The hairpin-terminated, recombined DNA pool is then digested with a restriction endonuclease that specifically cleaves at the end of the hairpin sequence to provide the recombined library of linear, double-stranded DNA molecules flanked by a single defined sequence at each end. These molecules are suitable for PCR amplification using a single primer sequence that anneals at both ends of each library member.

To test the ability of this method to recombine DNA nonhomologously, we subjected several pairs of unrelated DNA sequences (~150-300 bp each) to the NRR process described above. The two parental sequences were digested to fragment sizes of 25-75 bp, and then recombined to target sizes of 200-300 bp. The average size of the recombined library could be controlled by modulating the stoichiometry of hairpin in the ligation reaction. Following PCR amplification of the recombined library, individual daughter clones were subcloned into plasmids and sequenced. At recombination junctions (crossovers), the number of bases of homology between the corresponding regions of the parental sequences was counted by inspection. The results of analyzing 124 crossovers from these experiments are as follows. An average of 0.8 bases of homology was found at each crossover, consistent with the theoretical average of 0.7 bases of homology ($2 \times \Sigma 0.25^n$) expected from random chance. As expected, the most frequent crossover events took place with zero bases of sequence homology. These results indicate that NRR allows the facile nonhomologous recombination of unrelated DNA sequences in a length-controllable manner. q (a) Comparison of Nucleic Acid Evolution by NRR Versus Error-Prone PCR To determine how nonhomologous recombination affects the efficiency of nucleic acid evolution compared with point mutagenesis, we evolved a DNA-based streptavidin aptamer using either NRR or error-prone PCR using identical selection conditions and identical starting sequences. A partially mature pool of streptavidin aptamers was generated by subjecting $5 \times 10^{14}$ random 200-mers to three rounds of selection and PCR amplification (SELEX) for binding to streptavidin-linked agarose and elution with free streptavidin. Following three rounds of SELEX, two arbitrarily chosen library members, S3-13 (200-mer) and S3-16 (273-mer), were sequenced and their affinities to free streptavidin were measured to be $K_d = 89 \pm 14$ nM and $133 \pm 42$ nM, respectively.

The sequence of S3-13 is:

(SEQ ID NO: 9)
5'-CGGGGGTGCCCGCTGCTCGTCCAAATGACGGCTCAGCTTCGGTGGGC

CTTTAACAGTAATCAATCATATGAGCAGTTTTCAACGATCACCTACCCAC

ACCGCTCGAATGTTTGCATAAACCTGGGTAGACTCACGCATAATTGGGTT

ATTGAGTCTCTTTGATGGACTAACCCGGTTCTATCTCGGAGGTATTTTAG

GTC-3'

The sequence of S3-16 is:

(SEQ ID NO: 10)
5'-TGACACAAAGACAGACAGGCTATCCAAGAACCCTCTTACTCTGTGAG

ACGACGCACCGGTCGCAGGTTTTGTCTCACAGACGCTAAAAATACAGACA

TGCACCAATGAACAATGAGTTCGACCGTGTTCTTGAGTTTTATGGCCGAT

GTGGTAAGTACTTCTACTGTATCTTCGCGTACCTTAGGTTTAACGTTCTC

TTTTTCGGAATGTGCTCGCCCGCGGCATCCGACGTCCCTTTGGGGGTAG

GTGCAACGGGAATCTTGAGGGATCATT-3'

These two sequences share no homology. These two parental sequences were diversified using either error-prone PCR or NRR to generate three libraries. Error-prone PCR was used to generate a library of point-mutated S3-13 variants and a separate library of mutated S3-16 variants. The third library (termed 13×16) was generated by subjecting S3-13 and S3-16 to NRR using 25-75 bp fragments and recombining to a target size (250 bp) similar to the length of the parents. Following this diversification step, all three libraries were denatured into single-stranded DNA (note that the 5' and 3' ends of each library member were complementary) and subjected to three rounds of SELEX under identical conditions to enrich the sequences with the highest binding affinities. The average streptavidin affinities of the resulting three pools (designated 13E, 16E, and 13×16) were measured as well as the affinities of several individual clones from each pool.

Error-prone PCR of S3-13 followed by three rounds of enrichment yielded a pool of sequences with an average affinity for streptavidin comparable to, or slightly better than, that of S3-13 (average 13E $K_d = 68 \pm 18$ nM), suggesting that point mutagenesis alone is unable to significantly improve the affinity of S3-13. Similarly, the evolution of S3-16 by error-prone PCR also resulted in only very modest increases in average binding affinity (average 16E $K_d = 111 \pm 22$).

Sequences of typical clones arising from the 13E, 16E, and 13×16 libraries were determined. Error-prone PCR introduced mutations into the parental sequences at a rate of approximately 1.3% per base (27 mutations in 2,087 sequenced bases). An examination of these sequences fails to provide obvious structure-function insights such as identifying the active motif within the active sequences; indeed there are no clear correlations between the location or nature of the point mutations and the affinities of the mutant clones.

(b) Using NRR-derived Sequences to Gain Structure-Function Insights

In contrast to error-prone PCR, subjecting S3-13 and S3-16 to NRR followed by three rounds of enrichment yielded aptamers with an average streptavidin affinity of $K_d = 14 \pm 5$ nM. This represents a 6- to 10-fold increase in binding affinity relative to the parental sequences, and a 5- to 8-fold improvement compared with evolution by error-prone PCR. Taken together, these results indicate that, at least in this implementation, while point mutagenesis provided only very modest improvement during DNA aptamer evolution for streptavidin binding, exploring sequence space by NRR yielded significantly more potent streptavidin binders.

An analysis of sequences generated by NRR indicates that nonhomologous recombination, deletion, repetition, and reordering of sequence motifs commonly occurs during NRR. Importantly and in contrast to error-prone PCR, the comparison of even a modest number of these sequences indicates valuable structure-function relationships. Because nonhomologous recombination freely juxtaposes unrelated sequences, only the crucial regions of nucleic acids evolved by NRR are expected to be conserved. Indeed, every sequenced 13×16 clone shares a common subsequence despite their otherwise dramatic differences, and an alignment of the sequences of eight clones from the 13×16 library suggested that a 40-base DNA motif may be in part responsible for streptavidin affinity. NRR recombined sequences are exemplified by the following clones:

13×16#1:

(SEQ ID NO: 11)
5'-GAAAACTGCTCATATGATTGATTAGCCCGCTGCTCGTCCAAATGACG

GCTCAGCTCTGTATTTTTAGCGTCTGTGAGACAGAACCTGCGACCGGTGC

GTCGTCTCACAGTCTACTGTATCTTCGCGTACCTTAGGTTTACCCGCTGC

-continued

```
TCGTCCAAATGACGGCTCTCTGTGAGACAAAACCTGCGACCGGTGCGTCG

TCTCACAGTAAGAGGGTTCTTGGATA-3'
``` and 13×16#5:

```
                                         (SEQ ID NO: 12)
5'-CAAGAACACGGTCGAACTCATTGTTCATTGGTGCACTGTGAGACAAA

ACCTGCGACCGGTGCGTCGTCTCACAGGAGATAGAACCGGGTTAGTCCAT

CAAAGAGACTCTGTGAGACAAAACCTGCGACCGGTGCGTCGTCTCACAGA

GTA-3'
```

Both complementary strands of this 40-base sequence were synthesized and measured for the ability of each strand to bind streptavidin. While one strand demonstrated no streptavidin affinity, the other strand with the sequence:
5'-TCTGTGAGACGACGCACCGGTCGCAG-GTTTTGTCTCACAG-3'(SEQ ID NO: 13) possessed streptavidin binding affinity comparable to that of the sequences evolved by error-prone PCR despite its 5- to 7-fold smaller size relative to S3-13 or S3-16. Using Mfold for DNA (an RNA folding prediction program), this minimal streptavidin aptamer is predicted to fold into the stem-loop structure. The rapid identification of a minimal active DNA from a library evolved by NRR without requiring additional mutagenesis experiments suggests that NRR may reveal important structure-function information in addition to exploring sequence space more efficiently compared with existing methods for nucleic acid diversification.

The following table summarizes the binding constants measured for the parent nucleic acids and evolved progeny.

TABLE 1

| Binding Data | |
|---|---|
| Nucleic acid | Binding constants (nM) |
| Parent 13 | 89 ± 14 |
| Parent 16 | 133 ± 42 |
| Diversified, then selected pools: | |
| Parent 13 EPPCR Pool | 73 ± 14 |
| Parent 16 EPPCR Pool | 104 ± 25 |
| 13 & 16 NRR Pool | 13 ± 4 |
| Individual clones: | |
| 13 EPPCR #3 | 193 ± 43 |
| 13 EPPCR #4 | 51 ± 13 |
| 13 EPPCR #5 | 116 ± 17 |
| 13 EPPCR #6 | 81 ± 22 |
| 16 EPPCR #2 | 104 ± 15 |
| 16 EPPCR #3 | 142 ± 53 |
| 16 EPPCR #4 | 65 ± 10 |
| 16 EPPCR #5 | 88 ± 6 |
| 13 × 16 #1 | 4.7 ± 1 |
| 13 × 16 #2 | 20 ± 8 |
| 13 × 16 #3 | 10.7 ± 0.5 |
| 13 × 16 #5 | 5.3 ± 2.6 |
| 13 × 16 #7 | 23 ± 9 |
| 13 × 16 #8A | 7.3 ± 3.4 |
| 13 × 16 #8B | 3.3 ± 1.2 |

(c) Nucleic Acid Minimization by NRR

The ability of NRR to transform DNA fragments of defined average length into recombined clones of defined average length may allow the removal of nonessential regions from a single parental sequence to generate partially minimized clones. To test this possibility, we subjected a single high-affinity clone from the 13×16 library (13×16#8B, which is 281 nucleotides) to NRR using fragments 25 to 75 bp and a recombined target size of about 100 bp. The NRR-diversified library was subjected to three rounds of SELEX under the same conditions used to select the 13E, 16E, and 13×16 libraries. The resulting enriched library (13×16#8Bmin) demonstrated an average streptavidin binding affinity of $K_d=89\pm15$ nM, comparable to that of the minimal 40-mer. The characterization of the three smallest individual clones isolated from this library revealed affinities consistent with the affinity of the pool ($K_d=79$ to 108 nM) and lengths of 137-159 nucleotides. These results suggest that even in the absence of any sequence data, the ability of NRR to control the length of an evolving pool of nucleic acids allows the partial minimization of active sequences.

(3) Conclusion

A simple method for diversifying nucleic acids during evolution has been developed by nonhomologous random recombination. This method is an effective means of exploring sequence space. NRR not only allows multiple recombination events to take place between any DNA sequences at any position, but also allows the deletion, reordering, and repetition of motifs present in evolving nucleic acid pools. The NRR diversification method is sufficiently straightforward that transforming parental DNA into a PCR-amplified, nonhomologously recombined library could be achieved in a single day. Using NRR, DNA-based streptavidin aptamers were evolved with tight binding affinities, while, in this implementation, evolution using error-prone PCR under identical selection conditions resulted in 10-fold worse average affinities. In addition to generating molecules with greater desired properties during evolution, NRR can also more readily provide structure-function information about evolved sequences compared with error-prone PCR. A minimal 40-mer with streptavidin binding activity was isolated by simple inspection of NRR-generated sequences. NRR was also used to minimize an evolved sequence by subjecting a single active clone to NRR with a small recombined target length.

Several of the high affinity streptavidin binders generated by NRR possess multiple copies of the active 40-mer motif. Because streptavidin is a symmetric protein, it is possible that NRR-evolved sequences have taken advantage of avidity effects to simultaneously bind two or more symmetry-related epitopes of streptavidin. Because some of the highest affinity aptamers do not possess multiple copies of the active 40-mer, avidity effects alone cannot account for the significantly increased affinity of the NRR clones compared with the clones generated by error-prone PCR or the minimal 40-mer itself. The orientations of the active 40-mer relative to flanking motifs and subtle conformational differences between the NRR-evolved clones and the less active variants may also contribute to the enhanced binding of the NRR-derived sequences. Taken together, our findings suggest that nonhomologous recombination may more readily access these differences than point mutagenesis. Consistent with this hypothesis, neither the S3-16 parent nor any of the point mutated 16E clones possessed greater streptavidin affinity than the assayed 13×16 clones, despite the fact that the active 40-mer sequence was present in all of these clones.

Although the examples described here subjected either one or two parental sequences to NRR in order to trace the parentage of each resulting daughter clone, NRR can also be used to diversify a library of many different clones. Such diversification may result in even more significant improvements in desired activity. Of course, NRR can similarly be used for the evolution of RNA in addition to DNA, and for protein coding sequences.

Example 5

Evolution of a Polypeptide Enzyme-TEM-1 β-lactamase

The nucleic acid shuffling method described here is used to evolve the TEM-1β-lactamase of *E. coli*, the enzyme that confers antibiotic resistance to ampicillin. The gene that encodes TEM-1 β-lactamase is modified to include additional unique restriction sites by the introduction of silent amino acid mutations, e.g., by mutating the wobble nucleotide of a codon. The additional restriction sites can be used for mapping or cloning recombinants. A segment of the gene that spans from the initiation codon to the termination codon (i.e., a segment which does not include an untranslated region) is isolated. The segment is treated with increasing concentrations of DnaseI for a limited time. The reaction is then terminated. Conditions that generate fragments in the range of 50 to 300 nucleotides are used. The fragments are filled in with a DNA polymerase and nucleotides. The fragments are ligated together in the presence of two hairpin oligonucleotides. The concentrations of the hairpin oligonucleotides are titrated to identify conditions that produce fragments in a desired size range, e.g., a range of 150 to 5,000 basepairs. The hairpin terminated oligonucleotides are cleaved with SmaI, amplified using primers that anneal to the hairpin in the region attached to the fragment. The amplification products are digested with a Type IIS enzyme to produce rearranged coding segments. The amplification products are cloned into a prokaryotic expression vector and transformed into an ampicillin sensitive *E. coli* strain. Transformations with ampicillin resistance are selected and identified. The shuffled bla gene in the vector can be sequenced and/or used for subsequent rounds of mutagenesis. Polypeptides encoded by the shuffled bla gene are characterized in detail, e.g., by biophysical measurements of protein stability such as by urea denaturation or thermal denaturation, and by enzymatic studies such as measurement of Michaelis-Menten coefficients, $V_{max}$, and enzymatic half-life.

Example 6

Evolution of a Polypeptide Enzyme-Chorismate Mutase Enzyme

The nucleic acid shuffling method described here is used to evolve chorismate mutase enzyme of *E. coli*, an enzyme that catalyzes the Claisen rearrangement of chorismate to prephenate, an essential step in the biosynthesis of tyrosine and phenylalanine.

(a) Molecular Biology Reagents

Restriction enzymes, Vent DNA polymerase, T4 DNA polymerase, and T4 DNA ligase were purchased from New England Biolabs. PCR reagents were purchased from Promega. SDS-PAGE gels were stained for analysis using GelCode blue stain (Pierce) and quantitated by densitometry. Chorismic acid for in vitro kinetic assays on purified proteins was purchased from Sigma-Aldrich. *E. coli* strain KA12 (Kast et al. (1996) *Tetrahedron Letters* 37: 2691-2694) was generously provided by D. Hilvert and P. Kast. *E. coli* strain BL21(DE3)/pLysS was purchased from Novagen.

(b) Oligonucleotides

5'-phosphorylated and PAGE-purified hairpin oligonucleotides PL1 and PL2 were purchased from Sigma-Genosys. PL1 (5'-CATACACGTCATCCGAATTCAGGCCTC-CGGGCGCGCCCGGAGGCCTGAATTCGGAT GACGT-GTATG-3') (SEQ ID NO: 14) contains an AflIII site (underlined) and PL2 (5'-CATGGTGACCCATCCGAATTCAGGCCTGCCGGCGC GCCGGCAGGCCTGAATTCGGA TGGGTCACCATG-3') (SEQ ID NO: 15) contains a BstEII site (underlined) for ligation into the selection plasmid. Both contain a StuI site for removal of hairpin ends (italicized), and both end with NsiI half sites (ATG/CAT) for digesting hairpin dimers and to provide a start codon for translation. PCR primers PL3 (CCT-GAATTCGGATGACGTGTATG) (SEQ ID NO: 16) and PL4 (CCTGAATTCGGATGGGTCACCATG) (SEQ ID NO: 17) were synthesized by standard phosphoramidite chemistry on an Expedite 8909 DNA synthesizer and purified by reverse-phase HPLC.

(c) Construction of Selection Plasmid pCM

Standard PCR, restriction digestion, and DNA ligation methods were used to assemble selection plasmid pCM, which contains the following key components: (i) the p15A replication origin from pACYC184; (ii) tyrA and pheC genes as in pKIMP-UAUC (Kast, et al. (1996) *Proc Natl Acad Sci USA* 93: 5043-8); (iii) the β-lactamase gene from pBR322; (iv) the chloramphenicol acetyltransferase (CAT) gene from pACYC184 for expression as a C-terminal protein fusion (lacking its natural start codon) located immediately downstream of restriction sites for protein library cloning; (v) a tac promoter upstream of the library cloning site. The library insertion site was created using synthetic PCR primers containing AflIII and BstEII sites. The library promoter and insertion sites and the CAT gene were confirmed by sequencing; the tyrA, pheC, and β-lactamase genes, as well as the P15A origin, were confirmed to show activity in vivo. All plasmid fragments were amplified using Vent DNA polymerase.

(d) Protein NRR of Chorismate Mutase

The mMjCM gene (MacBeath et al. (1998) *Science* 279: 1958-61), with Class II optimized codons for *E. coli*, was constructed from overlapping synthetic oligonucleotides, confirmed by sequencing after cloning into a vector, and amplified by PCR using 5'-phosphorylated primers (5'-TTTTTTGTTTTTGTTCTGGGTTTCTTCCAGG-3'(SEQ ID NO: 18) and 5'-ATGATCGAAAAACTGGCA-GAAATCCG-3') (SEQ ID NO: 19). Approximately 4 µg of the 321 bp product was randomly digested using 1-4 µL DNase I solution (Sigma, 7.6 µg/µL,31.3 units/µg, diluted 1,000-fold) in a buffer of 20 mM Tris-HCl (pH 8.0) containing 10 mM MgCl₂ at 25° C. Aliquots were analyzed by gel electrophoresis and the digestion terminated by phenol/chloroform extraction when the fragments reached the desired size range. The fragments were subjected to gel filtration (Princeton Separations) then blunt-ended using T4 DNA polymerase (T4 DNA polymerase buffer, 50 µg/mL BSA, 200 µM dNTPs, 1-3 U T4 DNA polymerase per µg DNA, 30 min at 16° C.). The reaction was extracted with phenol/chloroform and subjected to gel filtration. The desired size range (e.g., 75-125 bp) of pieces was purified by agarose gel electrophoresis, captured using dialysis membrane (6-8000 MWCO), and gel filtration to provide approximately 1 µg of fragments for NRR assembly. 10 pmol of fragments were combined with the desired ratio of hairpins PL1 and PL2 in blunt ligation buffer (T4 DNA ligase buffer with 50 µM ATP, 15% PEG-6000, 18 Weiss units T4 DNA ligase) at 25° C. for 16 h. The ligation reaction was digested with StuI and NsiI, then amplified by PCR using primers PL3 and PL4. The PCR reaction was subjected to gel purification to capture products of desired size (e.g., 300-800 bp), digested with AflIII and BstEII, and gel purified again before ligation into pCM.

(e) Protein NRR of Chorismate Mutase with Fumarase

The E. coli fumarase gene was obtained by PCR from E. coli genomic DNA using 5'-phosphorylated primers 5'-AT-GAATACAGTACGCAGCGAAAAAGATTCG-3' (SEQ ID NO: 20) and 5'-ACGCCCGGCTTTCATACTGCCGACC-3' (SEQ ID NO: 21). The 1401 bp PCR product was gel purified and digested for NRR as described above. A 3:1 ratio of fumarase:chorismate mutase fragments was used in the NRR ligation. The resulting library was amplified and cloned as above.

(f) Chorismate Mutase Activity Selection

The library in pCM was transformed into 320 μL electrocompetent DH10B cells and recovered in 8 mL 2×YT medium at 37° C. for 30 minutes. Ampicillin (100 μg/mL) and IPTG (1 mM) were added and the cells grown at 30° C. for 90 min. A fraction of culture was plated on both 2×YT+ampicillin (100 μg/mL) and 2×YT+chloramphenicol (40 μg/mL) to determine the size of the library and the fraction of clones expressing CAT. For in-frame preselection, the culture was diluted into 500 mL 2×YT+chloramphenicol (40 μg/mL) and grown at 30° C. until saturated before plasmids were isolated and transformed into KA12. Transformed KA12 cells were recovered, washed, and plated on agar containing M9c media+20 μg/mL phenylalanine+100 μg/mL ampicillin+1 mM IPTG at 30° C. (Gamper et al. 2000 Biochemistry 39, 14087-94). For growth without preselection, the initial library ligation was transformed directly into KA12 cells and grown as above. After incubation up to 10 days, colonies were picked, regrown on fresh plates to confirm growth, and then grown in liquid M9c medium+20 μg/mL phenylalanine at 30° C. Active plasmids were isolated and activity was confirmed by recovery of the putative active insert by PCR, religation into pCM, and retransformation into KA12 cells.

(g) Sequence Analysis

Plasmids were sequenced using standard protocols on an ABI Prism 3900 DNA Sequencer. Unselected sequences were obtained by isolating individual colonies from the plates used to determine the size of the initial library and growing in 2×YT+ampicillin. Non-homologous crossovers were located using VectorNTI (Invitrogen) and MACAW software (Schuler (1991) *Proteins* 9, 180-90).

(h) Purification and Analysis of Proteins

Representative active clones were subcloned (without the chloramphenicol acetyltransferase gene) into pET28a (introducing a C-terminal $His_6$ tag) and transformed into BL21 (DE3)/pLysS. A 500 mL culture of a transformant was grown at 37° C. to $OD_{600}$=0.8 before addition of IPTG to 1 mM. Induced cells were grown at 25° C. for 4 h. The cells were harvested by centrifugation and lysed by sonication and treatment with lysozyme. Mutant chorismate mutase proteins in PBS were captured with TALON cobalt-agarose resin (BD Biosciences), washed with 40 mL 5 mM imidazole in PBS, and eluted with 75 mM imidazole+2 mM EDTA in PBS. Cobalt-agarose was used due to the tendency of proteins to precipitate at higher levels of imidazole, possibly indicating relatively unstable proteins. The eluted protein was dialyzed against PBS containing 1 mM β-mercaptoethanol and 10 to 30% glycerol. Final protein solutions were quantitated by SDS-PAGE, staining, and densitometry comparing with pre-quantitated protein standards.

Chorismate mutase activity was assayed as previously described in 0.1 M potassium phosphate buffer (pH 7.5) (Cload (1996) *Amer. Chem. Soc.* 118: 1787-1788). Absorbance at 274 and 304 nm was followed using a Hewlett-Packard 8453 spectrophotometer. Kinetic parameters were extracted by direct fitting of initial rate data to the Michaelis-Menton equation.

(2) Results and Discussion (a) Protein NRR

The application of NRR to the evolution of proteins faces additional challenges compared with nucleic acid evolution using NRR. Assembled genes from protein NRR must be cloned into an expression vector and transformed into cells. Products of the original NRR method, which uses a single hairpin to terminate random intermolecular ligation events, do not clone into expression vectors efficiently due to their identical termini (Bittker (2002) *Nat Biotechnol* 20, 1024-9). Two hairpins were used, each with a different non-palindromic restriction endonuclease cleavage site, to terminate random ligation. This approach generates a statistical mixture of products, 50% of which are terminated with two different hairpins. These products were efficient substrates for cloning and expression. A second challenge of protein NRR is the generation of nonsense mutations through frameshifting or the misorientation of gene fragments. These events reduce the meaningful diversity of protein libraries due to the introduction of internal stop codons that truncate recombined protein products. To minimize the impact of this problem, we designed an expression vector for protein NRR that fuses diversified gene products to chloramphenicol acetyltransferase. Products of protein NRR that contain internal stop codons when introduced into this vector are mostly unable to propagate in *E. coli* cells in the presence of chloramphenicol, although internal ribosome binding sites and start codons could allow chloramphenicol resistance even when following a stop codon. As an added benefit of this preselection step, diversified genes encoding proteins that are unable to be expressed or that are insoluble are also expected to be eliminated. The diversity of the library is increased by performing this pre-selection in a high-competency strain (DH10B), followed by transformation into the selection strain, KA12, which has lower transformation efficiencies.

(b) Nonhomologous Recombination of mMjCM

Figure 2:
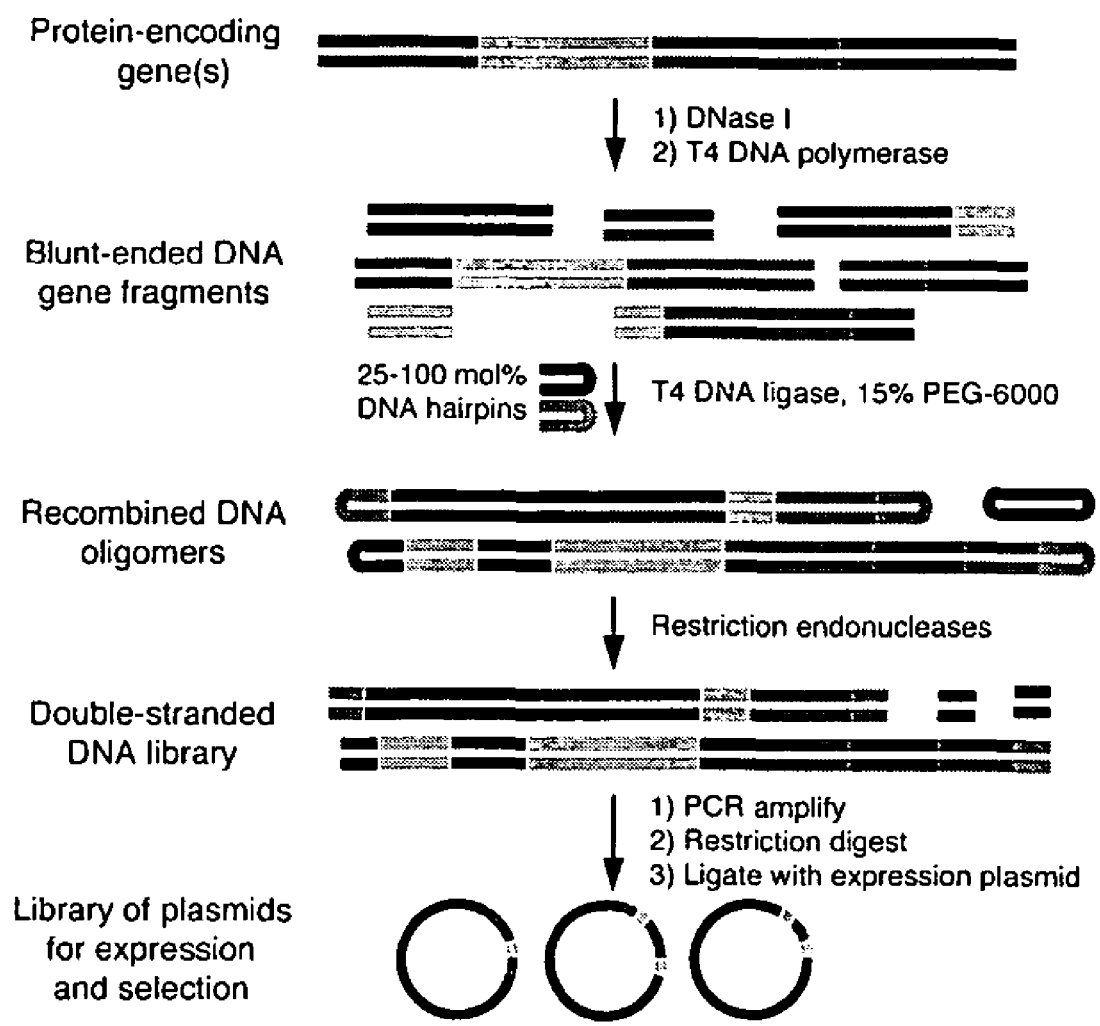
FIG. 2 is another schematic of an example of the nucleic acid shuffling method.

Protein NRR (FIG. 2A) was used to diversify mMjCM. Blunt-ended DNA gene fragments that ranged from 75 to 125 bp were generated and recombined as described previously using a 2:1 ratio of fragments to terminator hairpins (Bittker 2002 *Nat Biotechnol* 20, 1024-9). One or more parental gene are digested with DNase I. Fragments are blunt-ended with T4 DNA polymerase, size-selected, and ligated under conditions that favor intermolecular ligation. Two hairpin sequences are added in a defined stoichiometry to the ligation reaction to generate recombined products of the desired average size. The ends of the hairpins are removed by restriction digestion, and the PCR-amplified pool is cloned for protein expression and selection. In theory, this stoichiometry should result in an average of four fragments recombining before being terminated by a hairpin at each end. Based on the average fragment size, this would create recombined genes of approximately the same size as the parental gene (321 nt) while containing an average of three crossovers.

Figure 3:
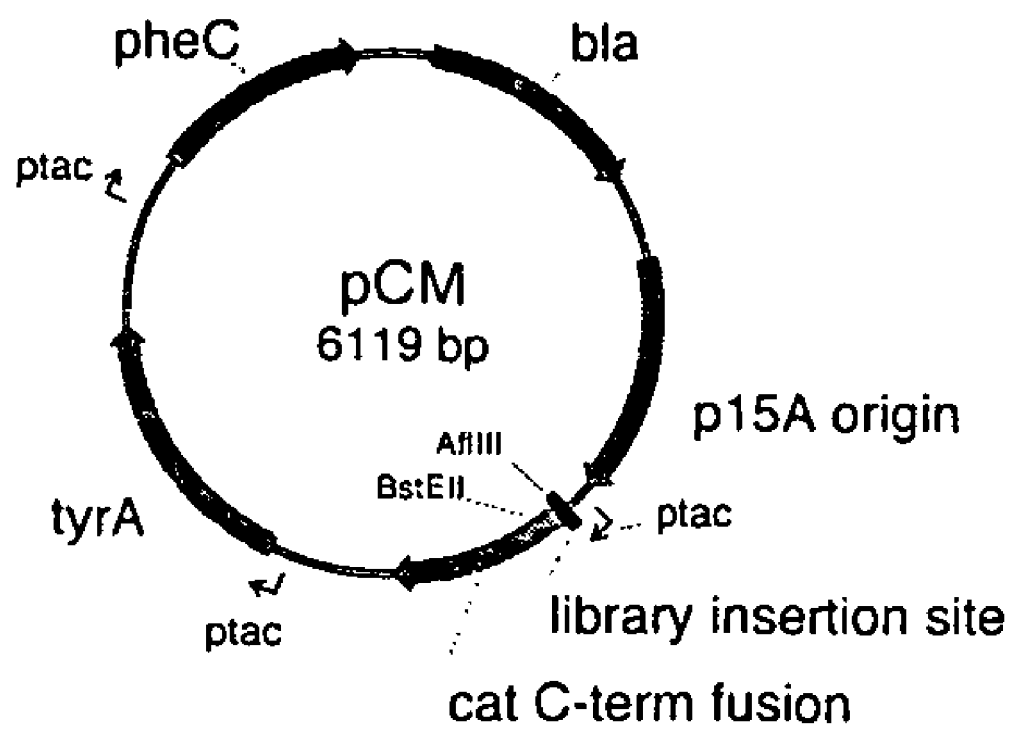
FIG. 3 is a selection plasmid pCM.

The resulting NRR products were digested using enzymes that cleave the closed end of each hairpin and ligated into selection plasmid pCM (FIG. 3). The plasmid library was transformed into highly competent DH10B cells, providing libraries consistently comprising more than $10^8$ ampicillin-resistant transformants. NRR-diversified library members contain an AflIII and a BstEII restriction site for high-efficiency ligation. The library is expressed as a fusion with chloramphenicol acetyltransferase (cat) to allow in-frame preselection. These transformants were preselected for in-frame and soluble proteins by incubation in liquid media containing chloramphenicol. Approximately 2.5% of the initial library (~8×10$^6$ clones) was chloramphenicol resistant.

To evaluate the diversity introduced by protein NRR, genes encoding library members were sequenced prior to selection for chorismate mutase activity. Unselected (inactive) sequences were obtained from two libraries. Clones 1U-14U were derived from an average fragment size of 100 bp; clones 15U-29U were derived from an average fragment size of 50 bp. Numbering across the top corresponds to the residue position in the mMjCM protein. Each arrow represents a recombined fragment. The arrow positions indicate the origin of each fragment within the parental mMjCM gene. Arrow colors indicate the order of fragment reassembly (5'-red-orange-yellow-green-teal-blue-violet-3'). The direction of each arrow indicates the sense (right) or antisense (left) strand of mMjCM. Overlapping arrows indicate sequence that appears more than once in a clone.

Figure 4:
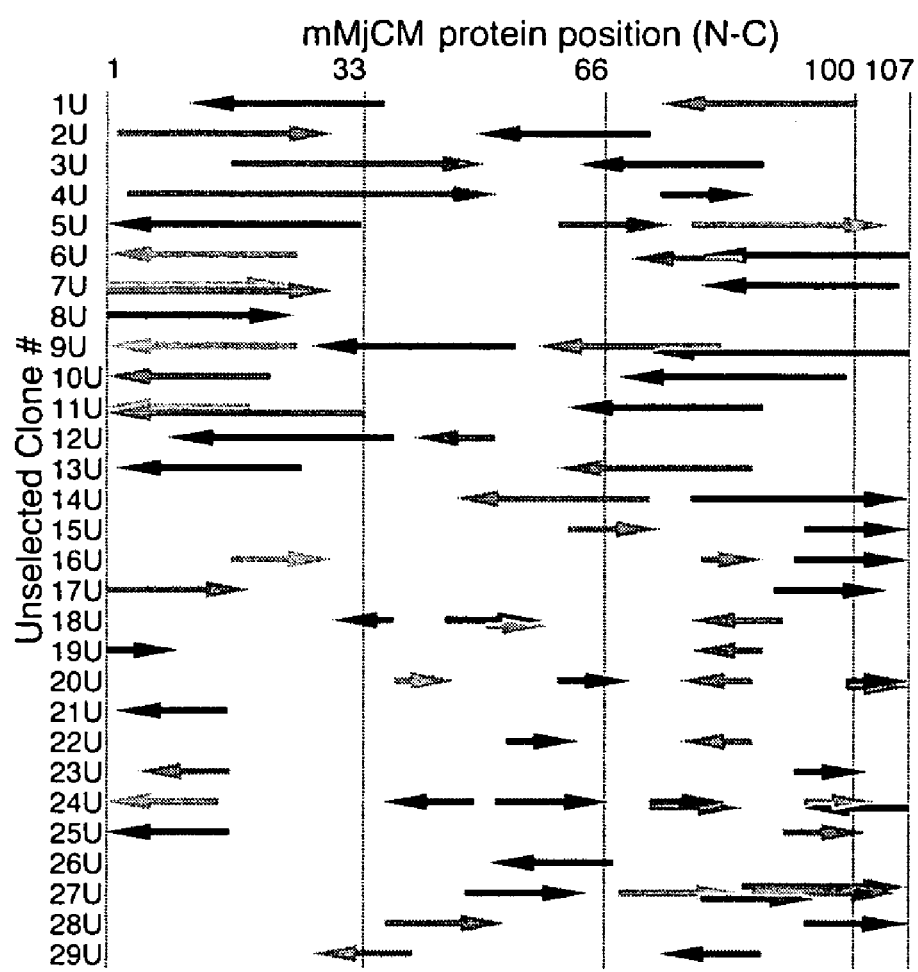
FIG. 4: depicts the sequence diversity created by nonhomologous random recombination (NRR)

FIG. 4 depicts a representative set of sequences obtained from two independent NRR libraries with average target fragment sizes of 75-125 bp (clones 1U-14U) or 40-60 bp (clones 15U-29U). The sequences contain one to seven fragments of the mMjCM gene, with each fragment ranging in size from 21 to 210 bp. The size range of recombined fragments was consistent with target fragment sizes, and no apparent bias in the orientation of the fragments was observed. These results indicate that protein NRR is able to diversify proteins by high-resolution nonhomologous random recombination events (under these conditions generating crossovers at a density of up to nine per 500 bp).

Figure 5:
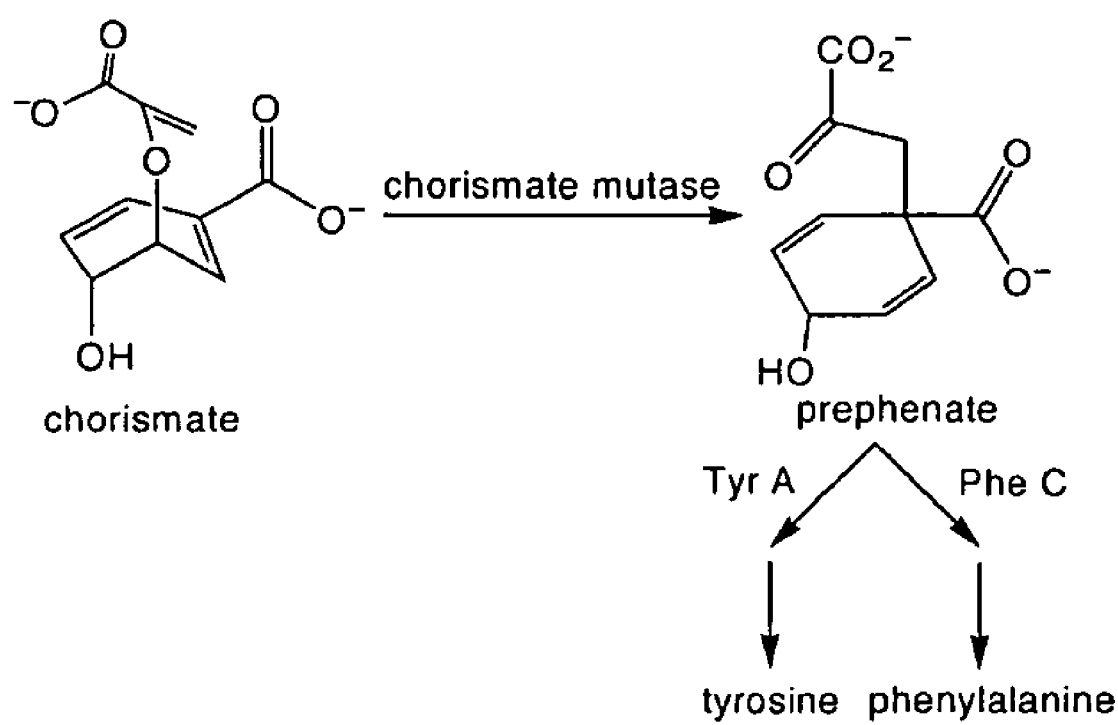
FIG. 5 is a schematic of the Claisen rearrangement catalyzed by chorismate mutase during amino acid biosynthesis.

(c) Active Chorismate Mutase Sequences Contain Deletions, Repetitions, Appendages, and Rearrangements Chorismate mutase catalyzes the Claisen rearrangement of chorismate to prephenate, an essential step in the biosynthesis of tyrosine and phenylalanine (FIG. 5). Cells lacking chorismate mutase activity are unable to grow on media lacking tyrosine. Plasmids containing the preselected NRR-diversified mMjCM library were transformed into the chorismate mutase-deficient *E. coli* strain KA12 developed by Kast and Hilvert, resulting in 3×10$^7$ chloramphenicol-resistant clones prior to selection for chorismate mutase activity (Kast (1996) *Tetrahedron Letters* 37, 2691-2694). This complexity is sufficient to ensure representation of the substantial majority of the preselected clones. The transformed KA12 library was selected for chorismate mutase activity on minimal media lacking tyrosine. Approximately 2,600 active clones were observed, representing a survival rate of one in 11,500 preselected sequences and one in 4.5×10$^5$ initial library clones.

Figure 6:
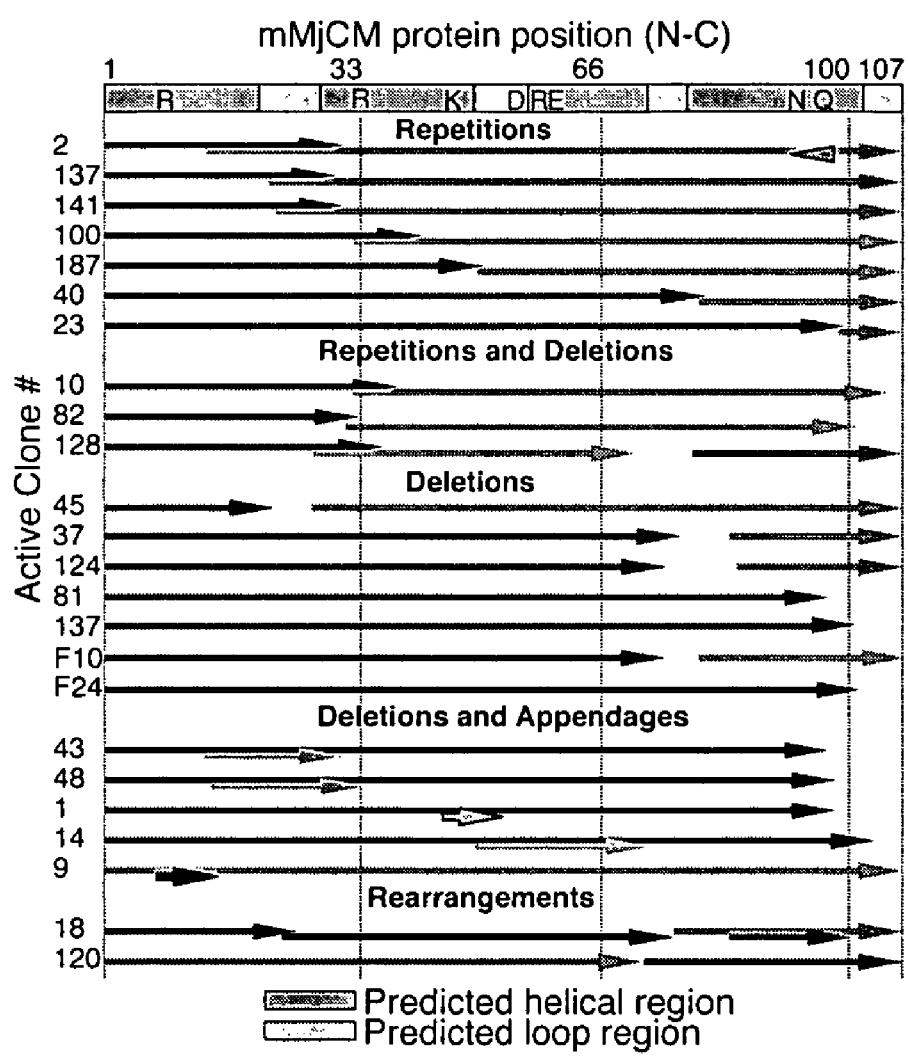
FIG. 6 is the protein sequences of active NRR-diversified mMjCM clones.

The sequences of active clones reveal many significant modifications to mMjCM. Only 42% of the sequenced active clones (27 out of 64) contained full-length mMjCM or mMjCM containing only polymerase-induced point mutations, either from undigested starting material or from reassembly of the full sequence. The remaining sequences (22 unique clones) each contained at least one recombination event, with up to three crossovers observed per active clone. Multiple clones with the same recombined gene were occasionally observed, likely due to the PCR amplification of the library. Several of the selected protein sequences contained a variety of appended, inserted, or deleted amino acids compared with mMjCM (FIG. 6). In contrast with the recombined fragments prior to selection for chorismate mutase activity, among which only 11% (4 out of 35) were expressed in-frame relative to the start codon, 94% (46 out of 49) of the fragments within active clones were in the same frame as the parental gene. The labeling scheme in FIG. 5 is identical to FIG. 3. Arrows outlined in black indicate out-of-frame protein fragments. The bar at the top indicates predicted helical (blue) and loop (pink) regions based on homology with *E. coli* chorismate mutase (Lee (1995) *Amer. Chem. Society* 117 3627-3628). The type of mutation is indicated: overlapping arrows indicate a duplication of one or more residues; gaps indicate a deletion. Predicted active site residues are indicated at the top.

Figure 8:
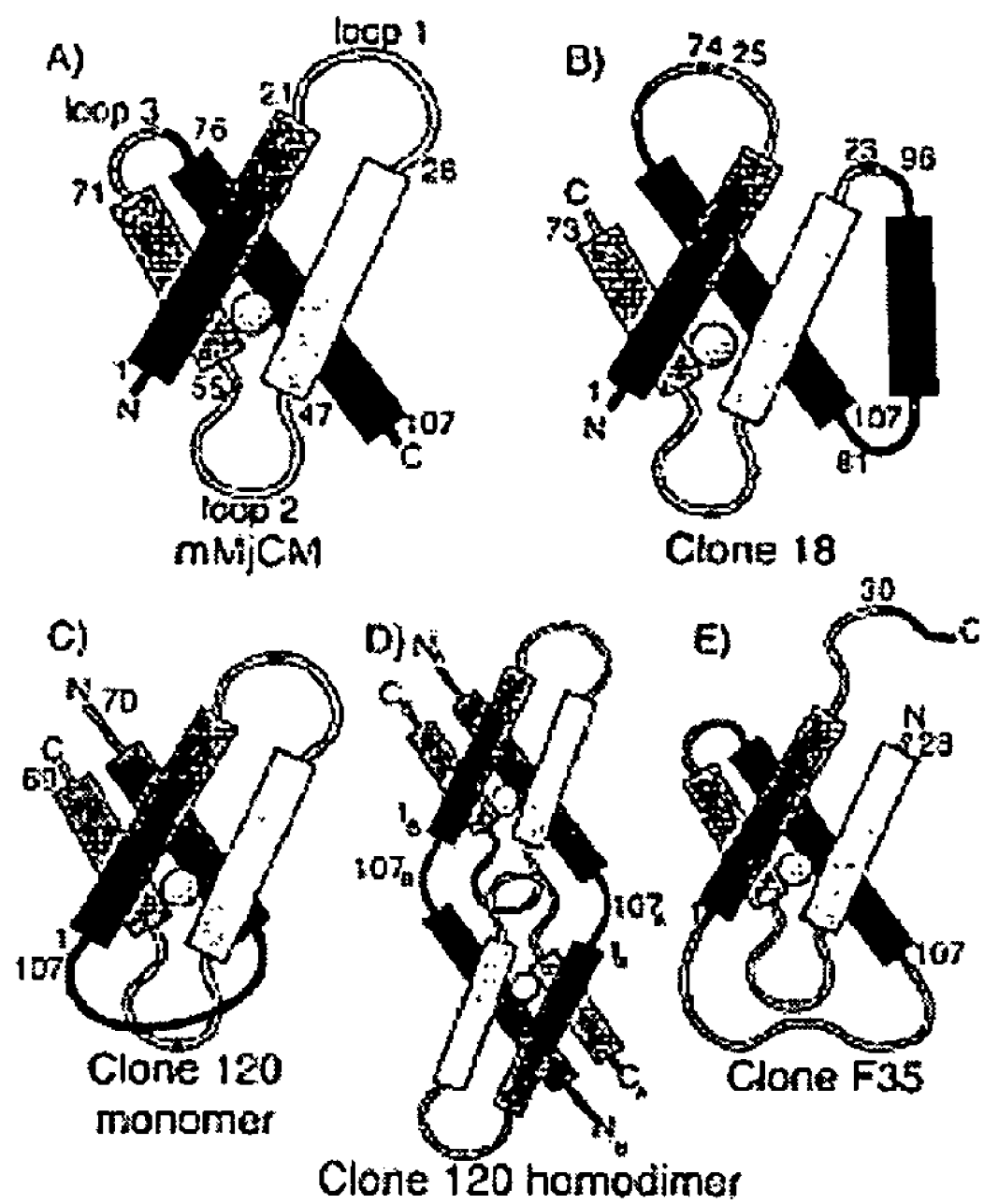
FIG. 8 shows the structural models for selected mMjCM variants.

Two active sequences, clones 18 and 120, contain significant rearrangements of α-helix connectivity within the protein. Clone 18 contains four gene fragments (three crossovers) that reorder the four α-helices in the enzyme from 1-2-3-4 to 1-4-4'-2-3 (FIGS. 6 and 8). Clone 120 is a circular permutant that begins with residue 70, continues to the original C-terminal residue 107, and ends with residues 1-69. Taken together, the sequence diversity found among active chorismate mutase variants highlight regions of low and high structural plasticity within the protein. The implications of specific selected sequences and the distribution of mutations are presented in the Discussion section.

(d) Recombination With an Unrelated Protein Results in Active Chimeric Proteins that Preserve Chorismate Mutase α-Helices

*E. coli* fumarase is unrelated to chorismate mutase in sequence or function but, like chorismate mutase, is largely α-helical (Weaver (1996) *Biochem.* 35 13955-65). To evaluate in a broad and unbiased manner the ability of foreign protein fragments to substitute regions of chorismate mutase, fumarase was recombined with mMjCM using protein NRR. Small fumarase gene fragments (averaging 40 bp each) were used to enhance the resolution of crossovers. A 3:1 molar ratio of fumarase to mMjCM fragments applied significant statistical pressure favoring the incorporation of fumarase sequences. The resulting plasmid library was transformed either into DH 10B cells to characterize diversification, or directly into KA 12 (10$^7$ transformants) for chorismate mutase activity selection. Fifty colonies survived on minimal media lacking tyrosine and were confirmed by recloning to encode functional chorismate mutases. This survival rate of 1 in 2×10$^5$ was 17-fold lower than that of the preselected all-mMjCM library.

The sequences of clones from the recombined chorismate mutase-fumarase library confirmed that most library members contained a mixture of sequence fragments encoding fumarase and chorismate mutase. Among 15 unselected clones, 11 mMjCM and 51 fumarase fragments were found. Fumarase fragments ranged in size from 8 to 77 bp and mMjCM fragments ranged from 17 to 92 bp, consistent with the average size and fragment stoichiometry used to create the library. Recombined sequences contained up to 12 fragments (11 crossovers). The composition of the most highly recombined clone, F-15U, is shown in Table 2.

Figure 7:
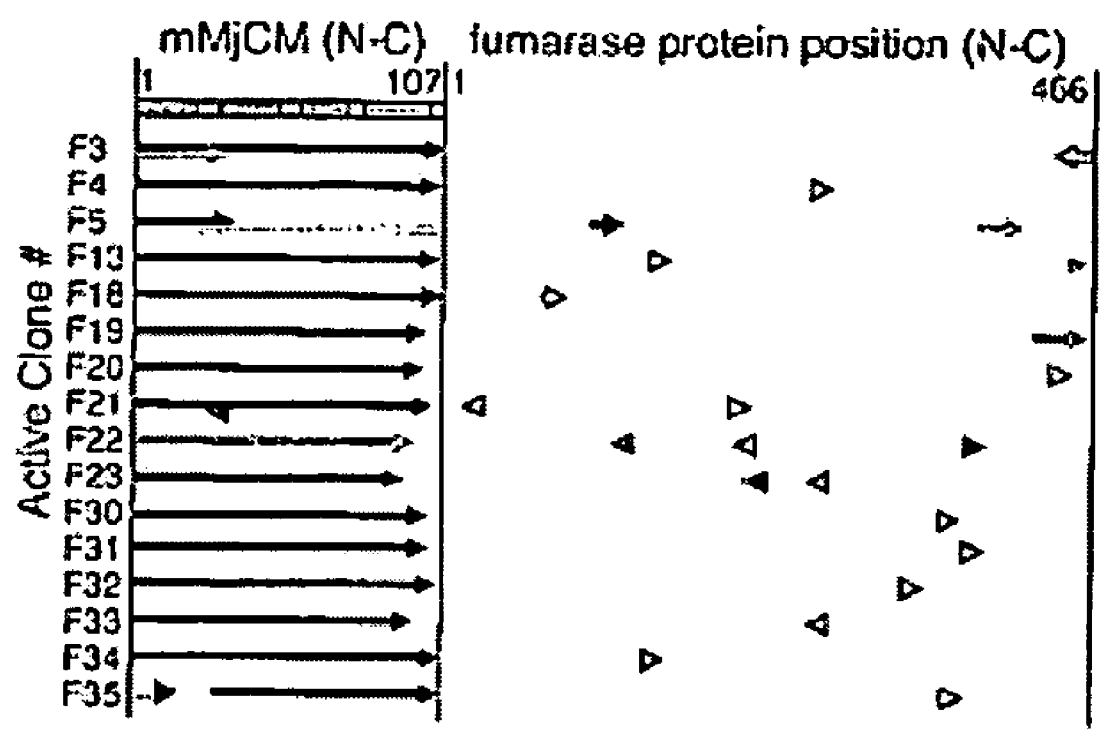
FIG. 7 is the protein sequences of active chorismate mutase-fumarase hybrids.

Only two out of 18 active clones (11%) that were sequenced lacked any fumarase sequence (F10and F24); both contain deletions similar to those seen in the all-mMjCM library (FIG. 6). Interestingly, the sequences of 14 out of 16 active hybrid clones revealed a nearly full-length mMjCM core preceded and/or followed by appendages of the fumarase gene (FIG. 7). The amino acid positions of each fumarase fragment are indicated by their position in the gene as indicated at top.

Only two internal insertions of fumarase were found. One of the insert-containing clones, F-5, is similar to previously characterized all-mMjCM mutants containing insertions at loop 1 but contains an in-frame 39 amino acid fragment of fumarase. While this insertion is longer than any of those described above, all residues of mMjCM are present at least once, indicating that the fumarase insertion in F-5 need not assume the function of any part of mMjCM. Indeed, deletion of four or eight mMjCM helix 1 residues upstream of this fumarase insertion results in the loss of actifity (data not shown). The other internal insertion, clone F-35, is a chimeric circular permutant beginning at mMjCM residue 28 that contains an out-of-frame fumarase linker connecting the former termini of the protein (FIG. 7).

TABLE 2

Composition of F-15U, a highly recombined E. coli fumarase/mMjCM hybrid

| Fragment # | Source |
|---|---|
| 1 | fum 123-87A |
| 2 | mMjCM 279-321 |
| 3 | mMjCM 257-269 |
| 4 | mMjCM 230-321 |
| 5 | mMjCM 113-159 |
| 6 | fum 669-612A |
| 7 | mMjCM 45-1A |
| 8 | fum 862-920 |
| 9 | fum 862-791A |
| 10 | mMjCM 225-161A |
| 11 | mMjCM 46-90 |
| 12 | fum 363-421 |

(A indicates antisense strand)

(e) Selected Clones Diversified by Protein NRR Exhibit Chorismate Mutase Activity In Vitro A subset of proteins surviving selection (from clones 18, 120, 128, and F-35) were individually overexpressed (replacing the chloramphenicol acetyltransferase fusion with a C-purified terminal $His_6$ tag) and purified. The purified proteins were confirmed to catalyze the conversion of chorismate to prephenate in vitro with 5-fold to 9,000-fold lower $k_{cat}/K_m$ values compared with mMjCM (Table 3). For less active proteins, contamination by genomic CM from BL21DE3 was ruled out due to the inability to saturate the protein and by comparison to an inactive protein purfied by the same method.

tion events using protein NRR can be tuned by modulating fragment sizes and fragment: hairpin stoichiometries during intermolecular ligation reactions, inducing in the above examples up to 11 crossovers within a recombined 664 nucleotide chorismate mutase-fumarase hybrid gene, or up to 6 crossovers within a 260 nucleotide chorismate mutase gene. In addition, protein diversification by NRR does not impose any restrictions on the original location of the recombining fragments within parental sequences, enabling dramatic gene rearrangements as observed in the inactive and active chorismate mutase mutants described above. As expected, the ability to access this unusual degree of protein diversification comes at the expense of a lower frequency of active proteins due to frame shifting and the translation of formerly non-coding fragments; the latter problems can be partially avoided with an in-frame preselection using highly competent cells.

Although the three-dimensional structures of mMjCM and its natural progenitor, the dimeric *Methanococcus jannaschii* chorismate mutase (MacBeath (1998) *Biochem.* 37, 10062-73), have not been determined, both are homologous to the structurally characterized dimeric *E. coli* chorismate mutase (Lee (1995) *Amer. Chem. Soc.* 117 3627-3628). An alignment of mMjCM with the *E. coli* protein provides a reasonable model for the location of helical, loop, and active site residues (MacBeath (1998) *Science* 279, 1958-61) (FIGS. 6 and 8*a*). The active mutants generated in this study can be interpreted in light of this structural model. Without exception, each of the functional mutants retains the active site residues present in mMjCM (FIGS. 6 and 7). Two-thirds (10 out of 15) of the observed insertion and deletion mutations align with predicted loop regions (FIG. 6). All 7 of the larger insertions (2-19 amino acids) occur in or within three residues of loop 1, the region previously altered to confer the monomeric state of mMjCM. This loop may be unusually tolerant of insertions, perhaps as a result of these previous mutations. It is also likely that some of these loop 1 insertions revert the resulting protein to a dimeric state.

The observed deletions among active mutants occurred either near loop 3, or at the C-terminus of the protein within the last 13 residues of helix 4. It is tempting to speculate that the junction of helices 3 and 4 does not have stringent sequence requirements because residues that are helical in the wild-type protein may play the role of deleted loop residues; previous reports support this hypothesis (MacBeath (1998) *Prot. Sci* 7: 325-35). Indeed, one mutant containing both an insertion in loop 1 and a deletion of all but one residue in the

TABLE 3

In vitro activities of NRR-diversified chorismate mutases

| protein | modification | $k_{cat}$ (s$^{-1}$) | $K_m$ (µM) | $k_{cat}/K_m$ (µM$^{-1}$s$^{-1}$) | relative activity |
|---|---|---|---|---|---|
| nMjCM | none | 41.6 ± 2.7 | 222 ± 39 | (1.9 ± 0.4) × 10$^5$ | 1 |
| 18 | rearranged connectivity | 14.9 ± 0.5 | 366 ± 29 | (40.7 ± 3.5) × 10$^4$ | 1/5 |
| 120 | circular permutant | nd | nd | (2.1 ± 0.3) × 10$^1$ | 1/9000 |
| 128 | insertion + deletion | nd | nd | (8.1 ± 0.4) × 10$^2$ | 1/230 |
| F-35 | chimeric circular permutant | 1.7 ± 0.2 | 146 ± 57 | (1.1 ± 0.5) × 10$^4$ | 1/17 |

(nd—not determined)

(3) Conclusion

Protein NRR is a simple method that diversifies proteins in ways that are difficult to achieve by existing methods. The implementation of protein NRR is straightforward, enabling starting DNA to be converted into a diversified library in about one day. The frequency of nonhomologous recombinapredicted loop 3 (clone 128) maintained significant in vitro activity (230-fold lower $k_{cat}/K_m$ than mMjCM) (Table 3). These results also indicate that the C-terminal 13 residues in mMjCM are nonessential, a result that is consistent with a similar finding for the *E. coli* chorismate mutase (Chen (2003) *Eur. J. Biochem.* 270: 757-63). Additionally, our results suggest that loop 2 is highly intolerant of mutations, as the only change in this region observed among active clones was the repetition of a single glycine residue (FIG. 6, clone 187). This may be due to the proximity of loop 2 to the active site, with one active site residue (Asp 54) predicted to lie within this loop.

The three rearranged chorismate mutase enzymes obtained through protein NRR (clones 18, 120, and F-35) are of special interest because they each represent secondary structure connectivities previously not known to support catalysis of the Claisen rearrangement of chorismate to prephenate. Based on the homology model of the wild-type mMjCM (FIG. 8*a*), a diagrammatic models for the rearranged mutants was constructed (FIGS. 8*b-e*) that preserve the active site region of each protein and demonstrate the types of topological diversification that can yield functional chorismate mutase enzymes. The structural model of mMjCM in FIG. 8*a* is based on homology between the MjCM dimer and the *E. coli* chorismate mutase dimer. Numbering indicates the approximate residue at the start and the end of each helix. Diagrammatic models of rearranged clones that preserve the active site region (indicated with the sphere). Coloring is maintained from (a) to illustrate crossovers. (b) Clone 18. (c) Clone 120 modeled as a monomer (see text). (d) Clone 120 modeled as a homodimer (see text). (e) Clone F-35. Out-of-frame fumarase residues are indicated in gray; out of frame mMjCM residues are colored magenta. Taken together, the in vivo and in vitro activities (Table 3) of these rearranged mutants, while reduced compared with the starting mMjCM enzyme, establish that multiple secondary structure topologies are capable of providing chorismate mutase activity.

The two evolved circular permutants provide insight into functional ways of joining the termini of mMjCM. Clone 120 (FIG. 8*c*) is a perfect circular permutant with no added or deleted residues. As shown above, the last 13 residues of mMjCM are not essential for activity and therefore in principle could exist either as part of a loop or as part of the last α-helix. As a loop (but not as a helix) these residues could connect the former N and C termini of the protein. A dimeric structure (FIG. 8*d*) that does not require such a long linkage is also possible; this hypothetical dimer, however, would differ significantly from wild-type MjCM as the dimer interface would now comprise residues from the original loop 2 instead of helices 1 and 2. The other circular permutant, clone F-35, uses a fumarase linker to connect the former C and N termini (FIG. 8*e*). A comparison of the activities of these two circular permutants (Table 3) reveals a 550-fold higher $k_{cat}/K_m$ for F-35 compared with clone 120, suggesting that a longer linker between the C and N terminus minimizes conformational distortions that reduce enzyme activity.

Coupled with an efficient functional selection or screen, protein NRR can serve as a useful tool for determining an enzyme's functional requirements in a broad and unbiased manner. In addition, the ability of protein NRR to combine two unrelated proteins can reveal the degree to which the function of secondary structure elements are protein-specific. Although active site residues are expected to be intolerant to substitution, in principle it is possible for secondary structure elements to be exchanged without loss of function when they play similar structural roles in both contexts and do not form precise and crucial interactions with neighboring residues. Consistent with this hypothesis, libraries of sequences matching only the hydrophobic pattern of the wild-type MjCM have been found to result in functional variants (Taylor (2001) *Proc. Natl. Acad. Sci. USA* 98: 10596-601). However, fumarase substitutions within predicted helical regions of chorismate mutase genes were prevalent in libraries only prior to functional selection. The complete disappearance of these substitutions following selection (leaving fumarase fragments only at the termini or in loop 1) suggests that the helical regions of chorismate mutase, including those not involved in active-site contacts, are involved in unique interactions that cannot easily be replicated by regions of foreign helical proteins.

The simple metabolic selection (Kast (1996) *Proc. Natl. Acad. Sci. USA* 93: 5043-8) used in this work was not designed to differentiate mutants of varying activities above a low threshold mutase activity 9,000-fold lower than that of mMjCM was sufficient to confer survival) (Kast (2000) *J. Biol. Chem.* 275: 36832-8). The ability of NRR to greatly diversify gene sequences results in a large majority of inactive sequences, but may result in a small number with improved properties; thus, protein NRR may enable proteins of improved activity to be evolved at the expense of decreasing average activity immediately following NRR diversification. In addition, the discovery of new connectivities that maintain chorismate mutase activity suggests that protein NRR may also be useful to protein engineering efforts that seek an optimal orientation, arrangement, and spacing of structural elements to maximize desired properties. For example, protein NRR may enable the evolution of multifunctional proteins when simple fusion fails to provide the specific and unpredictable contexts necessary for desired function.

The results show the structural plasticity of protein folds and the ability of helical motifs to function in different contexts by applying protein NRR and in vivo selection to the evolution of chorismate mutase enzymes. Functional chorismate mutase mutants evolved using protein NRR contained many insertions, deletions, and rearrangements. The distribution of these changes was not random but clustered in certain regions of the protein. Topologically rearranged but functional enzymes also emerged from these studies, indicating that multiple connectivities can accommodate a functional chorismate mutase active site and demonstrating the ability to generate new domain connectivities through protein NRR. Protein NRR was also used to randomly recombine chorismate mutase and fumarase, an unrelated but also α-helical protein. While the resulting library contained fumarase fragments in many contexts prior to functional selection, library members surviving selection for chorismate mutase activity invariably contained a chorismate mutase core with fumarase sequences found only at the termini or in one loop. These results imply that internal helical fragments cannot be swapped between these proteins without the loss of nearly all chorismate mutase activity. These findings suggest that protein NRR will be useful in probing the functional requirements of enzymes and in the creation of new protein topologies.

Example 7

Preparation of Diversified sRNA Translational Regulators Using NRR and In Vivo Selection (1) Experimental Procedures (a) Strains

*E. coli* strains DH10B and DH12S were purchased from Invitrogen. *E. coli* strain NM22508 (dsrA⁻), expressing a single-copy, chormosomal rpoS-lacZ fusion) and plasmid pNM13 were obtained from S. Gottesman (Majdalani, et al. (1998) *Proc Natl Acad Sci USA* 95: 12462-12467). Plasmid pOxyS and *E. coli* strain DDS1631 (hfq::kan) were obtained from G. Storz and D. Sledjeski, respectively. (Zhang, et al. (1998) *Embo J* 17: 6061-6068; and Sledjeski, et al. (2001) *Bacteriol* 183: 1997-2005).

(b) Oligonucleotides for Library Construction

HPA (5'-P-CATACACGTCATCCGAATTCAGGCCTC-CGGGCGCGCCCGGAGG CCTGAATTCCGGAT-GACGTGTATG-3') (SEQ ID NO: 22) contains an AflIII site (underlined) and HPB (5'-P-CATGGTCACCCATCCGAAT-TCAGCTGGCGGCGG CCGCCGCCAGCTGAATTCG-GATGGGTGACCATG-3') (SEQ ID NO: 23) contains a BstEII site (underlined) for ligation into the selection plasmid pRNA. HPA and HPB also contain StuI and PvuII sites (italicized) for removal of hairpin ends, and both end with NsiI half-sites (ATG/CAT) for digesting hairpin dimers. Primers P1 (CCTGAATTCGGATGACGTGTATG) (SEQ ID NO: 24) and P2 (CTGAATTCGGATGGGTGACCATG) (SEQ ID NO: 25) were used for PCR amplification (see below).

For construction of the random RNA library, P3 (5'-GGCGGCGGCGGTGACC (N)$_{40}$CTAGCCATGACA-CACGTGGCGGC-3') (SEQ ID NO: 26) contains a BstEII site (underlined) and P4 (5'-GCCGCCACGTGTGTCATG-GACTAG-3') (SEQ ID NO: 27) contains an AflIII site (underlined) for ligation into pRNA.

(c) Plasmid Construction

The rpoS-cat fusion used for the selection of rpoS translational activators contains the following components: (i) the last 150 nt of the *E. coli* rpoS 5'UTR, followed by (ii) the first 73 codons of rpoS, and (iii) the chloramphenicol acetyltransferase gene (cat) from pACYC 184 for expression as a C-terminal protein fusion (lacking its natural start codon). Selection plasmid pProt-Cat contains the above construct together with the p15A replication origin from pACYC184, the KanR gene from pACYC177, and a tac promoter upstream of the rpoS-cat cloning site. An analogous plasmid, pProt-CcdB, was constructed for selection of translational repressors in which the cat gene of pProt-Cat was replaced by the cytotoxic gyrase inhibitor gene ccdB from pZero-1 (Invitrogen).

Plasmid pRNA was used for the expression of all sRNA variants and is a derivative of pBAD24 (Guzman, et al. (1995) *J Bacteriol* 177: 4121-4130) in which the arabinose promoter (PBAD) was replaced by the lpp promoter (PLPP) using an upstream ClaI site and a downstream NheI site. The library insertion site, flanked by synthetic BstEII and AflIII sites, is downstream of the transcription start site and upstream of the rrnB terminator.

PCR was used to generate DNA encoding the 87-bp DsrA and 109-bp OxyS RNAs, each flanked by a 5' BstEII and a 3' AflIII site, using pNM13 (Majdalani, et al. (1998) *Proc Natl Acad Sci USA* 95: 12462-12467) and pOxyS (Zhang, et al. (1998) *Embo J* 17: 6061-6068) as templates, respectively. These products were ligated into the same sites on pRNA to generate pRNA-DsrA and pRNA-OxyS. Mutants of selected sRNA regulators were cloned in a similar manner.

(d) Construction of NRR-Diversified dsrA and oxyS Libraries

Using pOxyS and pNM13 as templates, oxyS and dsrA, respectively, were amplified by PCR (oxyS primers:5'-pGAAACGGAGCGGCACCTC-3'(SEQ ID NO: 28) and 5'-pGCGGATCCTGGAGATCCGC-3'(SEQ ID NO: 29)), (dsrA primers: 5'-pAACACATCAGATTTCCTGGTG-TAACGAATTTTTTAAGTGC-3'(SEQ ID NO: 30) and 5'-pAATCCCGACCCTGAGGGGGTCGGGAT-GAACTTGC-3'(SEQ ID NO: 31)). NRR was performed on the resulting PCR products as described above.

Recombined genes were amplified by PCR using primers P1 and P2 and the product was digested with AflIII and BstEII. The desired size range of recombined DNA was purified by gel electrophoresis, then ligated into pRNA.

(e) Construction of the Random 40 nt Library

Primers P3 and P4 (500 pmol each) were annealed and extended with Taq DNA Polymerase. The resulting random DNA library was digested with AflIII and BstEII, then purified by gel electrophoresis and ligated into pRNA.

(f) In Vivo Selection for Translational Activation

An RNA library cloned into pRNA was transformed into 320 µl of electrocompetent DH12S cells harboring pProt-Cat and recovered in 2×yeast/tryptone (2×YT) medium at 37° C. for 30 min. A fraction of the culture was plated on 2×YT plus carbenicillin (Cb) to determine the size of the library. The remaining cells were washed and plated on glycerol minimal media containing 20 mg/ml thiamine, 0.1 mg/ml casamino acids, 25 µM IPTG, 100 mg/ml Cb, and 40 mg/ml chloramphenicol (Cm) at 37° C. After 36 h colonies were picked, cultured, and screened by PCR to confirm the presence of sRNA inserts. Putative active inserts were religated into pRNA and retransformed into DH12S (pProt-Cat) to confirm activity.

(g) In Vivo Selection for Translational Repression

Using the above protocol, a pRNA library was transformed into DH12S (pProt-CcdB) and recovered at 37° C. for 60 min. A fraction of culture was plated on 2×YT+Cb to determine the size of the library. The remaining cells were washed and plated onto glycerol minimal media containing 5 µg/ml thiamine, 1 mg/ml casamino acids, 27.5 µM IPTG, 100 mg/ml Cb and 40 mg/ml kanamycin (Kan) at 37° C. After 36 h cells were harvested and the plasmids from the collected cells were isolated. Inserts from these plasmids were religated into pRNA and subjected to reselection as above. The resulting sRNA-encoding inserts were religated into pRNA and retransformed into DH12S (pProt-CcdB) to confirm activity.

(h) β-Galactosidase (LacZ) Secondary Screen

Plasmids with putative active sRNAs were transformed into *E. coli* strain NM22508, which links rpoS translation with LacZ activity. Assays were performed as previously described (Pryciak, et al. (1996) *Mol Cell Biol* 16: 2614-2626). LacZ activities were normalized to the cell density (OD$_{600}$) of each sample. Each assay was independently repeated three or more times.

(i) Construction of Second-Generation oxyS Libraries

Once the importance of the 11 nt (5'-TTTTTTTTGCC-3') (SEQ ID NO: 32) following oxyS became apparent (see below), two new libraries were constructed. Library R3 used an extended (120 bp) oxyS PCR product (generated from the original 5' primer for oxyS and a new 3' primer, 5'-GGCAAAAAAAAGCGGATCCTGGAGATCCGC-3') (SEQ ID NO: 33) as the starting material for NRR. Library R4 used the 109 bp oxyS PCR product for NRR, but used an alternate hairpin sequence containing the 11 nt region above (5'-CTTTTTTTTGCCACACGTGAATTCGGC-CCGCGGGCCGAATTCACGTGTGGCAAAAAA AAG-3') (SEQ ID NO: 34). Primers P2 and P5 (5'-GCGAAT-TCACGTGTGGCAAAAAAAAG-3') (SEQ ID NO: 35) were used to amplify this library after NRR.

(j) Assay for Hfq Dependence

*E. coli* strain DDS1631 (hfq::kan) (Sledjeski, et al. (2001) *Bacteriol* 183: 1997-2005) was supplemented with a plasmid, pBadHfq, that contained the hfq gene under control of a pBad promoter. This plasmid contains the following key components: (i) the p15A origin of replication and the Cm resistance gene from pACYC184; (ii) the PBAD promoter from plasmid pBAD24; and (iii) the hfq gene, obtained by PCR from *E. coli* genomic DNA introducing NheI and PstI restriction sites for cloning. To evaluate Hfq dependence, pRNA plasmids were introduced into DDS 1631 (pBadHfq), grown in 2×YT with 0.2% glucose (Hfq repressed) or 0.2% arabinose (Hfq expressed), and assayed for LacZ activity as above.

(k) Quantitative Reverse Transcriptase PCR

RNA was isolated by hot-phenol extraction from NM22508 transformed with the plasmid encoding the sRNA of interest (Argaman, et al. (2001) Curr Biol 11: 941-950). Total RNA was treated with 10 U RNase-free DNase I (New England Biolabs) in the presence of 2.5 mM MgCl2 for 30 min at 37° C. DNase cleavage was terminated by phenol-chloroform extraction followed by ethanol precipitation. From the resulting material, 1 μg total RNA was treated with reverse transcriptase from the Moloney Murine Leukemia Virus (New England Biolabs) at 42° C. as described by the manufacturer in the presence of 50 pmol primer A (for the activators, 5' CAAGAAGCACTTAAAAAATTC) (SEQ ID NO: 36) or primer B (for the repressors, 5'GATCCG-CAAAAGTTCACG) (SEQ ID NO: 37). Reverse transcriptase activity was terminated by heating at 95° C. for 10 min.

Serial dilutions of purified and quantitated plasmid DNA were used as reference templates to facilitate the accuracy of comparisons between RNA samples during quantitative (real-time) PCR. The reference DNA or 1 μL of the reverse transcriptase reaction was mixed with 25 pmol primer A or B, sense primer (5'AACGCGCTAGCGGTGACC) (SEQ ID NO: 38), 2×QuantiTect SYBR Green PCR Master Mix (Qiagen) and sterile water to a final volume of 50 μL. Quantitative PCR reactions were performed using a DNA Engine Opticon 2 (MJ Research) with an initial denaturation step of 15 min at 95° C. followed by 40 cycles of 30 s at 94° C., 45 s at 50° C., and 45 s at 72° C. The fluorescence was measured at the end of each extension step. Finally, a melting curve was recorded between 48° C. and 99° C. with a hold every 2 s. Relative RNA concentrations were calculated by comparison to the standard curves.

(2) Results and Discussion (a) Development of an in Vivo Selection for rpoS Translational Activation The approach requires a method for rapidly evaluating rpoS translational regulation. An in vivo selection for translational activation was developed based on the expression of cat (chloramphenicol acetyltransferase), which confers resistance to the antibiotic chloramphenicol. E. coli cells entering this selection carry two plasmids. Plasmid pProt-Cat expresses Cat, from an inducible tac promoter, as a C-terminal fusion to the first 73 amino acids of RpoS (Brown, et al. (1997) J Bacteriol 179: 656-662). The rpoS start codon in pProt-Cat is preceded by 150 nucleotide of the rpoS 5' UTR (FIG. 9A). The base numbering of RpoS follows that of Brown and Elliott (Brown, et al. (1997) Supra). The Shine-Dalgamo sequence is underlined and the start codon is labeled. Based on the results, nucleotides proposed to pair with DsrA, OxyS SL1 (sense), OxyS SL1 (antisense), and OxyS SL3 are highlighted in yellow, red, blue, and green, respectively.

The second plasmid, pRNA, expresses a library of sRNAs. The sRNAs expressed from the 1 pp promoter of pRNA carry an additional 18 nucleotide at their 5' end; an rrnB terminator follows the sRNA cloning site in pRNA. Although this cloning scheme inserts additional nucleotides to the 5' and 3' ends of the sRNAs, the control selections performed with pRNA-DsrA and pRNA-OxyS indicated that these alterations did not significantly affect the activities of the sRNA regulators.

The selection was designed such that only in the presence of RpoS translational activators would sufficient Cat fusion protein be expressed to confer resistance to a specific concentration of chloramphenicol. This selection was validated by introducing pRNA expressing wild-type DsrA, wild-type OxyS, or no sRNA into E. coli cells harboring pProt-Cat. We observed optimal growth differences when cells were plated on 40 μg/mL chloramphenicol; these conditions allowed 1% of cells expressing DsrA to survive, while only 1 in $10^4$ cells lacking an sRNA insert and 1 in $10^5$ cells expressing OxyS survived. These results indicate that our system successfully links rpoS translational activation with cell survival.

A secondary LacZ screen was used to verify the activity of sRNAs surviving this selection. E. coli strain NM22508 expresses a single copy, chromosomal rpoS-lacZ translational fusion (Majdalani, et al. (1998) Proc Natl Acad Sci USA 95: 12462-12467), enabling the quantitative measurement of rpoS translational initiation in a context different from that of the selection. RNA sequences that could both survive the Cat selection and pass the LacZ screen by inducing lacZ expression levels comparable to or greater than that of wild-type DsrA were considered positive activators. These sRNAs, like wild-type DsrA, are rpoS-specific, but are not dependent on a specific reporter gene.

(b) Development of an in Vivo Selection for rpoS Translational Repression

An analogous selection was developed for sRNAs A40c, that repress rpoS translation. Plasmid pProt-CcdB expresses the toxic gyrase inhibitor CcdB (Kampranis, et al. (1999) J Mol Biol 293: 733-744) as a C-terminal fusion to the RpoS fragment described above. The selection was designed such that the toxicity of CcdB would prevent the growth of cells not expressing translational repressors of the rpoS-ccdB fusion.

The stringency of the selection was varied by titrating the concentration of IPTG used to induce rpoS-ccdB expression from its tac promoter. At an optimized concentration of 27.5 μM IPTG, the selection allowed 1 in 500 OxyS-expressing cells to survive, while control cells expressing no sRNA or DsrA survived at a rate of 1 in $1 \times 10^4$ or 1 in $1.5 \times 10^4$, respectively. To further enrich for authentic repressors, two iterated rounds of this selection were performed on the libraries described below. The activities of selected RNA repressors were also evaluated in the secondary LacZ screen described above (Majdalani, et al. (1998) Proc Natl Acad Sci USA 95: 12462-12467); sRNAs that reduced LacZ expression to an extent comparable to or greater than that of wild-type OxyS were considered positives.

(c) Creation of RNA Libraries

The NRR method was used to diversify dsrA and oxyS separately into libraries of randomly and nonhomologously recombined fragments. While the sequences 5' and 3' to the sRNA genes could play a role in sRNA activity, the focus was specifically on the regions of dsrA and oxyS that are known to be transcribed and allow for full translational regulation of RpoS expression (FIGS. 9A and 9B). It was reasoned that this approach would allow the most direct comparison of the active regions of DsrA and OxyS that confer their respective activities. FIG. 9(B) shows a model of RpoS 5' UTR secondary structure and proposed anti-antisense mechanism for translational activation by DsrA (Majdalani, et al. (1998) Supra; Lease, et al. (2000) Supra; and Lease, et al. (1998) Supra). The Shine-Dalgamo sequence is boldfaced, the RpoS start codon is underlined, and RpoS bases 113-115 are highlighted in orange. FIG. 9(C) shows that DsrA and 9(D) OxyS secondary structure as predicted by nuclease footprinting and the mFOLD program, respectively (Lease, et al. (2000) Supra and Zuker, et al. (2003) Nucl. Acids Res 31:3406-3415).

The NRR-diversified dsrA (activator) library, A1, was constructed with gene fragments that ranged from 10-70 bp and were recombined to a target gene size of 80-150 bp. Two NRR-diversified oxyS (repressor) libraries, R1 and R2, were constructed. In R1, blunt-ended oxyS gene fragments 5-30 bp were recombined into 80-100 bp genes, while in R2, 20-70 bp fragments were joined into 100-150 bp recombinants. Libraries containing the NRR-diversified sequences were cloned into pRNA and the resulting plasmids were introduced into *E. coli* DH10B cells, generating libraries of $1\times10^6$ to $1\times10^8$ transformants. For comparison, we also prepared library N1, expressing 40 consecutive random RNA nucleotides ($8\times10^7$ transformants).

Figure 10:
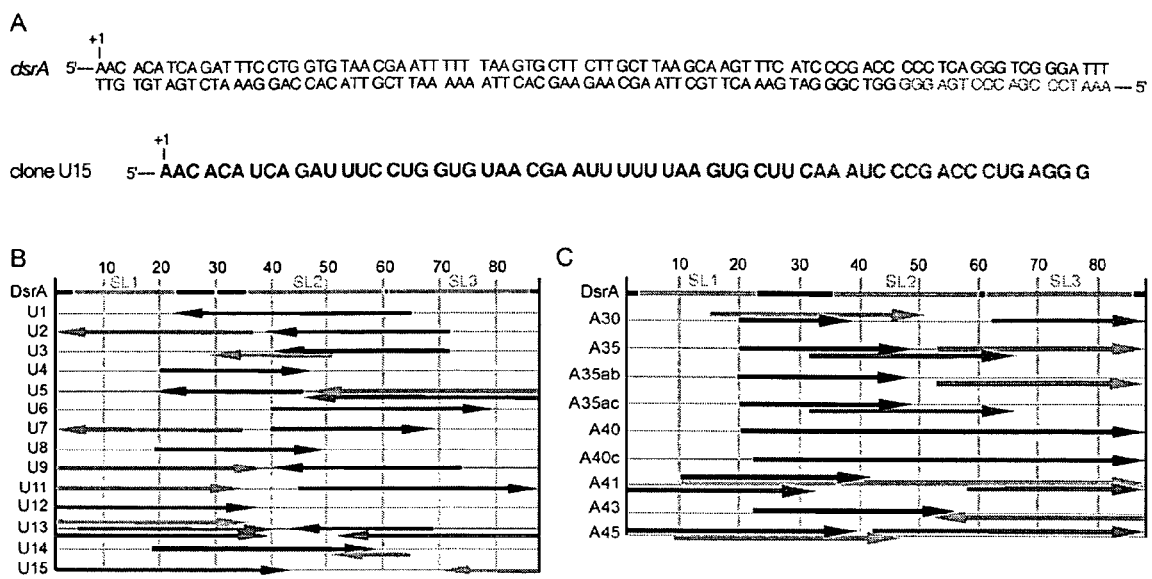
FIG. 10A is an example of a NRR-diversified DsrA variant. Sequences from both the sense and antisense strands of dsrA (SEQ ID NO. 50) recombine to form recombined variant U15 (SEQ ID NO. 51)
FIG. 10B shows NRR-diversified variants of DsrA prior to selection. Each arrow represents a recombined fragment.
FIG. 10C shows NRR-diversified variants of active RNA activators of RpoS translation after selection and screening.

To assess the diversity introduced by NRR, several unselected library members from library A1 were characterized by DNA sequencing (FIGS. 10A and 10B). In the graphical depictions of the recombined sequences in FIG. 10, which shows a NRR-diversified DsrA variant, sequences from both the sense and antisense strands of dsrA recombine to form recombined variant U15. Each individual fragment derived from the dsrA gene (FIG. 2A, top line) is shown as a single, color-coded arrow. The arrow colors indicate the arrangement of the fragments within a single transcript (red-purple is first-last fragment). The position and orientation of the arrow indicates the gene sequence of the fragment and whether the sequence is from the sense or anti-sense strand of dsrA. The sRNA U15, for example, consists of two fragments derived from dsrA (FIG. 10A, bottom line). The first fragment (red) is from the 5' end of the sense strand of dsrA. The second fragment (orange) is from the 5' end of the antisense strand. Consistent with the library design, the diversified sequences of A1 ranged in length from 29-174 bp and contained zero to four crossovers between fragments ranging in size from 12-79 bp. As expected, the sense and antisense strands of the parental DNA before selection were similarly represented (48% sense strands). FIG. 10(B) shows NRR-diversified variants prior to selection. Numbering across the top corresponds to the nucleotide position in DsrA. Each arrow represents a recombined fragment. Arrow positions indicate the origin of each fragment within the parental dsrA gene. Arrow colors indicate the order of the fragment reassembly (5'-red-orange-green-blue-purple-3'). The direction of each arrow signifies the sense (pointing right) or antisense (pointing left) strand of dsrA. FIG. 10(C) Composition of active RNA activators of RpoS translation after selection and screening. The labeling scheme is as described in FIG. 10(B).

(d) Translational Regulators do not Arise from Random or Unrelated Sequences

The high degree of diversification introduced by NRR raises the possibility that translational activators or repressors unrelated in structure or mechanism to that of DsrA or OxyS might arise by chance in our libraries. To determine the frequency with which sRNA translational regulators unrelated to DsrA or OxyS spontaneously arise from our libraries, we performed a series of control selections. *E. coli* expressing repressor libraries R1 and R2 ($5\times10^7$ transformants total), and random $N_{40}$ library N1 ($8\times10^7$ transformants) were separately selected for RpoS translational activation as described above. The RNA sequences surviving the selections (ten examples each picked from a survival rate of ~1 in $10^4$) were screened for their ability to activate the translation of rpoS-lacZ in *E. coli* strain NM22508. For all three libraries, none of the clones surviving selection expressed LacZ activity. Similarly, random library N1 ($1\times10^4$ transformants total) and activator library A1 ($1\times10^4$ transformants total) were selected for rpoS translational repression and screened using the RpoS-LacZ assay. Once again no active clones were observed.

Taken together, these results suggest that rpoS specificity and translational regulation activity are uncommon features of DsrA and OxyS that make the spontaneous formation of rpoS translational regulators from unrelated or random sequences highly unlikely. The inability of unrelated or random RNA sequences to give rise to translational activators and repressors supports our assumption that the active sRNAs emerging from the selections described below operate by DsrA-like and OxyS-like mechanisms.

(e) Selection of Translational Activators from a dsrA-Based Library

The A1 library was selected for rpoS-cat translational activation and screened for rpoS-lacZ translational activation as described above. In contrast with the inability of selected RNAs from the control selections to pass secondary screening, six sequences from the dsrA-based library both activated RpoS-Cat expression in DH12S(pProt-Cat), and activated RpoS-LacZ expression in NM22508 (FIGS. 10C and 11A). FIG. 10(C) Composition of active RNA activators of RpoS translation after selection and screening. The labeling scheme is as described in FIG. 10(B). FIG. 11A shows the RpoS-LacZ translational activation by DsrA variants relative to a pRNA control lacking an sRNA insert The sequences of the active clones reveal significant structural rearrangements of dsrA (FIG. 10C). In contrast with the sequences prior to selection, 94% (15 out of 16) of the fragments from the selected sequences are from the sense strand of dsrA, consistent with enrichment for functional DsrA variants. Interestingly, the more active DsrA variants, such as A41 and A45, contain repetitions of subsequences suggesting that avidity effects may enhance translational activation.

Each of the six active sequences contains at least one copy of the putative U-rich Hfq-binding site (bases 23-35 of DsrA), suggesting that Hfq mediates an interaction between these sRNAs and the RpoS mRNA. To evaluate the dependence of translational activation on Hfq, a representative set of four active sequences in an Hfq deficient strain were assayed. Similar to wild type DsrA (Sledjeski, et al. (2001) *Bacteriol* 183: 1997-2005), the absence of Hfq significantly impairs, but does not eliminate, the activity of the selected sequences (FIG. 11B). FIG. 11(B) shows the activities of selected RNA sequences in the presence and absence of Hfq. Miller units (M.U.) are used to quantitatively represent expression of B-galactosidase from an RpoS-LacZ fusion. Taken together, these results suggest that the selected sequences have inherited the features of DsrA that confer its Hfq-dependence and, therefore, likely activate RpoS translation through a similar mechanism. Interestingly, in the absence of Hfq, the selected sRNAs all have similar activity. The pleiotropic nature of Hfq and the presence of other sRNAs that activate RpoS translation may account for this observation. FIG. 11(C) RpoS-LacZ translational activation, relative to a pRNA control, by selected RNA sequences with 5'-TTTTATTGT (SEQ ID NO: 39) appended to their genes' 3' ends. Error bars represent standard deviations of three or more independent trials.

(f) Intracellular Abundance of DsrA Variants

Figure 11:
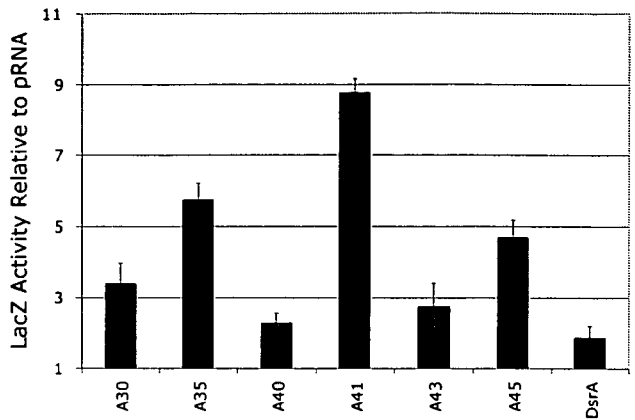
FIG. 11A is a bar graph depicting RpoS-LacZ translational activation by DsrA variants relative to a pRNA control lacking an sRNA insert.
FIG. 11B is a bar graph depicting activities of selected RNA sequences in the presence and absence of Hfq.
FIG. 11C is a bar graph depicting RpoS-LacZ translational activation, relative to a pRNA control, by selected RNA sequences.
Figure 11:
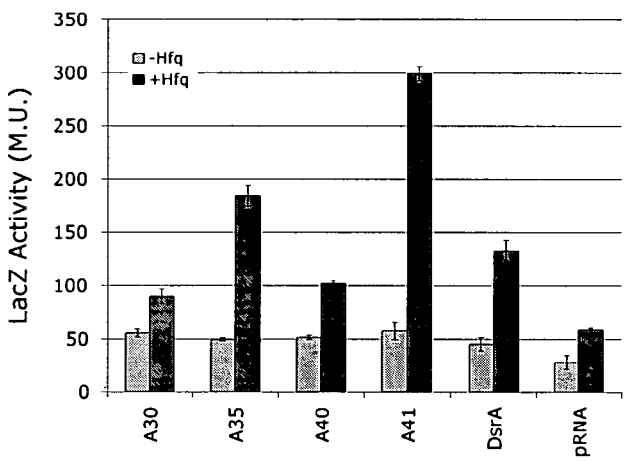
Figure 11:
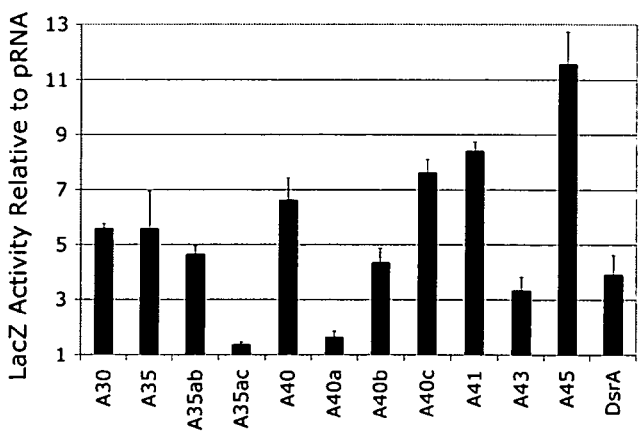
Figure 12:
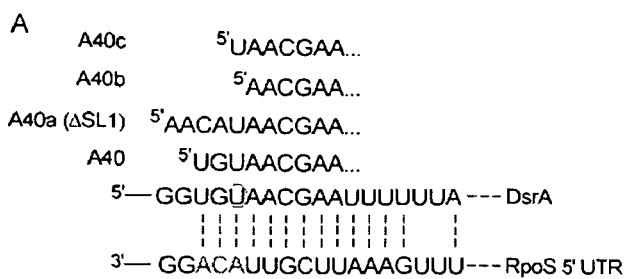
FIG. 12A shows potential base pairs between A40 variants (A40c, A40b, A40a, (SEQ ID NO. 52), A40) and the RpoS leader (SEQ ID NO. 53)
FIG. 12B shows a comparison of translational activation activity and intracellular abundance of selected RNA sequences.
FIG. 12C is a bar graph showing the intracellular abundance of sRNA activators, relative to DsrA, as measured by quantitative reverse transcriptase PCR.
Figure 12:
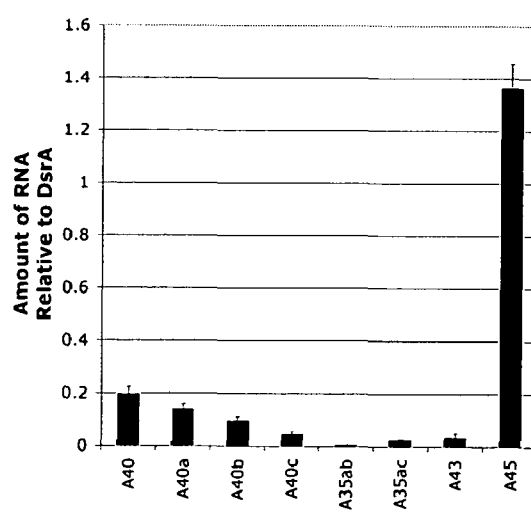

As shown in FIG. 11, the activities of the selected activators vary widely, from each other and from DsrA. It was reasoned that differences in stability and abundance could account for these observations. In order to explore this possibility, quantitative reverse transcriptase-PCR was used to measure the intracellular levels of three representative groups of DsrA variants (FIGS. 12B and 12C). FIG. 12 shows the analysis of selected translational activators. FIG. 12(A) shows the potential base pairs between A40 variants and the RpoS leader. Complementary bases are shown in blue, while mismatches are red. DsrA U22 is circled; RpoS nt 113-115 are highlighted in orange.

Group 1 includes sRNAs with high (A45), medium (A40) and low (A43) activity, as well as wild-type DsrA. No significant difference was observed in RNA levels between A45 and DsrA that could account for the observed 3-fold greater activity of A45. In the case of A40 and A43, the selected sRNAs are five- and 40-fold less abundant, respectively, than that of DsrA. The lack of SL1 in both sRNAs likely explains their lower stability. In the case of A43, SL3 has been inverted, which may further contribute to its lower abundance. The intracellular levels of these sRNAs, however, cannot alone account for their differences in activity as both A40 and A43 are at least as active as DsrA.

Groups 2 and 3 represent the series of sRNA mutants discussed below. These results also show a similar lack of correlation between translational activation activity and intracellular abundance (FIGS. 12B and 12C). FIG. 12(B) shows a comparison of translational activation activity and intracellular abundance of selected RNA sequences. FIG. 12(C) shows the intracellular abundance of sRNA activators, relative to DsrA, as measured by quantitative reverse transcriptase PCR. Error bars represent standard deviations of three or more independent trials. In all studies, controls lacking reverse transcriptase or template RNA showed no signal above background. Specifically, A35ab and A35ac were comparably abundant, while A40, A40a, A40b, and A40c were also present at similar intracellular levels. Based on these observations, we conclude that while the selected DsrA variants differ in their intracellular abundance, these differences cannot account for their observed changes in activity within each group.

(g) The Role of DsrA Stem-Loop 3

A comparison of active and inactive sequences identifies regions essential for DsrA activity (FIGS. 10B and 10C). For example, RNAs lacking a complete SL3, despite containing other regions found to be essential (e.g., clones U4, U8, U12, U14, and U15) were found to be inactive, strongly suggesting that an intact SL3 is required for activity. The order in which the essential fragments occur is also important. For example, the sequence of inactive clone U11 contains a complete SL3 followed by a nearly complete SL1 and Hfq binding site, but these components occur in the opposite order compared with active clones A35, A41, and A45.

Highly active clone A35 consists of three fragments containing: (a) the end of SL1+half of SL2; (b) SL3; and (c) SL2 (FIG. 10C). To study the role of SL3 in detail, mutants of A35 missing either (b) or (c) were constructed and assayed. While deletion of the fragment after SL3 (mutant A35ab) did not impair activity, deletion of the fragment containing SL3 (A35ac) reduced activity 4-fold (FIGS. 10C and 11C), confirming the importance of SL3 in this clone.

The observation showed that wild-type DsrA activated translation of rpoS-lacZ to a lesser extent than previously reported (Sledjeski, et al. (1996) *Embo J* 15: 3993-4000 and Majdalani, et al. (1998) *Proc Natl Acad Sci USA* 95: 12462-12467) (~2-fold versus>4-fold, see FIG. 11A). It was noted that the two most active clones to emerge from the selection (A35 and A41, both 3 - to 4-fold more active than DsrA, FIG. 11A) each include a fragment containing at least five thymidines downstream of the SL3 fragment. Since SL3 has been implicated as a rho-independent transcriptional terminator, we reasoned that the use of the rrnB terminator was a poor choice in vector design; it is likely that appending the additional nucleotides to the 3' end of DsrA was responsible for the observed decreased activity.

Indeed, the addition of the native 3' sequence (TTTTATTGT) (SEQ ID NO: 40) to the 3'-end of our wild-type dsrA construct increased the sRNA activity to 4-fold activation (FIG. 11C). The addition of the T-rich sequence to the end of other active clones (A30, A40, and A45) similarly increased activity approximately 2-fold in each case (compare FIGS. 11A and 11C). The experiments described below use these new constructs.

(h) The role of DsrA stem-loop 1

Previous studies have suggested that SL1 is essential to DsrA activity and participates in base pairing with the rpoS mRNA. While all six active clones contain the SL1-SL2 linker, four of the clones lack large portions of SL1 (FIG. 10C). Notably, clone A40 begins with only the last three bases of SL1 (UGU) followed by the remainder of DsrA, yet is at least as active as wild-type DsrA (FIGS. 11A and 11C). These results indicate that SL1 is not necessary for translational activation. In apparent contrast with the present findings, Gottesman and coworkers reported that deletion of SL1 (DSL1; 5'-AACAU followed by the SL1-SL2 linker) resulted in the complete loss of RpoS translation (Majdalani, et al. (1998) *Proc Natl Acad Sci USA* 95: 12462-12467). To investigate this inconsistency, a series of A40 mutants differing in their 5' termini were generated (FIG. 12A). A40a is identical to the previously characterized DSL1 sequence and begins with 5'-AACAU (SEQ ID NO: 41). A40b contains a deletion of all the nucleotides before the linker and therefore starts with 5'-AACGAA (SEQ ID NO: 42), while A40c begins with the last U of SL1 (5'-UAACGAA) (SEQ ID NO: 43).

Consistent with previous findings, A40a (DSL1) was 6-fold less active than A40 (FIG. 11C). In contrast, A40c activates translation at least as potently as wild-type DsrA, while A40b (differing from A40c only in the loss of a single 5'-U) was 2-fold less active than A40c. The current model for DsrA activation of rpoS translation invokes an anti-antisense mechanism that must precisely balance intramolecular DsrA hairpin formation with intermolecular DsrA-rpoS duplex formation (FIGS. 9B and 9C). If base pairing between DsrA and rpoS mRNA is too weak, translational activation cannot take place, while if hybridization is robust, the level of rpoS translation is high. In this model, DsrA U22 (directly preceding the SL1-SL2 linker) pairs with A113 of rpoS mRNA (FIGS. 9B and 94A). Clone A40 contains U22 as well as the two preceding nucleotides (U20 and G21); these two bases can further pair with A115 and C114 of rpoS mRNA, favoring intermolecular hybridization. A40a, however, replaces U20 and G21 with AACA, bases that cannot pair with the rpoS leader; duplex formation is less favorable as a result and rpoS activation decreases 6-fold (FIG. 11C). Removal of the mismatching AACA (clone A40c) fully restores LacZ activity.

Comparing the activities of A40b and A40c reveals that a single DsrA-rpoS base pair can significantly affect translational activation. Reducing the number of possible base pairs between DsrA and rpoS mRNA from 11 (A40c) to ten (A40b) reduces translational activation by 2-fold (FIG. 11C). Collectively, these results show that pairing interactions between the SL1-SL2 linker of DsrA and the complementary region of the rpoS UTR can precisely tune translational regulation.

These findings indicate that beyond the small number of bases that pair with the RpoS mRNA, the substantial majority of SL1 is not required for translational activation. When present, however, SL1 can contribute to pairing as well, this could be particularly important when DsrA levels are low, as in physiological conditions. But because there is little thermodynamic incentive for SL1 to unfold and swap intramolecular base pairs for intermolecular ones, it is not surprising that SL1 is not required for DsrA activity when sRNA concentrations are higher. The evolutionary conservation of SL1, however, suggests that this region plays a significant role in rpoS translational activation. The intracellular abundance assays above indicate that one possible role for SL1 consistent with our observations is to stabilize the sRNA, rather than to necessarily base pair with the rpoS mRNA.

(i) Selection of Translational Repressors from an OxyS-Based Library

Figure 13:
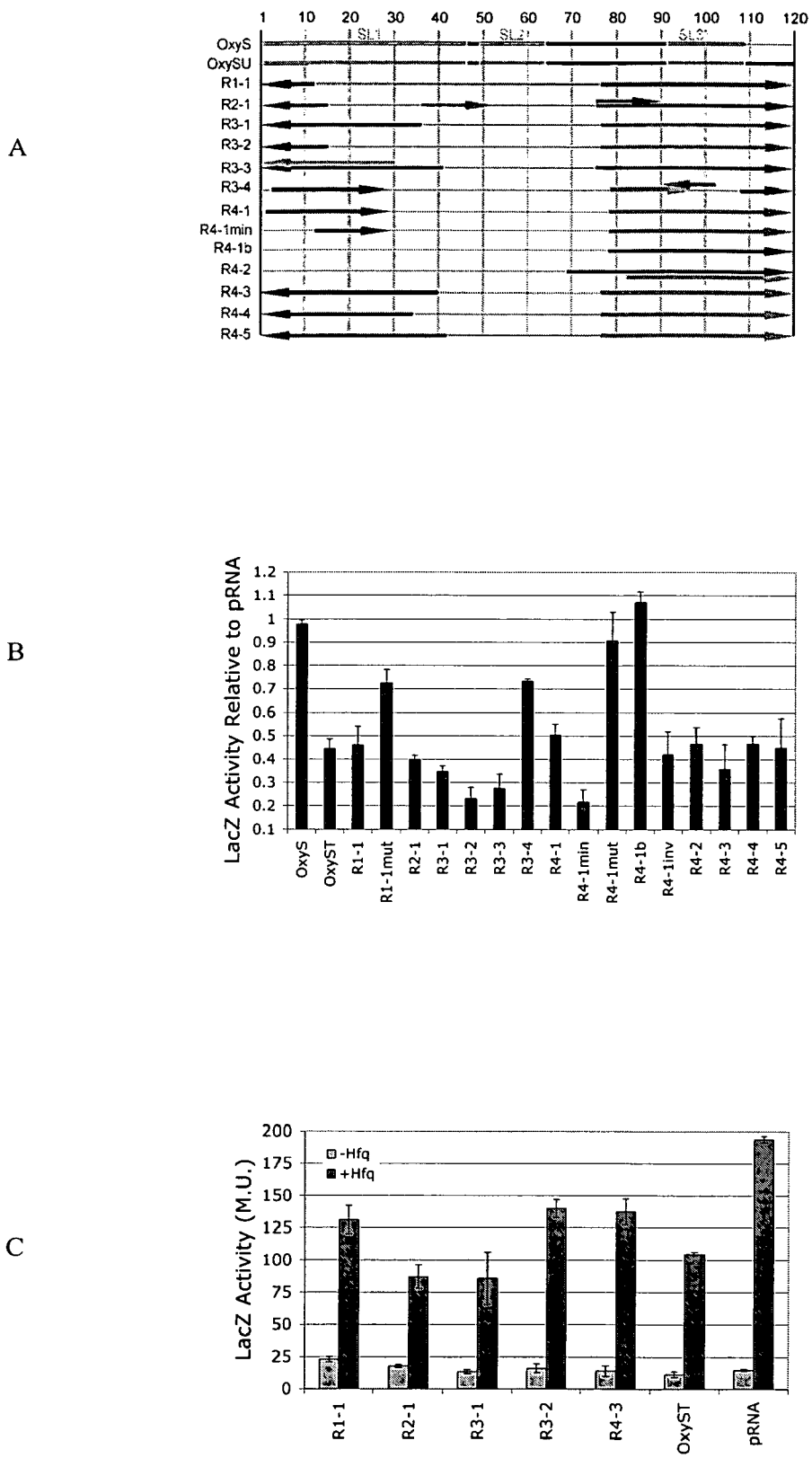
FIG. 13A shows the composition of selected OxyS variants that repress RpoS translation.
FIG. 13B is a bar graph showing translational repression activities of selected OxyS variants.
FIG. 13C is a bar graph showing translational repression activities of OxyS variants in the presence and absence of Hfq.

NRR-diversified repressor libraries R1 and R2 were separately introduced into E. coli cells harboring pProt-CcdB, each resulting in ~$10^6$ transformants. Following selection, RNA-encoding inserts from surviving colonies (one in $8 \times 10^3$) were pooled, recloned into pRNA, and reselected. One in 600 transformants survived reselection, suggesting that repressors were enriched 13-fold by reselection. Two highly represented sequences, R1-1 (12 out of 64 clones) and R2-1 (six out of 64 clones), were confirmed to repress the translation of both rpoS-ccdB and rpoS-lacZ (FIGS. 13A, 13B and S1). FIG. 12 shows the translational repression of RpoS by selected sequences. FIG. 5(A) shows a composition of selected OxyS variants that repress RpoS translation. The labeling scheme is the same as described in FIG. 10B. FIG. 13(B) shows the translational repression activities of selected OxyS variants. OxyS represents the 109 ucleotide wild-type OxyS sequence; OxyST represents the wild-type OxyS sequence with the T-rich region appended to the 3' end. FIG. 13(C) shows the translational repression activities of OxyS variants in the presence and absence of Hfq. Miller units (M.U.) are used to quantitatively represent b-galactosidase expression from an RpoS-LacZ fusion. Error bars represent standard deviations of three or more independent trials.

As observed with the original pRNA-DsrA construct, the sRNA expressed from pRNA-OxyS exhibited activity different from that previously reported; in particular, pRNA-OxyS cells only weakly survived the selection and showed no translational repression of rpoS-lacZ (FIG. 13B). Moreover, sequence analysis of R1-1 and R2-1 revealed an unexpected 3' T-rich fragment not present in the canonical 109 nucleotide oxyS gene used to construct libraries R1 and R2. We reasoned that this fragment (5'-TTTTTTTTGCC) (SEQ ID NO: 44) entered the NRR process through the use of pOxyS as a PCR template.

The presence of this fragment in both active sequences despite its very low abundance in the starting DNA pool strongly suggested the importance of transcriptional termination directly after SL3 of oxyS. Addition of the T-rich region to our oxyS construct (pRNA-OxyST) allowed for survival in the rpoS-ccdB selection and repression of rpoS-lacZ translation (FIG. 12B).

As opposed to the activator selection, it was not possibe to select for sRNA repressors without the T-rich 3'-end. In light of these results, we constructed two additional NRR-diversified oxyS libraries, R3 and R4, which either allowed the T-rich region to be recombined throughout the library (R3), or which appended this T-rich region to the 3' end of all library members (R4). R3 and R4 were selected for translational repression as described above ($5 \times 10^6$ and $1 \times 10^6$ transformants, respectively). After two rounds of selection, four unique sequences from R3 and five from R4 repressed RpoS-LacZ expression (FIGS. 13A and 13B). Including R1-1 and R2-1, ten of the 11 selected sequences contain two small regions of OxyS (FIG. 13A), suggesting that these regions are required for translational repression. All of the selected sequences, moreover, contain the U-rich putative Hfq-binding region, found in the linker between OxyS SL2 and SL3 (Zhang, et al. (1998) Supra). When assayed in an Hfq-deficient strain, a representative set of five of the selected sequences were all inactive, mirroring the Hfq dependence of wild-type OxyS (FIG. 13C). Together with our control selections described above, these results strongly suggest that the selected sequences repress rpoS translation in a manner similar to that of wild-type OxyS.

(j) Intracellular Abundance of Selected sRNA Repressors

As with the translational activators described above, quantitative reverse transcriptase-PCR was used to analyze the intracellular abundance of a representative set of selected translational repressors and their mutants, which are discussed below (FIGS. 14E and 14F). In general, all sequences were comparably abundant indicating that differences in activities among the OxyS mutants described cannot be explained simply by changes in their intracellular abundance. For example, although R4-1min was five-fold more active than R4-1b, there was no significant difference in their intracellular abundance. In contrast, OxyS was five-fold less abundant than OxyST, suggesting that the additional 3' nucleotides added to OxyS by the rmB terminator decreases the stability of the sRNA.

Figure 9:
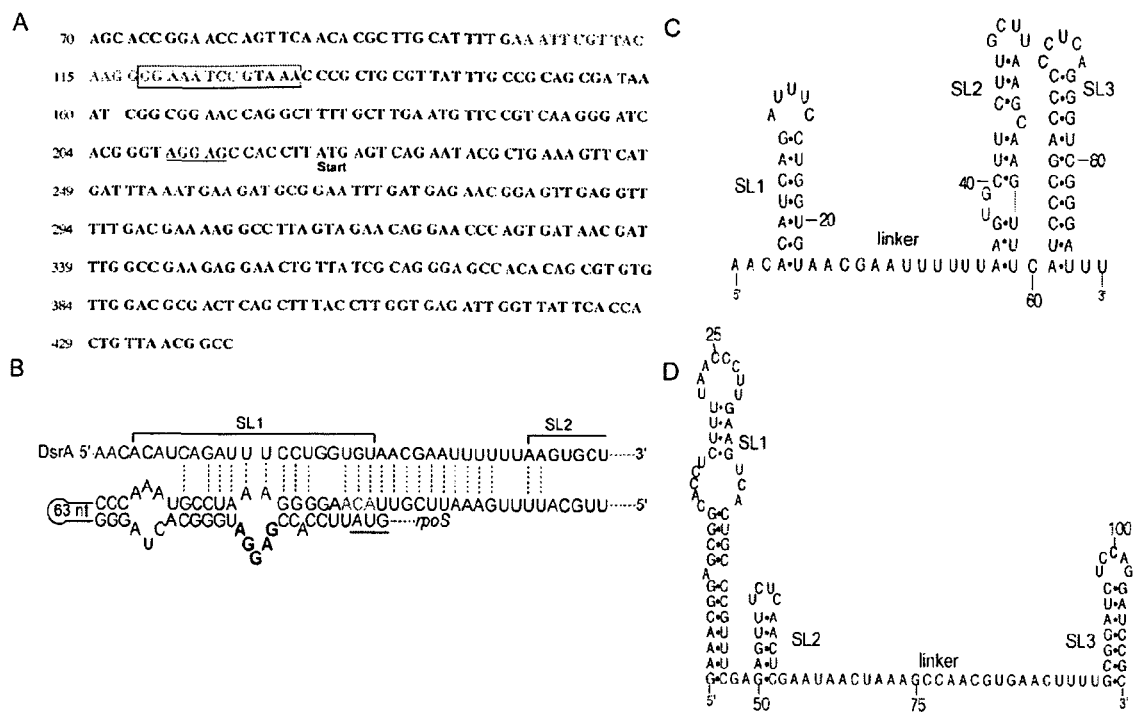
FIG. 9A is a RpoS mRNA sequence (SEQ ID NO. 45) including the 150 nucleotide of the 5' UTR and the region coding for the first 73 amino acid residues.
FIG. 9B is a model of RpoS 5' UTR secondary structure (SEQ ID NO. 46) and proposed anti-antisense mechanism for translational activation by DsrA (SEQ ID NO. 47)
FIG. 9C is a DsrA secondary structure (SEQ ID NO. 48) as predicted by nuclease footprinting.
FIG. 9D is an OxyS secondary structure (SEQ ID NO. 49) as predicted by the mFOLD program.
Figure 14:
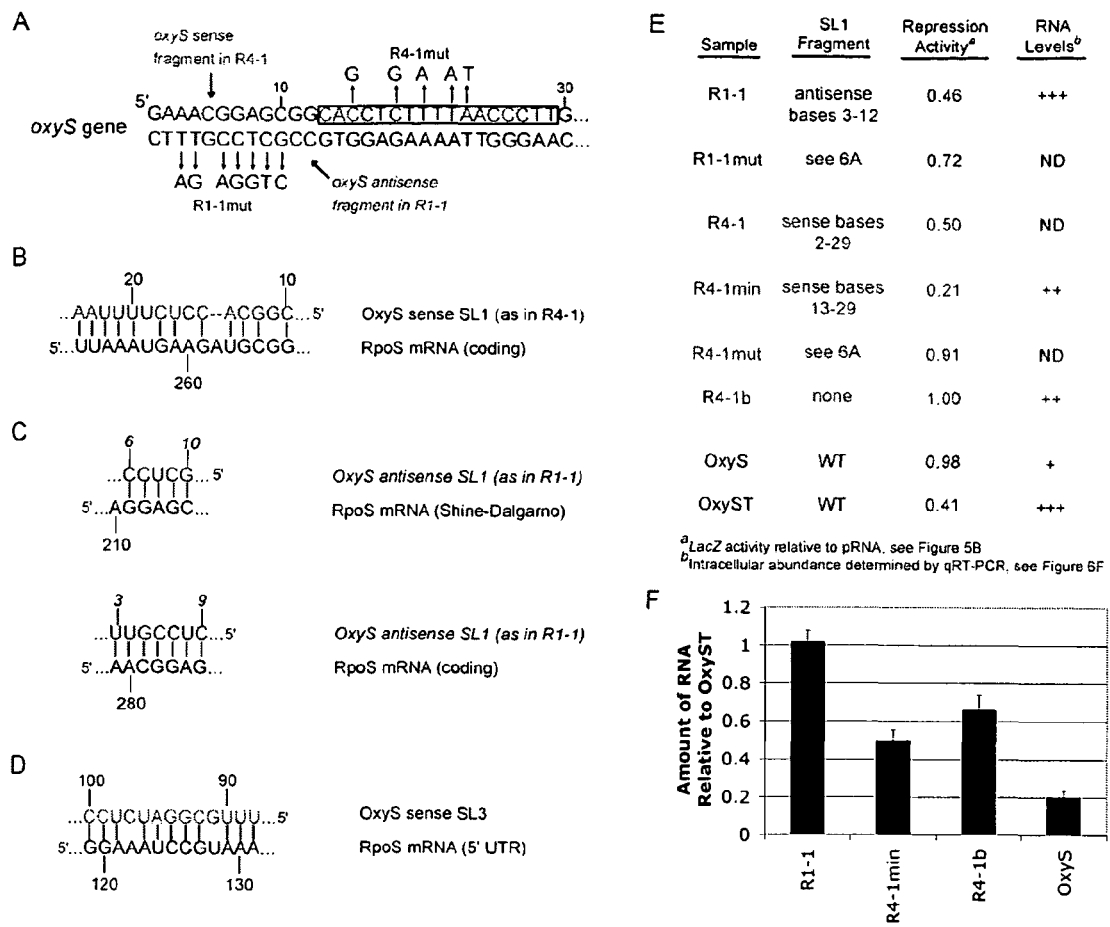
FIG. 14A is the first third of the oxyS gene (SEQ ID NO. 54) showing both the sense and antisense strands.
FIG. 14B shows mutations introduced to generate R1-1mut and R4-1mut are indicated by the arrows and the proposed pairing between the RpoS mRNA (SEQ ID NO. 55) and OxyS SL1 (SEQ ID NO. 56) sense fragment.
FIG. 14C shows the proposed pairing between RpoS mRNA and OxyS SL1 antisense fragment.
FIG. 14D shows the proposed pairing between RpoS mRNA (SEQ ID NO. 57) and SL3 fragments (SEQ ID NO. 58)
FIG. 14E shows a comparison of 5' sequence, translational repression activity and intracellular abundance.
FIG. 14F is a bar graph showing the intracellular abundance of sRNA repressors, relative to OxyS, as measured by quantitative reverse transcriptase PCR.

FIG. 14 show the sequence analysis of selected translational repressors. FIG. 14(A) shows the first third of the oxyS gene showing both the sense and antisense strands. The SL1 sense fragment found in R4-1 is highlighted in red. The SL1 antisense fragment found in R1-1 is highlighted in blue. The boxed sequence represents the minimal SL1 found in R4-1 min. Mutations introduced to generate R1-1mut and R4-1mut are indicated by the arrows. (B-D) Proposed pairing between the RpoS mRNA and FIG. 14(B) the OxyS SL1 sense fragment; FIG. 14(C) SL1 antisense fragments; and FIG. 14(D) SL3 fragments. Base numbering is as shown in FIG. 9. Nucleotides from the antisense strand are numbered according to their sense strand base-pair partner, in italics. FIG. 14(E) Comparison of 5' sequence, translational repression activity and intracellular abundance. Sequences containing the antisense OxyS SL1 sequence are in blue. Sequences containing the sense OxyS SL1 sequence are in red. FIG. 14(F) Intracellular abundance of sRNA repressors, relative to OxyS, as measured by quantitative reverse transcriptase PCR. Error bars represent standard deviations of three or more independent trials.

(k) The Role of OxyS Stem-Loop 1

The first region conserved among selected OxyS variants is the 5' end of SL1. Ten of the 11 selected OxyS variants contain either a short antisense portion of the 5' end of the OxyS parent (e.g., the reverse complement of OxyS bases 3-12 as in clone R1-1), or a longer sense portion (e.g., OxyS bases 2-29 as in clone R4-1) (FIG. 14A). Both of these conserved SL1 fragments are partially complementary to the coding region of the rpoS mRNA (FIGS. 14B and 14C). Additionally, the sense fragment of OxyS SL1 recovered from our selections and the complementary region of rpoS are both evolutionarily highly conserved. These results suggest that the 5' end of SL1 may interact with the rpoS mRNA through base pairing. Further, the absence of the majority of SL1 among active clones demonstrates that the SL1 stem-loop structure is not required for OxyS translational repressor activity.

To further isolate the putative rpoS-pairing region in R4-1, the first 11 bases of R4-1 were deleted to generate mutant R4-1 min. An alignment predicts that these eliminated bases do not pair with the rpoS mRNA (FIG. 14B). This "minimal OxyS" construct was indeed fully active as a translational repressor (FIG. 13B), consistent with the dispensability of the first third of SL1.

Three additional mutants were constructed to further test the hypothesis that a portion of SL1 pairs with the RpoS mRNA (FIG. 14). The SL1 fragment complementary to rpoS was mutated in clones R1-1 and R4-1 such that the resulting mutants (R1-1mut and R4-1mut) cannot base pair with the rpoS mRNA (FIG. 14A). The entire SL1 fragment of R4-1 was also deleted to create R4-1b. All three mutants possess no significant translational repression activity (FIGS. 13B and 13E). Taken together, these results are consistent with a regulatory mechanism in which the central third of OxyS SL1 base pairs with the rpoS mRNA to repress translation.

(l) The Role of OxyS Stem-Loop 3

The ten most active OxyS variants all contain a second conserved region: the last 40 bases of OxyS (comprising a portion of the SL2-SL3 linker, SL3, and the 3' T-rich region). While this region appears necessary for translational repression, the inactivity of mutant R4-1b demonstrates that this region is not sufficient for activity (FIG. 13B). This region includes a stretch of 13 nucleotides containing 11 bases complementary to the rpoS mRNA (FIG. 14D), raising the possibility that it interacts with the rpoS mRNA through base pairing. To probe this possibility, base pairs in SL3 of R4-1min were inverted (R4-1inv) to abrogate putative base pairing between SL3 and the rpoS mRNA while preserving the ability of the modified SL3 form a stem-loop. This mutant was 2-fold less active than R4-1min, suggesting that SL3 may also base pair with the rpoS mRNA, but that this pairing is not essential for translational repression.

The discovery of two regions of OxyS that participate in translational repression but are not contiguous in primary sequence illustrates a strength of NRR in revealing the functional components of nucleic acids; a simple truncation analysis would not reveal these regions as distinct essential elements. OxyS has also been implicated in the translational repression of fhlA, a transcriptional activator of formate metabolism (A1 tuvia, et al. (1998) *Embo J* 17: 6069-6075; and Zuker, et al. (2003) *Nucl. Acids Res* 31: 3406-3415). Intriguingly, Argaman and A1 tuvia have demonstrated that OxyS contains two sites that target the fhlA mRNA through base pairing (Argaman, et al. (2000) *J. Mol. Biol.* 300: 1101-1112). The resulting interaction is thought to lead to translational repression. The above results are consistent with the possibility that OxyS regulates rpoS expression through a similar base-pairing mechanism involving the 5' half of SL1 and possibly SL3.

(C) Conclusion.

Figure 15:
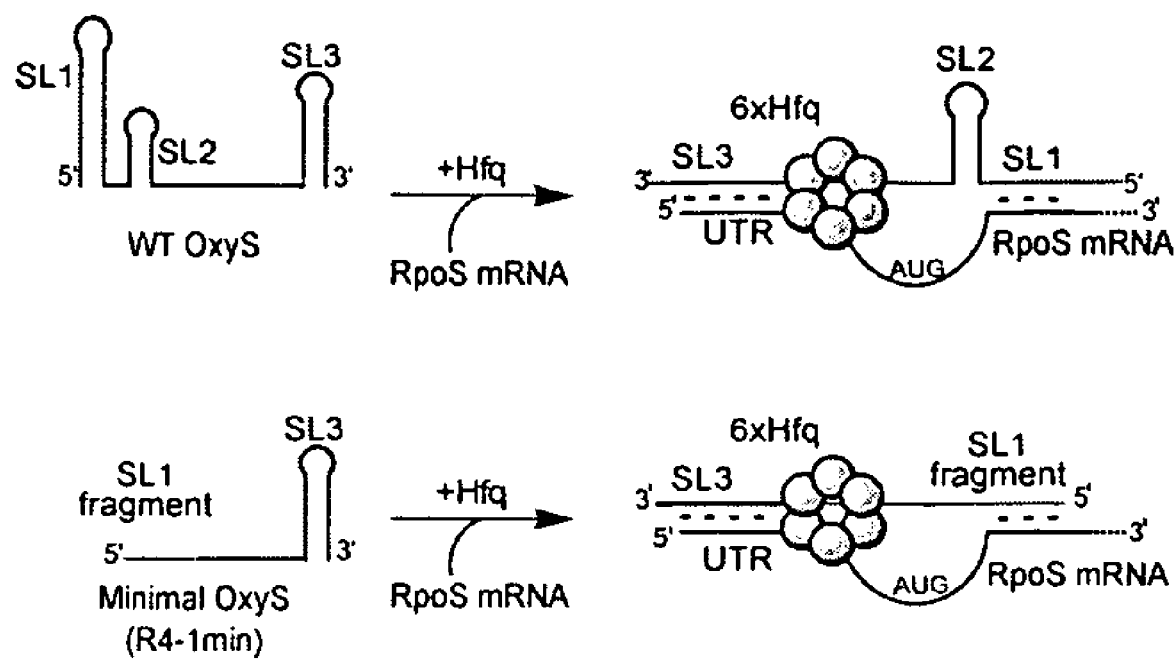
FIG. 15 is a model of RpoS Translation Repression by OxyS.

NRR diversification and in vivo selection can be applied to functionally dissect sRNA regulators of rpoS translation in a manner independent of previous assumptions. This approach requires no prior knowledge of sRNA function beyond that necessary to establish a selection or efficient screen. The results suggest two essential components for DsrA activity: the SL1-SL2 linker and SL3. The above findings also reveal that the primary role of SL1 is in stabilizing DsrA rather than playing a direct role in translational regulation. In addition, two portions of OxyS were identified that are necessary and collectively sufficient for activity: (i) a small fragment of the 5' half of SL1 that may function by base pairing with the rpoS mRNA, and (ii) a region including the transcriptional-terminator SL3, respectively. A resulting model for the interaction of OxyS with the rpoS mRNA is shown in FIG. 15. The model of OxyS-mediated translational repression of RpoS translation based on the results presented in this work. A fragment of SL1 is proposed to base pair with a downstream region of the RpoS mRNA, while a region of SL3 may also pair with the RpoS 5' UTR. These two fragments are necessary and sufficient to induce wild-type levels of translational repression. The application of this approach to additional biological pathways will continue to prove useful for the functional dissection of novel natural nucleic acids.

A number of embodiments of the invention have been described. Nevertheless, it will be understood that various modifications may be made without departing from the spirit and scope of the invention. Accordingly, other embodiments are within the scope of the following claims.

The invention claimed is:

1. A method for producing an evolved polypeptide comprising:

randomly fragmenting two or more double stranded parent nucleic acids and generating three or more nucleic acid fragments from each of the parent nucleic acids, wherein at least one of the parent nucleic acids is capable of encoding a protein, and at least one of the nucleic acid fragments encodes a fragment of the protein;

ligating at least a subset of the nucleic acid fragments and generating shuffled nucleic acids, wherein the nucleic acid fragments and the shuffled nucleic acids are double stranded and at least one of the shuffled nucleic acids comprises nucleic acid fragments from at least two of the parent nucleic acids and encodes the evolved polypeptide;

ligating at least one hairpin oligonucleotide to each end of at least a subset of the shuffled nucleic acids to cap each end of the subset of the shuffled nucleic acids, and forming capped shuffled nucleic acids thereby controlling the average length of the subset of the shuffled nucleic acids wherein each end of the capped shuffled nucleic acids can no longer ligate to other nucleic acid molecules, and at least one of the subset of the shuffled nucleic acids and at least one of the capped shuffled nucleic acids encode the evolved polypeptide;

uncapping the capped shuffled nucleic acids by cleaving the hairpin oligonucleotide from the capped shuffled nucleic acids and generating uncapped shuffled nucleic acids encoding the evolved polypeptide;

transforming the at least one of the uncapped shuffled nucleic acids encoding the evolved polypeptide into a host cell; and expressing the evolved polypeptide encoded by the at least one of the uncapped shuffled nucleic acids encoding the evolved polypeptide.

2. The method of claim 1, wherein the parent nucleic acids are non-homologous and non-complementary.

3. The method of claim 1, wherein the step of fragmenting the parent nucleic acids further comprises using a non-site specific agent to fragment the parent nucleic acids.

4. The method of claim 3, wherein the non-site specific agent is selected from the group consisting of a nonspecific endonuclease, a blunt-end endonuclease, and a chemical reagent.

5. The method of claim 3, wherein the non-site specific agent is DNase I.

6. The method of claim 1, wherein the method further includes adding at least two species of hairpin oligonucleotides, wherein each of the at least two species comprises a different nonpalindromic restriction endonuclease cleavage site.

7. The method of claim 1, wherein the step of transforming further comprises introducing the at least one of the uncapped shuffled nucleic acids encoding the evolved polypeptide into an expression vector.

8. The method of claim 1, wherein the nucleic acid fragments have at least one nucleic acid fragment that is inserted, deleted, or rearranged to produce the at least one of the shuffled nucleic acids that encodes the evolved polypeptide.

9. The method of claim 1, wherein the average size of the least one of the shuffled nucleic acids encoding the evolved polypeptide is less than about 2000 nucleotides.

10. The method of claim 1, wherein the uncapped shuffled nucleic acids encoding the evolved polypeptide comprise a plurality of different uncapped shuffled nucleic acids and further comprising producing a library of the evolved polypeptide comprising:

transforming the plurality of different uncapped shuffled nucleic acids into a host cell; and expressing a plurality of polypeptides of the evolved polypeptide encoded by the plurality of the uncapped shuffled nucleic acids.

11. A method for producing an evolved chimeric polypeptide comprising:

fragmenting a double stranded first nucleic acid encoding a first protein with at least one structural feature and generating three or more nucleic acid fragments, wherein at least one of the nucleic acid fragments encodes a fragment of the first protein;

fragmenting a double stranded second nucleic acid encoding a second protein with at least one structural feature and generating three or more nucleic acid fragments, wherein at least one of the nucleic acid fragments generated from the second nucleic acid encodes a fragment of the second protein;

ligating at least a subset of the nucleic acid fragments that encode the fragment of the first protein with at least a subset of the nucleic acid fragments that encode the fragment of the second protein at random and generating shuffled chimeric nucleic acids, wherein the nucleic acid fragments that encode the fragments of the first and second proteins and the shuffled chimeric nucleic acids are double stranded and at least one of the shuffled chimeric nucleic acids comprises a nucleic acid fragment that encodes the fragment of the first protein and a nucleic acid fragment that encodes the fragment of the second protein and encodes the evolved chimeric polypeptide;

ligating at least one hairpin oligonucleotide to each end of at least a subset of the shuffled chimeric nucleic acids to cap each end of the shuffled chimeric nucleic acids, and forming capped shuffled chimeric nucleic acids thereby regulating the length of the subset of the shuffled chimeric nucleic acids wherein each end of the capped shuffled chimeric nucleic acids can no longer ligate to other nucleic acid molecules, and at least one of the subset of the shuffled chimeric nucleic acids and at least one of the capped shuffled chimeric nucleic acids encode the evolved polypeptide;

uncapping the capped shuffled chimeric nucleic acids by cleaving the hairpin oligonucleotide from the capped shuffled chimeric nucleic acids and generating uncapped shuffled chimeric nucleic acids encoding the evolved chimeric polypeptide;

transforming at least one of the uncapped shuffled chimeric nucleic acids encoding the evolved chimeric polypeptide into a host cell; and expressing the evolved chimeric polypeptide encoded by the at least one of the shuffled chimeric nucleic acids encoding the evolved chimeric polypeptide.

12. The method of claim 11, wherein the first nucleic acid encoding the first protein and the second nucleic acid encoding the second protein are non-homologous and non-complementary.

13. The method of claim 11, wherein each of the at least one of the nucleic acid fragments encoding the fragment of the first protein has a terminus that can be ligated to at least one non-adjacent fragment.

14. The method of claim 11, wherein each of the at least one of the nucleic acid fragments encoding the fragment of the second protein has a terminus that can be ligated to at least one non-adjacent fragment.

15. The method of claim 11, wherein the first and second nucleic acids are fragmented by a non-site specific agent.

16. The method of claim 15, wherein the non-site specific agent is DNase I.

17. The method of claim 11, wherein the nucleic acid fragments that encode the fragments of the first and second proteins have at least one nucleic acid fragment that is inserted, deleted, or rearranged to produce the at least one of the shuffled chimeric nucleic acids that encodes the evolved chimeric polypeptide.

18. The method of claim 11, wherein the average size of the nucleic acid fragments generated from the first and second nucleic acids is less than about 2000 nucleotides.

19. The method of claim 11, wherein the uncapped shuffled chimeric nucleic acids encoding the evolved chimeric polypeptide comprise a plurality of different uncapped shuffled chimeric nucleic acids and further comprising producing a library of the evolved chimeric polypeptide comprising:
    transforming the plurality of the uncapped shuffled chimeric nucleic acids into a host cell; and
    expressing a plurality of polypeptides of the evolved chimeric polypeptide encoded by the plurality of the different uncapped shuffled chimeric nucleic acids.

* * * * *